(12) United States Patent
Becker et al.

(10) Patent No.: US 8,093,237 B2
(45) Date of Patent: Jan. 10, 2012

(54) DIBENZO[B,F][1,4]OXAZAPINE COMPOUNDS

(75) Inventors: Cyrus Becker, Fremont, CA (US);
Courtney Rubens, San Jose, CA (US);
Jason Adams, Fremont, CA (US);
Monica Palme, Fremont, CA (US);
Pascal Druzgala, Santa Rosa, CA (US)

(73) Assignee: ARYx Therapeutics, Inc., Fremont, CA (US)

( * ) Notice: Subject to any disclaimer, the term of this patent is extended or adjusted under 35 U.S.C. 154(b) by 877 days.

(21) Appl. No.: 12/047,858

(22) Filed: Mar. 13, 2008

(65) Prior Publication Data
US 2008/0255088 A1    Oct. 16, 2008

Related U.S. Application Data

(60) Provisional application No. 60/895,046, filed on Mar. 15, 2007.

(51) Int. Cl.
*A61P 25/00* (2006.01)
*A61K 31/553* (2006.01)
*C07D 267/02* (2006.01)

(52) U.S. Cl. .................... 514/211.13; 540/551

(58) Field of Classification Search .............. 514/211.13; 540/551
See application file for complete search history.

(56) References Cited

U.S. PATENT DOCUMENTS
2006/0069083 A1    3/2006    Steiner et al.

FOREIGN PATENT DOCUMENTS
WO          96/18629         6/1996
WO          03082877         10/2003
WO          2004014895       2/2004

*Primary Examiner* — Brenda Coleman
(74) *Attorney, Agent, or Firm* — McDonnell Boehnen Hulbert & Berghoff LLP

(57) ABSTRACT

The present invention relates to 11-(piperazin-1-yl)dibenzo[b,f][1,4]oxazapine compounds of the formula:

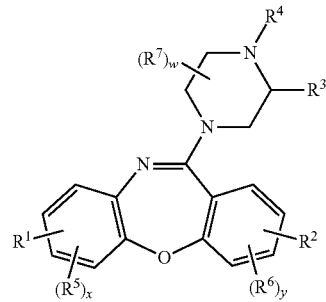

where the variables are as defined herein, their salts and pharmaceutically acceptable compositions thereof. Methods of preparing these compounds are also described. These compounds may be used in the treatment of disorders such as schizophrenia, treatment resistant schizophrenia, bipolar disorder, psychotic depression, treatment resistant depression, schizophrenia-associated depression, treatment resistant OCD, autism, senile psychosis, psychotic dementia, L-DOPA induced psychosis, psychogenic polydipsia, psychotic symptoms of neurological disorders, sleep disorders.

36 Claims, 8 Drawing Sheets

DIBENZO[B,F][1,4]OXAZAPINE COMPOUNDS

CROSS-REFERENCES TO RELATED APPLICATIONS

This application claims the benefit of the U.S. Provisional Application No. 60/895,046, filed Mar. 15, 2007, which is incorporated by reference herein in its entirety.

BACKGROUND OF THE INVENTION

1. Field of the Invention

The present invention relates generally to dibenzo[b,f][1,4]oxazapine compounds, and more particularly to 11-(piperazin-1-yl)benzo[b,f][1,4]oxazapine compounds.

2. Technical Background

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, Rev. Neurol. 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, Biology of Serotonergic Transmission, 1982; Boullin, Serotonin In Mental Abnormalities 1:316 (1978); Barchas, et al., Serotonin and Behavior, (1973)). The $5\text{-HT}_{2A}$ receptor subtype (also referred to as subclass) is widely yet discretely expressed in the human brain, including many cortical, limbic, and forebrain regions postulated to be involved in the modulation of higher cognitive and affective functions.

Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the $5\text{-HT}_{2A}$ subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they can activate or inactivate these molecules, respectively. In contrast, classic or neutral antagonists compete against agonists and inverse agonists for access to the receptor, but do not possess the intrinsic ability to inhibit elevated basal or constitutive receptor responses.

At least 15 genetically distinct 5-HT receptor subtypes have been identified and assigned to one of seven families ($5\text{-HT}_{1-7}$). Each subtype displays a unique distribution, preference for various ligands, and functional correlate(s).

Serotonin may be an important component in various types of pathological conditions such as psychiatric disorders (depression, aggressiveness, panic attacks, obsessive compulsive disorders, psychosis, schizophrenia, suicidal tendency), neurodegenerative disorders (Alzheimer-type dementia, Parkinsonism, Huntington's chorea), anorexia, bulimia, disorders associated with alcoholism, cerebral vascular accidents, and migraine (Meltzer, Neuropsychopharmacology, 21:106 S-115S (1999); Barnes & Sharp, Neuropharmacology, 38:1083-1152 (1999); Glennon, Neurosci. Biobehavioral Rev., 14:35 (1990)). Recent evidence strongly implicates the $5\text{-HT}_2$ receptor subtype in the etiology of such medical conditions as, among others, hypertension, thrombosis, migraine, vasospasm, ischemia, depression, anxiety, psychosis, schizophrenia, sleep disorders, and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes and the degree to which an antipsychotic drug agonizes or antagonizes the various receptor subtypes. The high degree of genetic and pharmacological homology between these receptor subtypes has hampered the development of drug compounds (antipsychotic and other indications mentioned above and elsewhere herein) that possess a desired pharmacological profile in the absence of, or with acceptably reduced, undesired side effects.

SUMMARY OF THE INVENTION

One aspect of the invention provides compounds having the structure depicted by Formula I:

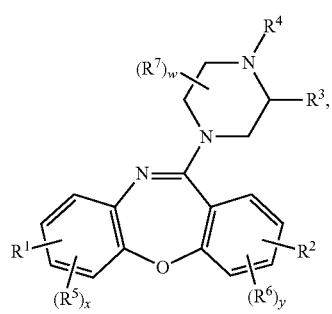

(I)

and pharmaceutically acceptable salts thereof, in which:

$R^1$ and $R^2$ are independently —Cl, —F, —Br, —I or —H;

$R^3$ is —R (nonoptionally substituted in this single instance at $R^3$), —($C_0$-$C_6$ alk)C(O)O$R^e$, —($C_0$-$C_6$ alk)C(O)N$R^a{}_2$, —($C_0$-$C_6$ alk)C(O)N$R^a R^{19}$, —($C_0$-$C_6$ alk)C(O)N$R^{19}{}_2$, —($C_0$-$C_6$ alk)C(O)N$R^{20}$, —($C_0$-$C_6$ alk)Ar, —($C_0$-$C_6$ alk)-O—($C_0$-$C_6$ alk)Ar, —($C_0$-$C_6$ alk)-OR, —($C_0$-$C_6$ alk)C(O)$R^k$, or —($C_0$-$C_6$ alk)-N $R^a R^{19}$;

$R^4$ is —H or —R;

each $R^5$, $R^6$ and $R^7$ is independently —R, —($C_0$-$C_6$ alk)-OR, —($C_0$-$C_6$ alk)-N$R^a R^{19}$, —$NO_2$, -halogen, —CN, —OH, —OOCR, —($C_0$-$C_6$ alk)COO$R^e$, —($C_0$-$C_6$ alk)C(O)N$R^a R^{19}$, —($C_0$-$C_6$ alk)Ar, —($C_0$-$C_6$ alk)-O—($C_0$-$C_6$ alk)Ar, —($C_0$-$C_6$ alk)Het, —($C_0$-$C_6$ alk)-O—($C_0$-$C_6$ alk)Het, —($C_0$-$C_6$ alk)Hca, —($C_0$-$C_6$ alk)-O—($C_0$-$C_6$ alk)Hca, —($C_0$-$C_6$ alk)Cak, —($C_0$-$C_6$ alk)-O—($C_0$-$C_6$ alk)Cak, —($C_0$-$C_6$ alk)C(O)Hca, —($C_0$-$C_6$ alk)C(O)Ar, —($C_0$-$C_6$ alk)C(O)Het, or —($C_0$-$C_6$ alk)C(O)Cak;

w is 0, 1, 2 or 3;

x is 0, 1, 2 or 3; and y is 0, 1, 2 or 3, in which each $R^e$ is independently —H, —R, —($C_1$-$C_6$ alk)C(O)Hca, —($C_1$-$C_6$ alk) C(O)Cak, —($C_1$-$C_6$ alk)C(O)Het, —($C_1$-$C_6$ alk)C(O)Ar, —($C_1$-$C_6$ alk)C(O)O-Hca, —($C_1$-$C_6$ alk)C(O)O-Cak, —($C_1$-$C_6$ alk)C(O)O-Het, —($C_1$-$C_6$ alk)C(O)O—Ar, —($C_0$-$C_6$ alk) Hca, —($C_0$-$C_6$ alk) Het, —($C_0$-$C_6$ alk) Ar, —($C_0$-$C_6$ alk)Cak, —($C_1$-$C_6$ alk)C(O)OR, —($C_1$-$C_6$ alk)C(O)N$R^{19}{}_2$, —($C_0$-$C_6$ alk)-OR, or —($C_0$-$C_6$ alk)-OH;

each $R^a$ is independently —H, —R, —($C_1$-$C_6$ alk)-OR, —($C_1$-$C_6$ alk)-OH, —($C_0$-$C_6$ alk)C(O)OR, —($C_1$-$C_6$ alk)-N$R^{19}{}_2$, —($C_0$-$C_6$ alk)Hca, —($C_0$-$C_6$ alk)Ar, —($C_0$-$C_6$ alk)Het, or —($C_0$-$C_6$ alk)Cak;

each $R^k$ is independently —H, —R, —($C_1$-$C_6$ alk)C(O)Hca, —($C_1$-$C_6$ alk)C(O)Cak, —($C_1$-$C_6$ alk)C(O)Het, —($C_1$-$C_6$ alk)C(O)Ar, —($C_1$-$C_6$ alk)Hca, —($C_0$-$C_6$ alk)Het, —($C_0$-$C_6$ alk)Ar, —($C_0$-$C_6$ alk)Cak, —($C_1$-$C_6$ alk)C(O)OR, or —($C_1$-$C_6$ alk)C(O)N$R^{19}{}_2$;

each Cak is a cycloalkyl or cycloalkenyl group, optionally substituted with 1, 2 or 3 substituents independently selected from —R, —($C_0$-$C_6$ alk)C(O)OR, =O, —OH, —CN, —($C_0$-$C_6$ alk)OR, —OCH$_2$CH$_2$—O—, —OCH$_2$—O—, —SO$_2$—R, —SO$_2$—($C_1$-$C_6$ haloalkyl), —($C_0$-$C_6$ alk)C(O)N$R^{19}{}_2$, —($C_0$-$C_6$ alk)Het, —SO$_2$($C_0$-$C_6$ alk)-Hca, —($C_0$-$C_6$ alk)Ar, —($C_0$-$C_6$ alk)Het, —($C_0$-$C_6$ alk)Hca, —($C_0$-$C_6$ alk)C(O)R, —SO$_2$($C_0$-$C_6$ alk)Ar, —SO$_2$($C_0$-$C_6$ alk)Het, and —SO$_2$($C_0$-$C_6$ alk)cycloalk, each Ar is an aryl group, optionally substituted with 1, 2 or 3 substituents independently selected from —R, —OR, —($C_0$-$C_6$ alk)N$R^{19}{}_2$, —NO$_2$, —Cl, —F, —Br, —I, —CN, —($C_0$-$C_6$ alk)OH, —($C_0$-$C_6$ alk)C(O)OR, —($C_0$-$C_6$ alk)C(O)OH, —($C_1$-$C_6$ haloalkyl), —O($C_1$-$C_6$ haloalkyl), —($C_0$-$C_6$ alkyl)heterocycloalk, —SO$_2$R, —($C_0$-$C_6$ alk)-C)(O)-heterocycloalk, —($C_0$-$C_6$ alk)-C(O)-cycloalk, —($C_0$-$C_6$ alkyl)-C(O)-heteroaryl, —($C_0$-$C_6$ alk)-C(O)-aryl, —($C_0$-$C_6$ alkyl)-C(O)O-heterocycloalk, —($C_0$-$C_6$ alk)-C(O)O-cycloalk, —($C_0$-$C_6$ alkyl)-C(O)O-heteroaryl, —($C_0$-$C_6$ alk)-C(O)O-aryl, —($C_0$-$C_6$ alk)-heterocycloalkyl, —($C_0$-$C_6$ alk)-heteroaryl, —($C_0$-$C_6$ alk)-aryl, and —($C_0$-$C_6$ alk)-cycloalk;

each Het is a heteroaryl group, optionally substituted with 1, 2 or 3 groups independently selected from —R, —OR, —($C_0$-$C_6$ alk)N$R^{19}{}_2$, —NO$_2$, —Cl, —F, —Br, —I, —CN, —($C_0$-$C_6$ alk)OH, —($C_0$-$C_6$ alk)CO$_2$R, —($C_0$-$C_6$ alk)C(O)OH, —($C_1$-$C_6$ haloalkyl), —O($C_1$-$C_6$ haloalkyl), —($C_0$-$C_6$ alkyl)heterocycloalk, —SO$_2$R, —($C_0$-$C_6$ alk)-C(O)-heterocycloalk, —($C_0$-$C_6$ alk)-C(O)-cycloalk, —($C_0$-$C_6$alk)-C(O)-heteroaryl, —($C_0$-$C_6$ alk)-C(O)-aryl, —($C_0$-$C_6$ alk)-C(O)O-heterocycloalk, —($C_0$-$C_6$ alk)-C(O)O-cycloalk, —($C_0$-$C_6$ alk)-C(O)O-heteroaryl, —($C_0$-$C_6$ alk)-C(O)O-aryl, —($C_0$-$C_6$ alk)-heterocycloalkyl, —($C_0$-$C_6$ alk)-heteroaryl, —($C_0$-$C_6$ alk)-aryl, and —($C_0$-$C_6$ alk)-cycloalk;

each Hca is a heterocycloalk group, optionally substituted with 1, 2 or 3 substituents independently selected from —R, —($C_1$-$C_6$ haloalkyl), —O($C_1$-$C_6$ haloalkyl), —($C_0$-$C_6$ alk)-C(O)OR, —($C_0$-$C_6$ alk)-C(O)R, =O, —OH, —CN, —($C_0$-$C_6$ alk)OR, —OCH$_2$CH$_2$—O—, —OCH$_2$O—, —SO$_2$R, —SO$_2$—($C_1$-$C_6$ haloalkyl), —($C_0$-$C_6$ alk)C(O)N$R^{19}{}_2$, —($C_0$-$C_6$ alk)-heterocycloalk, —($C_0$-$C_6$ alk)-aryl, —($C_0$-$C_6$ alk)-heterocycloalk, —($C_0$-$C_6$ alk)-cycloalk, —SO$_2$($C_0$-$C_6$ alk)-heterocycloalk, —SO$_2$($C_0$-$C_6$ alk)-aryl, —SO$_2$($C_0$-$C_6$ alk)-heteroaryl —SO$_2$($C_0$-$C_6$ alkyl)heteroaryl, —SO$_2$($C_0$-$C_6$ alk)-cycloalk;

each $R^{10}$ and $R^{11}$ is independently —H or —R;

each $R^{19}$ is independently selected from —H, —OH and —R in which any ($C_1$-$C_8$ alk) or —($C_1$-$C_8$ haloalkyl) groups are optionally substituted with 1, 2 or 3 substituents independently selected from =O, —($C_1$-$C_6$ alkoxy), —OH, or -halogen; —($C_1$-$C_6$ haloalkyl), wherein the —($C_1$-$C_6$ haloalkyl) may be substituted with from 1 to 6 halogens, —SO$_2$—($C_1$-$C_6$ alk), and —C(O)—($C_1$-$C_6$ alk);

each $R^{20}$ is a Hca or Het ring wherein that N from the —($C_0$-$C_6$ alk)C(O)N$R^{20}$ is a heteroatom in the Hca or Het ring, e.g., piperidine, piperizine and the like, the ring optionally substituted with 1 or 2 substituents independently selected from =O, —($C_1$-$C_6$ alkoxy), —OH, or -halogen; —($C_1$-$C_6$ haloalkyl), —SO$_2$—($C_1$-$C_6$ alk), and —C(O)—($C_1$-$C_6$ alk);

each R is independently —($C_1$-$C_8$ alk), —($C_3$-$C_8$ cycloalk), —($C_3$-$C_{12}$ heterocycloalk), —($C_1$-$C_8$ haloalkyl), or —($C_3$-$C_8$ halocycloalk), optionally substituted with 1, 2 or 3 substituents independently selected from —($C_1$-$C_6$ alkoxy), —($C_1$-$C_6$ hydroxyalkyoxy), —($C_1$-$C_6$ hydroxyalkyl), acetoxyalkyl, —C(O)O($C_1$-$C_6$ alkyl), —OH, =O, —N($C_1$-$C_6$ alkyl)$_2$, —NH($C_1$-$C_6$ alk), —NH$_2$, —OC(O)($C_0$-$C_6$ alk), —SO$_2$—($C_1$-$C_6$ alk), and —CO—($C_0$-$C_6$ alk); and each ($C_0$-$C_6$ alk), ($C_1$-$C_6$ alk), and —($C_1$-$C_8$ alk) is independently optionally substituted with 1, 2, 3 or 4 substituents selected independently from —($C_1$-$C_4$ alkyl), —($C_1$-$C_4$ alkoxy), —OH, =O, -halogen, —C(O)O($C_1$-$C_3$ alkyl) and —C(O)($C_1$-$C_3$ alkyl); and is optionally halogenated.

Another aspect of the invention relates to compounds and salts having the structure of Formula I, wherein $R^1$ and $R^2$ are independently —Cl, —F, —Br, —I or —H, with the proviso that at least one of $R^1$ and $R^2$ is —Cl, —F, —Br or —I;

$R^3$ is —$(C_0$-$C_6$ alk)C(O)$OR^e$, —$(C_0$-$C_6$ alk)C(O)$NR^a{}_2$, —$(C_0$-$C_6$ alk)C(O)$NR^aR^{19}$, —$(C_0$-$C_6$ alk)C(O)$NR^{19}{}_2$, —$(C_0$-$C_6$ alk)C(O)$NR^{20}$, —$(C_0$-$C_6$ alk)Ar, or —$(C_0$-$C_6$ alk)-O—$(C_0$-$C_6$ alk)Ar;

$R^4$ is —H, or —R;

each $R^5$, $R^6$ and $R^7$ is independently —R, —OR, —$NR^aR^{19}$, —$NO_2$, —Cl, —F, —Br, —I, —CN, —OH, —OOCR, —$(C_0$-$C_6$ alkyl)C(O)$OR^e$, $C_0$-$C_6$ alkyl)C(O)$N^aR^{19}$, or $C_0$-$C_6$ alkyl)C(O)$N^aR^{19}$; and w, x and y are independently 0, 1 or 2;

in which each $R^e$ is independently —H or —R, each $R^a$ is independently —H or —R, each $R^{19}$ is independently —H or —R, each Ar is independently phenyl optionally substituted with 1, 2 or 3 substituents selected from —R, —OR, —$NR_2$, —$NO_2$, —Cl, —F, —Br, —I, —CN, —OH, —C(O)OR, —($C_1$-$C_6$ haloalkyl) and —O($C_1$-$C_6$ haloalkyl), each R is independently —($C_1$-$C_8$ alkyl), —($C_3$-$C_8$ cycloalkyl), —($C_3$-$C_{12}$ heterocycloalk), —($C_1$-$C_8$ fluoroalkyl), —($C_3$-$C_8$ fluorocycloalk), —($C_1$-$C_8$ chloroalkyl), or —($C_3$-$C_8$ chlorocycloalk), wherein the —($C_1$-$C_6$ fluoroalkyl), —($C_3$-$C_8$ fluorocycloalk), —($C_1$-$C_6$ chloroalkyl), or —($C_3$-$C_8$ chlorocycloalk) may be substituted with from 1 to 6 fluorines or chlorines, respectively, each R optionally substituted with 1, 2 or 3 substituents selected from —($C_1$-$C_6$ alkoxy), —($C_1$-$C_8$ hydroxyalkyl), acetoxyalkyl, and —C(O)O($C_1$-$C_4$ alkyl).

In further desirable embodiments, R is independently —($C_1$-$C_8$ alkyl), —($C_3$-$C_8$ cycloalkyl), —($C_3$-$C_{12}$ heterocycloalk), —($C_1$-$C_8$ fluoroalkyl), —($C_3$-$C_8$ fluorocycloalk), —($C_1$-$C_8$ chloroalkyl), or —($C_3$-$C_8$ chlorocycloalk), wherein the —($C_1$-$C_6$ fluoroalkyl), —($C_3$-$C_8$ fluorocycloalk), —($C_1$-$C_6$ chloroalkyl), —($C_3$-$C_8$ chlorocycloalk) may be substituted with from 1 to 6 fluorines or chlorines, respectively, each R optionally substituted with 1, 2 or 3 substituents selected from —($C_1$-$C_6$ alkoxy), —($C_1$-$C_8$ hydroxyalkyl), acetoxyalkyl, and —C(O)O($C_1$-$C_4$ alkyl), with the proviso that at least one R is a —($C_3$-$C_{12}$ heterocycloalk).

Another aspect of the invention relates to compounds and salts having the structure of Formula I, wherein $R^1$ and $R^2$ are independently —Cl, —F, —Br, —I or —H, with the proviso that at least one of $R^1$ and $R^2$ is —Cl, —F, —Br or —I;

$R^3$ is —$(C_0$-$C_6$ alk)C(O)$OR^e$, —$(C_0$-$C_6$ alk)C(O)$NR^a{}_2$, —$(C_0$-$C_6$ alk)C(O)$NR^aR^{19}$, —$(C_0$-$C_6$ alk)C(O)$NR^{19}{}_2$, or —$(C_0$-$C_6$ alk)-C(O)$NR^{20}$;

$R^4$ is —H, or —R;

each $R^5$, $R^6$ and $R^7$ is independently —R, —OR, —$NR^aR^{19}$, —$NO_2$, —Cl, —F, —Br, —I, —CN, —OH, —OOCR, —($C_0$-$C_6$ alkyl)C(O)$OR^e$, $C_0$-$C_6$ alkyl)C(O)$N^aR^{19}$, or $C_0$-$C_6$ alkyl)C(O)$N^aR^{19}$; and w, x and y are independently 0, 1 or 2; 0 or 1; or 0.

Another aspect of the invention relates to compounds and salts having the structure of Formula I, wherein $R^1$ and $R^2$ are independently —Cl, —F, —Br, —I or —H, with the proviso that at least one of $R^1$ and $R^2$ is —Cl, —F, —Br or —I;

$R^3$ is —$(C_0$-$C_6$ alk)C(O)$OR^e$;

$R^4$ is —H, or —R;

each $R^5$, $R^6$ and $R^7$ is independently —R, —OR, —$NR^aR^{19}$, —$NO_2$, —Cl, —F, —Br, —I, —CN, —OH, —OOCR, —($C_0$-$C_6$ alkyl)C(O)$OR^e$, —($C_0$-$C_6$ alkyl)C(O)$N^aR^{19}$, or —$C_0$-$C_6$ alkyl)C(O)$N^aR^{19}$; and w, x and y are independently 0, 1 or 2; 0 or 1; or most preferably 0.

DEFINITIONS

Figure 1:
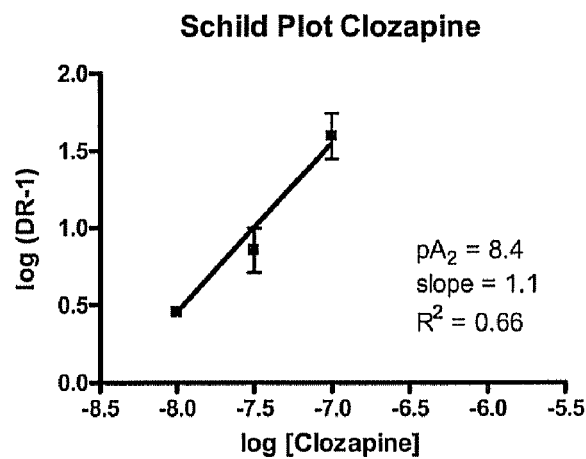
FIG. 1. Schild plot of 5-$HT_{2A}$ receptor antagonism of Compound K and Compound Q versus clozapine.
Figure 1:
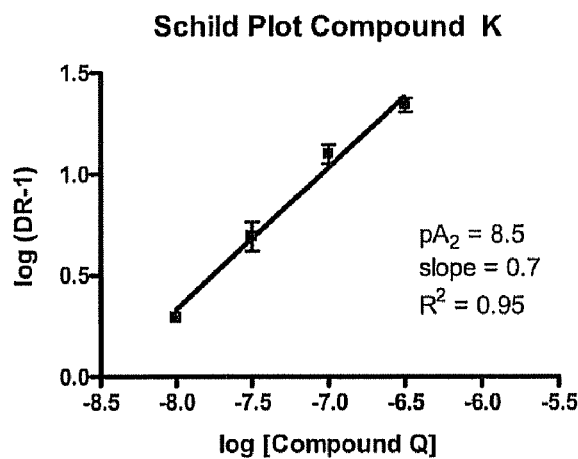
Figure 1:
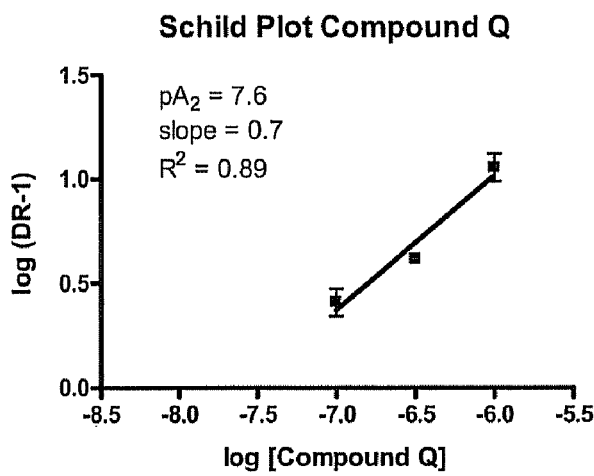

As used herein, the term "alk" includes alkyl, alkenyl, and alkynyl groups, both with all carbon chains or rings or including one or more heteroatoms, e.g., N, O, or S. The term "$C_m$-$C_n$ alk" means an alkyl, alkenyl or alkynyl group having between m and n carbon atoms, with the proviso that an alkenyl group or an alkynyl group must have at least two carbon atoms. For example, "$C_0$-$C_6$ alk" is an alkyl group having between zero and six carbon atoms, and alkenyl group having between two and six carbon atoms, or an alkynyl group having between two and six carbon atoms. Preferred alk groups are alkyl.

As used herein, the term "alkyl" includes alkyl groups of a designed number of carbon atoms, desirably between 1 and about 12 carbons. The term "$C_m$-$C_n$ alkyl" means an alkyl group having between m and n carbon atoms. For example, "$C_0$-$C_6$ alkyl" is an alkyl group having between zero and six carbon atoms. In the case of an alkyl group having zero carbon atoms (i.e., $C_0$), the group is simply a single covalent bond. Alkyl groups may be straight, or branched, and depending on context, may be a monovalent radical or a divalent radical (i.e., an alkylene group). For example, the moiety "—($C_0$-$C_6$ alkyl)-Ar" signifies connection of an aryl through a single bond or an alkylene bridge having between 1 and 6 carbons. Examples of "alkyl" include methyl, ethyl, propyl, isopropyl, butyl, iso-, sec- and tert-butyl, pentyl, hexyl, heptyl, 3-ethylbutyl, and the like. If the number of carbon atoms is not specified, the subject "alkyl" moiety has from 1 to 12 carbons.

As used herein, the term "alkenyl" includes alkenyl groups having at least 2 carbon atoms, desirably between 2 and about 12. Like alkyl groups, alkenyl groups may be straight, or branched, and depending on context, may be a monovalent radical or a divalent radical. There may be one or more double bonds, and they may be internal to the alkenyl (e.g., —$CH_2CH$=$CHCH_2$—), at a connecting end of the alkenyl (e.g., —CH=CHCH$(CH_3)_2$), or at a terminal end of the alkenyl (e.g., —$CH_2CH_2CH_2C$=CH). As used herein, "alkenyl" also refers to carbon chains that include one or more heteroatoms in place of one or more carbons, heteroatom being, for example, O, N, or S.

As used herein, the term "alkynyl" includes alkynyl groups having at least 2 carbon atoms, desirably between 2 and about 12. Like alkyl groups, alkynyl groups may be straight, or branched, and depending on context, may be a monovalent radical or a divalent radical. There may be one or more double bonds, and they may be internal to the alkynyl (e.g., —CH$_2$CH=CHCH$_2$—), at a connecting end of the alkynyl (e.g., —CH=CH—CH(CH$_3$)$_2$), or at a terminal end of the alkynyl (e.g., —CH$_2$CH$_2$CH$_2$C≡CH). As used herein, "alkynyl" also refers to carbon chains that include one or more heteroatoms in place of one or more carbons, heteroatom being, for example, O, N, or S.

The term "alkoxy" represents an alkyl group of indicated number of carbon atoms attached to the parent molecular moiety through an oxygen bridge. Examples of alkoxy groups include, for example, methoxy, ethoxy, n-propoxy and iso-propoxy.

The terms "haloalkyl" and "haloalkoxy" refer to an alkyl and alkoxy groups substituted with at least one halogen atom and optionally further substituted with at least one additional halogen atom, where each halogen is independently F, Cl, Br or I. Preferred halogens are F or Cl, while F is especially preferred. Preferred haloalkyl and haloalkoxy groups contain, for example 1-6 carbons, 1-4 carbons, or 1-2 carbons. Haloalkyl and haloalkoxy groups may be perhalogenated, such as in the case of —OCF$_3$ and —OCF$_2$CF$_3$. As used herein, "haloalkyl" also refers to carbon chains that include one or more heteroatoms in place of one or more carbons, heteroatom being, for example, O, N, or S.

The term "aryl" represents an aromatic carbocyclic group having a single ring (e.g., phenyl) that is optionally fused or otherwise attached to other aromatic hydrocarbon rings or non-aromatic hydrocarbon rings. "Aryl" includes multiple condensed rings in which at least one is aromatic, (e.g., 1,2,3,4-tetrahydronaphthyl, naphthyl), wherein each ring is optionally mono-, di-, or trisubstituted with the groups identified below, as well as multiple rings that are not fused, such as, for example, biphenyl or binaphthyl. Preferred aryl groups of the present invention are phenyl, 1-naphthyl, 2-naphthyl, indanyl, indenyl, dihydronaphthyl, fluorenyl, tetralinyl, 2,3-dihydrobenzofuranyl, or 6,7,8,9-tetrahydro-5H-benzo[a]cycloheptenyl. More preferably, the aryl group is a phenyl or naphthyl. Still more preferably, the aryl group is a phenyl.

The term "heteroaryl" refers to an aromatic ring system containing at least one heteroatom selected from nitrogen, oxygen, and sulfur. The heteroaryl ring may be fused or otherwise attached to one or more heteroaryl, aryl, cycloalk or heterocycloalk rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl, and imidazolyl, pyrazolyl, indazolyl, thiazolyl and benzothiazolyl.

The term "cycloalk" refers to an non-aromatic carbocyclic ring or ring system, which may be saturated (i.e., a "cycloalkyl"), or unsaturated (i.e., a "cycloalkenyl"). The cycloalk ring optionally fused to or otherwise attached to other cycloalk rings, heterocycloalk rings, aryl rings or heteroaryl rings. Preferred cycloalk groups have from 3 to 7 members. More preferred cycloalk groups have 5 or 6 members. Examples of cycloalk groups include, for example, cyclohexyl, cyclopentyl, cyclobutyl, cyclopropyl and tetrahydronaphthyl.

The term "heterocycloalk" refers to a non-aromatic ring or ring system containing at least one heteroatom that is preferably selected from nitrogen, oxygen, and sulfur, wherein said heteroatom is in a non-aromatic ring. The heterocycloalk may be saturated (i.e., a "heterocycloalkyl"), or unsaturated (i.e., a "heterocycloalkenyl"). The heterocycloalk ring is optionally fused to or otherwise attached to other heterocycloalk rings and/or non-aromatic hydrocarbon rings and/or phenyl rings. Preferred heterocycloalk groups have from 3 to 12 members. More preferred single heterocycloalk groups have 5 or 6 members; whereas most preferred heterocycloalk ring systems have from 10 to 12 members. Examples of heterocycloalk groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, pyrrolinyl, tetrahydropyranyl, piperidinyl, tetrahydrofuranyl, tetrahydrothienyl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalk groups include morpholinyl, tetrahydropyranyl, piperidinyl, aza-bicyclo[2.2.2]octyl, γ-butyrolactonyl (i.e., an oxo-substituted tetrahydrofuranyl), pyrrolidinyl, piperazinyl, thiomorpholinyl, thiomorpholinyl S,S-dioxide, 2-oxazolidonyl, imidazolidonyl, isoindolindionyl, piperazinonyl, and mono- and di-saccharide sugars, e.g., glucose, fructose, sucrose, mannose, arabinose, and galactose.

The term "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. Preferred acid addition salts are the chloride and sulfate salts and the salts of di- and tri-carboxylic acids, for example, tartrate, citrate, maleate, succinate, and the like.

DETAILED DESCRIPTION OF EMBODIMENTS OF THE INVENTION

One aspect of the invention relates to compounds having a structure according to Formula (I)

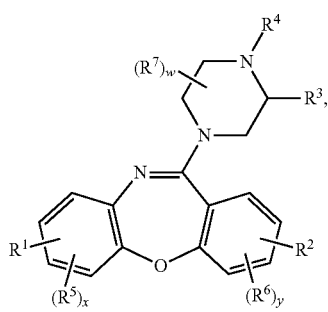

(I)

and pharmaceutically acceptable salts thereof.

The structure of Formula (I) is based on a dibenzo[b,f][1,4]oxazapine core having the numbering system shown below in Formula (II).

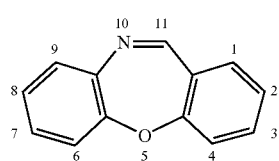

(II)

$R^1$ is attached at any one of the 6-9 positions of the dibenzo[b,f][1,4]oxazapine, while $R^2$ is attached at any of the 1-4 positions. $R^1$ and $R^2$ are independently —Cl, —F, —Br, —I or —H. Desirably, $R^1$ is attached at the 7 or 8 position of the dibenzo[b,f][1,4]oxazapine. Similarly, $R_2$ is desirably attached at the 2 or 3 position of the dibenzo[b,f][1,4]oxazapine. According to a desirable embodiment of the invention, at least one of $R^1$ and $R^2$ is —F, —Cl, —Br or —I. More desirably, only one of $R^1$ and $R^2$ is —F, —Cl, —Br or —I, and the other is —H.

The piperazine is substituted with $R^3$ at a carbon distal from the dibenzo[b,f][1,4]oxazapine, as shown in Formula (I). $R^3$ may be —R (nonoptionally substituted in this instance at $R^3$), —$(C_0$-$C_6$ alk)C(O)OR$^e$, —$(C_0$-$C_6$ alk)C(O)NR$^a{}_2$, —$(C_0$-$C_6$ alk)C(O)NR$^a$R$^{19}$, —$(C_0$-$C_6$ alk)C(O)NR$^{19}{}_2$, —$(C_0$-$C_6$ alk)C(O)NR$^{20}$, —$(C_0$-$C_6$ alk)Ar, —$(C_1$-$C_6$ alk)-O—$(C_0$-$C_6$ alk)Ar, —$(C_0$-$C_6$ alk)-OR, —$(C_0$-$C_6$ alk)C(O)R$^k$, or —$(C_0$-$C_6$ alk)-NR$^a$R$^{19}$, in which in which R, Re, Ra, R19, Ar, Het, Hca, Cak are as described below. Each alk group may be, for example, an alkyl group. In desirable embodiments of the invention, $R^3$ is —$(C_0$-$C_6$ alk)C(O)OR$^e$, —$(C_0$-$C_6$ alk)C(O)NR$^a{}_2$, —$(C_0$-$C_6$ alk)C(O)NR$^a$R$^{19}$, —$(C_0$-$C_6$ alk)C(O)NR$^{19}{}_2$, —$(C_0$-$C_6$ alk)C(O)NR$^{20}$, —$(C_0$-$C_6$ alk)Ar, or —$(C_0$-$C_6$ alk)-O—$(C_0$-$C_6$ alk)Ar. In other desirable embodiments of the invention, $R^3$ is —$(C_0$-$C_6$ alk)C(O)OR$^e$, —$(C_0$-$C_6$ alk)C(O)NR$^a{}_2$, —$(C_0$-$C_6$ alk)C(O)NR$^a$R$^{19}$, —$(C_0$-$C_6$ alk)C(O)NR$^{19}{}_2$, or —$(C_0$-$C_6$ alk)-C(O)NR$^{20}$. In further desirable embodiments of the invention, $R^3$ is —$(C_0$-$C_6$ alk)C(O)OR$^e$. In yet further desirable embodiments of the invention, $R^3$ is —$(C_0$-$C_6$ alk)C(O)OR$^e$ in which the —$(C_0$-$C_6$ alk) is —$(C_1$-$C_6$ alk), —$(C_1$-$C_4$ alk) or —$(C_1$-$C_2$ alk).

Other desirable R substituents have gem-, mono-, or dialkyl substitution alpha to a functional group, e.g., a carbonyl carbon. Accordingly, in certain desirable embodiments of the invention, each $(C_0$-$C_6$ alkyl) connected directly to the piperazine ring as part of $R^3$ is a —$(C_0$-$C_5$ alkyl)C$(C_1$-$C_3$ alkyl)$_2$-, in which $(C_0$-$C_5$ alkyl) is independently optionally substituted with 1 or 2 substituents selected independently from —$(C_1$-$C_4$ alkyl), —$(C_1$-$C_4$ alkoxy), —OH, =O, -halogen, —C(O)O$(C_1$-$C_3$ alkyl) and —C(O)$(C_1$-$C_3$ alkyl); and is optionally halogenated.

In certain especially desirable embodiments of the invention, $R^3$ is —$(C_0$-$C_6$ alk)C(O)OR$^e$, —$(C_0$-$C_6$ alk)C(O)NR$^a{}_2$, —$(C_0$-$C_6$ alk)C(O)NR$^a$R$^{19}$, —$(C_0$-$C_6$ alk)C(O)NR$^{19}{}_2$, or —$(C_0$-$C_6$ alk)-C(O)NR$^{20}$. In yet other desirable embodiments of the invention, $R^3$ is —$(C_0$-$C_6$ alk)C(O)OR$^e$. In these embodiments, each $C_0$—$C_6$ alkyl connected directly to the piperazine ring as part of $R^3$ may be, for example, $C_2$-$C_6$ alkyl, or alternatively $C_1$-$C_2$ alkyl. In certain embodiments of the invention $R^3$ is —$(C_0$-$C_5$ alkyl)C$(C_1$-$C_3$ alkyl)$_2$C(O)OR$^e$, —$(C_0$-$C_5$ alkyl)C$(C_1$-$C_3$ alkyl)$_2$C(O)NR$^a{}_2$, —$(C_0$-$C_5$ alkyl)C$(C_1$-$C_3$ alkyl)$_2$C(O)NR$^a$R$^{19}$, —$(C_0$-$C_5$ alkyl)C$(C_1$-$C_3$ alkyl)$_2$C(O)NR$^{19}{}_2$, —$(C_0$-$C_5$ alkyl)C$(C_1$-$C_3$ alkyl)$_2$C(O)NR$^{20}$, —$(C_1$-$C_5$ alkyl)C$(C_1$-$C_3$ alkyl)$_2$Ar, —$(C_0$-$C_6$ alk)-O—$(C_0$-$C_5$ alkyl)C$(C_1$-$C_3$ alkyl)$_2$Ar, —$(C_0$-$C_5$ alkyl)C$(C_1$-$C_3$ alkyl)$_2$CR, —$(C_0$-$C_5$ alkyl)C$(C_1$-$C_3$ alkyl)$_2$C(O)R$^k$, or —$(C_0$-$C_5$ alkyl)C$(C_1$-$C_3$ alkyl)$_2$NR$^a$R$^{19}$. Finally, in these embodiments of the invention, each $R^5$, $R^6$ and $R^7$ is desirably independently —R, —OR, —NR$^{19}{}_2$, —NO$_2$, —Cl, —F, —Br, —I, —CN, —OH, —OOCR, —$(C_0$-$C_2$ alkyl)C(O)OR, or —$(C_0$-$C_2$ alkyl)C(O)NR$^{19}{}_2$.

The $R^3$ group will form a stereogenic center on the piperazine ring. The $R^3$ group may be attached to the piperazine ring in an S configuration, or an R configuration. The compound or salt may exist as a racemic mixture, a scalemic mixture, or an enantomerically- or diastereomerically-enriched mixture having at least about 80% enantiomeric or diastereomeric excess at the carbon of attachment of the $R^3$ group to the piperazine.

The piperazine is substituted with $R^4$ at the nitrogen distal from the dibenzo[b,f][1,4]oxazapine, as shown in Formula (I). $R^4$ may be, for example, —H or —R. In certain especially desirable embodiments of the invention, $R^4$ is H.

The benzo moieties of the dibenzo[b,f][1,4]oxazapine core may be substituted with substituents other than $R^1$ and $R^2$. For example, as shown in Formula (I), the 6-9 positions of the dibenzo[b,f][1,4]oxazapine may be substituted with 0, 1, 2 or 3 $R^5$ substituents (i.e., x is 0, 1, 2 or 3). Similarly, the 1-4 positions may be substituted with 0, 1, 2 or 3 $R^6$ substituents (i.e., y is 0, 1, 2 or 3). The $R^5$ and $R^6$ substituents are independently —R, —$(C_0$-$C_6$ alk)-OR, —$(C_0$-$C_6$ alk)-NR$^a$R$^{19}$, —NO$_2$, -halogen, —CN, —OH, —OOCR, —$(C_0$-$C_6$ alk)COOR$^e$, —$(C_0$-$C_6$ alk)C(O)NR$^a$R$^{19}$, —$(C_0$-$C_6$ alk)Ar, —$(C_0$-$C_6$ alk)-O—$(C_0$-$C_6$ alk)Ar, —$(C_0$-$C_6$ alk)Het, —$(C_0$-$C_6$ alk)-O—$(C_0$-$C_6$ alk)Het, —$(C_0$-$C_6$ alk)Hca, —$(C_0$-$C_6$ alk)-O—$(C_0$-$C_6$ alk)Hca, —$(C_0$-$C_6$ alk)Cak, —$(C_0$-$C_6$ alk)-O—$(C_0$-$C_6$ alk)Cak, —$(C_0$-$C_6$ alk)C(O)Hca, —$(C_0$-$C_6$ alk)C(O)Ar, —$(C_0$-$C_6$ alk)C(O)Het, or —$(C_0$-$C_6$ alk)C(O)Cak, in which R, R$^a$, R$^{19}$, Ar, Het, Hca, Cak are as described below. Each alk group may be, for example, an alkyl group. Especially desirable $R^5$ and $R^6$ substituents include —R, —OR, —NR$^{19}{}_2$, —NO$_2$, —Cl, —F, —Br, —I, —CN, —OH, —OOCR, —$(C_0$-$C_2$ alkyl)C(O)OR, and —$(C_0$-$C_2$ alkyl)C (O)NR$^{19}$$_2$. Desirably, the dibenzo[b,f][1,4]oxazapine is substituted with 0 or 1 R$^5$ substituents (i.e., x is 0 or 1). Similarly, the dibenzo[b,f][1,4]oxazapine is desirably substituted with 0 or 1 R$^6$ substituents (i.e., y is 0 or 1). In certain desirable embodiments of the invention, the dibenzo[b,f][1,4]oxazapine is substituted with no R$^5$ or R$^6$ groups (i.e., both x and y are 0).

Similarly, the piperazine ring of the structure of Formula (I) may be substituted with substituents other than R$^3$ and R$^4$. For example, as shown in Formula (I), the piperazine ring may be substituted with 0, 1, 2 or 3 R$^7$ substituents (i.e., w is 0, 1, 2 or 3). The R$^7$ substituents are independently —R, —(C$_0$-C$_6$ alk)-OR, —(C$_0$-C$_6$ alk)-NR$^a$R$^{19}$, —NO$_2$, -halogen, —CN, —OH, —OOCR, —(C$_0$-C$_6$ alk)COOR$^e$, —(C$_0$-C$_6$ alk)C(O)NR$^a$R$^{19}$, —(C$_0$-C$_6$ alk)Ar, —(C$_0$-C$_6$ alk)-O—(C$_0$-C$_6$ alk)Ar, —(C$_0$-C$_6$ alk)Het, —(C$_0$-C$_6$ alk)-O—(C$_0$-C$_6$ alk)Het, —(C$_0$-C$_6$ alk)Hca, —(C$_0$-C$_6$ alk)-O—(C$_0$-C$_6$ alk)Hca, —(C$_0$-C$_6$ alk)Cak, —(C$_0$-C$_6$ alk)-O—(C$_0$-C$_6$ alk)Cak, —(C$_0$-C$_6$ alk)C(O)Hca, —(C$_0$-C$_6$ alk)C(O)Ar, —(C$_0$-C$_6$ alk)C(O)Het, or —(C$_0$-C$_6$ alk)C(O)Cak, in which R, R$^a$, R$^{19}$, Ar, Het, Hca, Cak are as described below. Each alk group may be, for example, an alkyl group. Especially desirable R$^7$ substituents include —R, —OR, —NR$^{19}$$_2$, —NO$_2$, —Cl, —F, —Br, —I, —CN, —OH, —OOCR, —(C$_0$-C$_2$ alkyl)C(O)OR, and —(C$_0$-C$_2$ alkyl)C(O)NR$^{19}$$_2$. Desirably, the piperazine is substituted with 0 or 1 R$^7$ substituents (i.e., w is 0 or 1). In certain desirable embodiments of the invention, the piperazine is substituted with no R$^7$ groups. In certain especially desirable embodiments of the invention, the 11-piperazin-1-yl dibenzo[b,f][1,4]oxazapine core is substituted with no R$^5$, R$^6$ or R$^7$ groups (i.e., w, x and y are each zero). In other desirable embodiments, w, x, and y are each zero and R$^4$ is —H.

In the compounds according to this aspect of the invention, each R$^e$ may independently be —H, —R, —(C$_1$-C$_6$ alk)C(O)Hca, —(C$_1$-C$_6$ alk)C(O)Cak, —(C$_1$-C$_6$ alk)C(O)Het, —(C$_1$-C$_6$ alk)C(O)Ar, —(C$_1$-C$_6$ alk)C(O)O-Hca, —(C$_1$-C$_6$ alk)C(O)O-Cak, —(C$_1$-C$_6$ alk)C(O)O-Het, —(C$_1$-C$_6$ alk)C(O)O—Ar, —(C$_0$-C$_6$ alk) Hca, —(C$_0$-C$_6$ alk) Het, —(C$_0$-C$_6$ alk) Ar, —(C$_0$-C$_6$ alk)Cak, —(C$_1$-C$_6$ alk)C(O)OR, —(C$_1$-C$_6$ alk)C(O)NR$^{19}$$_2$, —(C$_0$-C$_6$ alk)-OR, or —(C$_0$-C$_6$ alk)-OH, in which R, R$^{19}$, Ar, Het, Hca, Cak are as described below Each alk group may be, for example, an alkyl group. Desirably, each R$^e$ is independently —H or —R.

In the compounds according to this aspect of the invention, each R$^a$ may independently be —H, —R, —(C$_1$-C$_6$ alk)-OR, —(C$_1$-C$_6$ alk)-OH, —(C$_0$-C$_6$ alk)C(O)OR, —(C$_1$-C$_6$ alk)-NR$^{19}$$_2$, —(C$_0$-C$_6$ alk)Hca, —(C$_0$-C$_6$ alk)Ar, —(C$_0$-C$_6$ alk)Het, or —(C$_0$-C$_6$ alk)Cak, in which R, R19, Hca, Ar, Het and Cak are as described below. Each alk group may be, for example, an alkyl group. Desirably, each R$^a$ is independently —H or —R.

In the compounds according to this aspect of the invention, each R$^k$ may independently be —H, —R, —(C$_1$-C$_6$ alk)C(O)Hca, —(C$_1$-C$_6$ alk)C(O)Cak, —(C$_1$-C$_6$ alk)C(O)Het, —(C$_1$-C$_6$ alk)C(O)Ar, —(C$_1$-C$_6$ alk)Hca, —(C$_0$-C$_6$ alk)Het, —(C$_0$-C$_6$ alk)Ar, —(C$_0$-C$_6$ alk)Cak, —(C$_1$-C$_6$ alk)C(O)OR, or —(C$_1$-C$_6$ alk)C(O)NR$^{19}$$_2$, in which R, Hca, Cak, Het, Ar and R$^{19}$ are as described below. Each alk group may be, for example, an alkyl group.

In the compounds according to this aspect of the invention, each Cak is a cycloalk group, optionally substituted with 1, 2 or 3 substituents independently selected from —R, —(C$_0$-C$_6$ alk)C(O)OR, =O, —OH, —CN, —(C$_0$-C$_6$ alk)OR, —OCH$_2$CH$_2$—O—, —OCH$_2$O—, —SO$_2$R, —SO$_2$—(C$_1$-C$_6$ haloalkyl), —(C$_0$-C$_6$ alk)C(O)NR$^{19}$$_2$, —(C$_0$-C$_6$ alk) Het, —SO$_2$(C$_0$-C$_6$ alk)-Hca, —(C$_0$-C$_6$ alk)Ar, —(C$_0$-C$_6$ alk) Het, —(C$_0$-C$_6$ alk)Hca, —(C$_0$-C$_6$ alk)C(O)R, —SO$_2$(C$_0$-C$_6$ alk)Ar, —SO$_2$(C$_0$-C$_6$ alk)Het, and —SO$_2$(C$_0$-C$_6$ alk)cycloalk, in which R, R$^{19}$, Het, Hca and Ar are as described below. Each alk group may be, for example, an alkyl group. Each cycloalk group may be, for example, a cycloalkyl group. Desirably, Cak is a cycloalkyl group. In certain desirable embodiments of the invention, each Cak is optionally substituted cyclohexyl, cyclopentyl, cyclobutyl or cyclopropyl.

In the compounds according to this aspect of the invention, each Ar is an aryl group, optionally substituted with 1, 2 or 3 substituents independently selected from —R, —OR, —(C$_0$-C$_6$ alk)NR$^{19}$$_2$, —NO$_2$, —Cl, —F, —Br, —I, —CN, —(C$_0$-C$_6$ alk)OH, —(C$_0$-C$_6$ alk)C(O)OR, —(C$_0$-C$_6$ alk)C(O)OH, —(C$_1$-C$_6$ haloalkyl), —O(C$_1$-C$_6$ haloalkyl), —(C$_0$-C$_6$ alkyl)heterocycloalk, —SO$_2$R, —(C$_0$-C$_6$ alk)-C)(O)-heterocycloalk, —(C$_0$-C$_6$ alk)-C(O)-cycloalk, —(C$_0$-C$_6$ alkyl)-C(O)-heteroaryl, —(C$_0$-C$_6$ alk)-C(O)-aryl, —(C$_0$-C$_6$ alkyl)-C(O)O-heterocycloalk, —(C$_0$-C$_6$ alk)-C(O)O-cycloalk, —(C$_0$-C$_6$ alkyl)-C(O)O-heteroaryl, —(C$_0$-C$_6$ alk)-C(O)O-aryl, —(C$_0$-C$_6$ alk)-heterocycloalkyl, —(C$_0$-C$_6$ alk)-heteroaryl, —(C$_0$-C$_6$ alk)-aryl, and —(C$_0$-C$_6$ alk)-cycloalk, in which R and R$^{19}$ are as described below. Each alk group may be, for example, an alkyl group. Each cycloalk group may be, for example, a cycloalkyl group. Each heterocycloalk group may be, for example, a heterocycloalkyl group. In certain desirable embodiments of the invention, each Ar is phenyl optionally independently substituted with 1, 2 or 3 substituents selected from —R, —OR, —NR$_2$, —NO$_2$, —Cl, —F, —Br, —I, —CN, —OH and —C(O)OR.

In the compounds according to this aspect of the invention, each Het is a heteroaryl group, optionally substituted with 1, 2 or 3 groups independently selected from —R, —OR, —(C$_0$-C$_6$ alk)NR$^{19}$$_2$, —NO$_2$, —Cl, —F, —Br, —I, —CN, —(C$_0$-C$_6$ alk)OH, —(C$_0$-C$_6$ alk)CO$_2$R, —(C$_0$-C$_6$ alk)C(O)OH, —(C$_1$-C$_6$ haloalkyl), —O(C$_1$-C$_6$ haloalkyl), —(C$_0$-C$_6$ alkyl)heterocycloalk, —SO$_2$R, —(C$_0$-C$_6$ alk)-C(O)-heterocycloalk, —(C$_0$-C$_6$ alk)-C(O)-cycloalk, —(C$_0$-C$_6$ alk)-C(O)-heteroaryl, —(C$_0$-C$_6$ alk)-C(O)-aryl, —(C$_0$-C$_6$ alk)-C(O)O-heterocycloalk, —(C$_0$-C$_6$ alk)-C(O)O-cycloalk, —(C$_0$-C$_6$ alk)-C(O)O-heteroaryl, —(C$_0$-C$_6$ alk)-C(O)O-aryl, —(C$_0$-C$_6$ alk)-heterocycloalkyl, —(C$_0$-C$_6$ alk)-heteroaryl, —(C$_0$-C$_6$ alk)-aryl, and —(C$_0$-C$_6$ alk)-cycloalk, in which R and R$^{19}$ are described below. Each alk group may be, for example, an alkyl group. Each cycloalk group may be, for example, a cycloalkyl group. Each heterocycloalk group may be, for example, a heterocycloalkyl group. In certain desirable embodiments of the invention, each Het is optionally substituted pyridyl, pyrimidyl, quinolinyl, indolyl, pyrrolyl, furanyl, thienyl, and imidazolyl, pyrazolyl, indazolyl, thiazolyl or benzothiazolyl.

In the compounds according to this aspect of the invention, each Hca is a heterocycloalk group, optionally substituted with 1, 2 or 3 substituents independently selected from —R, —(C$_1$-C$_6$ haloalkyl), —O(C$_1$-C$_6$ haloalkyl), —(C$_0$-C$_6$ alk)-C(O)OR, —(C$_0$-C$_6$ alk)-C(O)R, =O, —OH, —CN, —(C$_0$-C$_6$ alk)OR, —OCH$_2$CH$_2$—O—, —OCH$_2$O—, —SO$_2$R, —SO$_2$—(C$_1$-C$_6$ haloalkyl), —(C$_0$-C$_6$ alk)C(O)NR$^{19}$$_2$, —(C$_0$-C$_6$ alk)-heterocycloalk, —(C$_0$-C$_6$ alk)-aryl, —(C$_0$-C$_6$ alk)-heterocycloalk, —(C$_0$-C$_6$ alk)-cycloalk, —SO$_2$(C$_0$-C$_6$ alk)-heterocycloalk, —SO$_2$(C$_0$-C$_6$ alk)-aryl, —SO$_2$(C$_0$-C$_6$ alk)-heteroaryl —SO$_2$(C$_0$-C$_6$ alkyl)heteroaryl, —SO$_2$(C$_0$-C$_6$ alk)-cycloalk, in which R and R$^{19}$ are as described below. Each alk group may be, for example, an alkyl group. Each cycloalk group may be, for example, a cycloalkyl group. Each heterocycloalk group may be, for example, a heterocycloalkyl group. In certain desirable embodiments of the invention, Hca is optionally substituted morpholinyl, tetrahydropyranyl, piperidinyl, aza-bicyclo[2.2.2]octyl, γ-butryolactonyl, pyrrolidinyl, piperazinyl, thiomorpholinyl, thiomorpholinyl S,S-dioxide, 2-oxazolidonyl, imidazolidonyl, isoindolindionyl, piperazinonyl.

In the compounds according to this aspect of the invention, each $R^{10}$ and $R^{11}$ is independently —H or —R, in which —R is as described below.

In the compounds according to this aspect of the invention, each $R^{19}$ is independently selected from —H, —OH and —R, in which R is as described below. Each alk group may be, for example, an alkyl group.

In the compounds according to this aspect of the invention, each $R^{20}$ is a Hca or Het ring wherein that N from the —($C_0$-$C_6$ alk)C(O)$NR^{20}$, is a heteroatom in the Hca or Het ring, the ring optionally substituted with 1 or 2 substituents independently selected from =O, —($C_1$-$C_6$ alkoxy), —OH, or -halogen; —($C_1$-$C_6$ haloalkyl), —$SO_2$—($C_1$-$C_6$ alk), and —C(O)—($C_1$-$C_6$ alk).

In the compounds according to this aspect of the invention, each R is independently —($C_1$-$C_8$ alk), —($C_3$-$C_8$ cycloalk), —($C_3$-$C_{12}$ heterocycloalk), —($C_1$-$C_8$ haloalkyl), or —($C_3$-$C_8$ halocycloalk), optionally substituted with 1, 2 or 3 substituents independently selected from —($C_1$-$C_6$ alkoxy), —($C_1$-$C_6$ hydroxyalkyoxy), —($C_1$-$C_6$ hydroxyalkyl), acetoxyalkyl, —C(O)O($C_1$-$C_6$ alkyl), —OH, =O, —N($C_1$-$C_6$ alkyl)$_2$, —NH($C_1$-$C_6$ alk), —$NH_2$, —OC(O)($C_0$-$C_6$ alk), —$SO_2$-($C_1$-$C_6$ alk), and —CO—($C_0$-$C_6$ alk). Each —($C_1$-$C_8$ haloalkyl) or —($C_3$-$C_8$ halocycloalk), may be further optionally substituted with from 1 to 6 additional halogens. Each alk group may be, for example, an alkyl group.

In the compounds according to this aspect of the invention, each ($C_0$-$C_6$ alk), ($C_1$-$C_6$ alk), and —($C_1$-$C_8$ alk) is independently optionally substituted with 1, 2, 3 or 4 substituents selected independently from —($C_1$-$C_4$ alkyl), —($C_1$-$C_4$ alkoxy), —OH, =O, -halogen, —C(O)O($C_1$-$C_3$ alkyl) and —C(O)($C_1$-$C_3$ alkyl); and is optionally halogenated. Each alk group may be, for example, an alkyl group.

In this aspect of the invention, one or more of the alk groups may be alkenyl groups or alkynyl groups. In certain embodiments of the invention, at least one of the alk groups is an alkenyl group or an alkynyl group. Alternatively, in certain desirable embodiments of the invention, all of the alk groups are alkyl groups.

Another aspect of the invention relates to compounds of Formula (I) and pharmaceutically acceptable salts thereof, in which $R^1$ and $R^2$ are independently —Cl, —F, —Br, —I or —H, with the proviso that at least one of $R^1$ and $R^2$ is —Cl, —F, —Br or —I; $R^3$ is —($C_0$-$C_6$ alk)C(O)$OR^e$, —($C_0$-$C_6$ alk)C(O)$NR^a{}_2$, —($C_0$-$C_6$ alk)C(O)$NR^aR^{19}$, —($C_0$-$C_6$ alk)C(O)$NR^{19}{}_2$, —($C_0$-$C_6$ alk)-C(O)$NR^{10}$, —($C_0$-$C_6$ alk)Ar, or —($C_0$-$C_6$ alk)-O—($C_0$-$C_6$ alk)Ar; $R^4$ is —H or —R; each $R^5$, $R^6$ and $R^7$ is independently —R, —OR, —$NR^aR^{19}$, —$NO_2$, —Cl, —F, —Br, —I, —CN, —OH, —OOCR, —($C_0$-$C_6$ alkyl)C(O)$OR^e$, —($C_0$-$C_6$ alkyl)C(O)$NR^aR^{19}$, or —($C_0$-$C_6$ alkyl)C(O)$NR^aR^{19}$; and w, x and y are independently 0, 1 or 2, in which each $R^e$ is independently —H or —R, each $R^a$ is independently —H or —R, each $R^{19}$ is independently —H or —R, each Ar is phenyl independently optionally substituted with 1, 2 or 3 substituents selected from —R, —OR, —$NR_2$, —$NO_2$, —Cl, —F, —Br, —I, —CN, —OH, —C(O)OR, —($C_1$-$C_6$ haloalkyl) and —O($C_1$-$C_6$ haloalkyl), and each R is independently —($C_1$-$C_8$ alkyl), —($C_3$-$C_8$ cycloalkyl), —($C_3$-$C_{12}$ heterocycloalk), —($C_1$-$C_8$ fluoroalkyl), —($C_3$-$C_8$ fluorocycloalk), —($C_1$-$C_8$ chloroalkyl), or —($C_3$-$C_8$ chlorocycloalk), wherein the —($C_1$-$C_6$ fluoroalkyl), —($C_3$-$C_8$ fluorocycloalk), —($C_1$-$C_6$ chloroalkyl), or —($C_3$-$C_8$ chlorocycloalk) may be substituted with from 1 to 6 fluorines or chlorines, respectively, each R optionally substituted with 1, 2 or 3 substituents selected from —($C_1$-$C_6$ alkoxy), —($C_1$-$C_8$ hydroxyalkyl), acetoxyalkyl, and —C(O)O($C_1$-$C_4$ alkyl).

In desirable compounds according to this aspect of the invention, only one of $R^1$ and $R^2$ is —Cl, —F, —Br or —I, and the other is H. For example, one of $R^1$ or $R^2$ may be Cl, and the other may be —H. $R^1$ is desirably attached at the 7 or 8 position of the dibenzo[b,f][1,4]oxazapine, and $R^2$ is desirably attached at its 2 or 3 position.

In desirable compounds according to this aspect of the invention, $R^3$ is —($C_0$-$C_6$ alk)C(O)$OR^e$, —($C_0$-$C_6$ alk)C(O)$NR^a{}_2$, —($C_0$-$C_6$ alk)C(O)$NR^aR^{19}$, —($C_0$-$C_6$ alk)C(O)$NR^{19}{}_2$, or —($C_0$-$C_6$ alk)-C(O)$NR^{20}$. More desirably, $R^3$ is —($CH_2$)$_p$$CO_2R^e$, —($CH_2$)$_p$$CONR^a{}_2$, —($CH_2$)$_p$C(O)$NR^aR^{19}$, —($CH_2$)$_p$ C(O)$NR^{20}$, or —($CH_2$)$_p$$CONR^{19}{}_2$ in which p is 0, 1, 2, 3, 4, 5 or 6. For example, p may be 1 or 2. In yet other desirable embodiments of the invention, $R^3$ is —($CH_2$)$_p$$CO_2R^e$, —($CH_2$)$_p$$CONR^a{}_2$, —($CH_2$)$_p$C(O)$NR^aR^{19}$. In certain desirable embodiments of the invention, the R3 group has gem-mono- or dialkyl substitution alpha to its functional group. As such, each ($C_0$-$C_6$ alkyl) connected directly to the piperazine ring as part of $R^3$ is desirably a —($C_0$-$C_5$ alkyl)C($C_1$-$C_3$ alkyl)$_2$-group. For example, $R^3$ may be —($C_0$-$C_5$ alkyl)C($C_1$-$C_3$ alkyl)$_2$C(O)$OR^e$, —($C_0$-$C_5$ alkyl)C($C_1$-$C_3$ alkyl)$_2$C(O)$NR^d{}_2$, —($C_0$-$C_5$ alkyl)C($C_1$-$C_3$ alkyl)$_2$C(O)$NR^aR^{19}$, —($C_0$-$C_5$ alkyl)C($C_1$-$C_3$ alkyl)$_2$C(O)$NR^{19}{}_2$, —($C_0$-$C_5$ alkyl)C($C_1$-$C_3$ alkyl)$_2$C(O)$NR^{20}$, —($CH_2$)$_q$$CR^d{}_2$$CO_2R^e$, —($CH_2$)$_q$$CR^d{}_2$$CONR^a{}_2$, —($CH_2$)$_q$$CR^d{}_2$$CONR^{19}{}_2$, —($CH_2$)$_q$ $CR^d{}_2$$CONR^aR^{19}$, or —($CH_2$)$_q$$CR^d{}_2$$CONR^{20}$, wherein q is 0, 1, 2, 3, 4 or 5, and each $R^d$ is individually -Me, -Et or -Pr. q is desirably 0, 1 or 2. In especially desirable embodiments of the invention, $R^3$ is —($C_0$-$C_6$ alkyl)C(O)$OR^e$. $R^e$ may be, for example, —H, -Me, -Et, —Pr or —Bu. In further especially desirable embodiments of the invention, $R^3$ is —($C_0$-$C_3$ alkyl)C(O)$OR^e$, wherein $R^e$ may be, for example, —H, -Me, -Et, —Pr or —Bu. In yet further especially desirable embodiments of the invention, $R^3$ is —($C_1$-$C_2$ alkyl)C(O)$OR^e$, wherein $R^e$ may be, for example, —H, -Me, -Et, —Pr or —Bu. In other desirable embodiments of the invention, $R^3$ is —($C_0$-$C_6$ alkyl)C(O)NHR, —($C_0$-$C_3$ alkyl)C(O)NHR, or —($C_1$-$C_2$ alkyl)C(O)NHR, wherein $R^a$ may be, for example, —H, -Me, -Et, —Pr or —Bu.

In this aspect of the invention, The $R^3$ group may be attached to the piperazine ring in an S configuration, or an R configuration. The compound or salt may exist as a racemic mixture, a scalemic mixture, or an enantomerically- or diastereomerically-enriched mixture having at least about 80% enantiomeric or diastereomeric excess at the carbon of attachment of the $R^3$ group to the piperazine.

In certain embodiments according to this aspect of the invention, $R^4$ is —H. In other desirable embodiments, w, x and y are each zero.

In other preferred embodiments, the alk groups are alkyl.

Another aspect of the invention relates to a compound having the structure of Formula

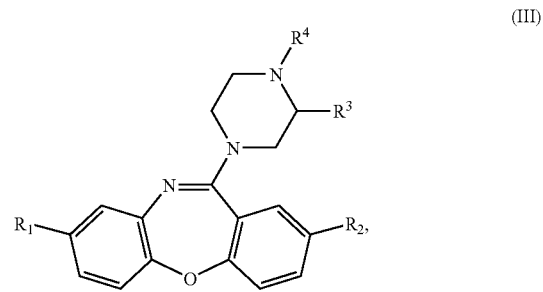

(III)

and pharmaceutically acceptable salts thereof.

The structure of Formula (III) is also based on a dibenzo[b,f][1,4]oxazapine core having the numbering system shown above in Formula (II).

In embodiments of this aspect of the invention, $R^1$ is attached at the 8 position of the dibenzo[b,f][1,4]oxazapine, while $R^2$ is attached at the 2 position. $R^1$ and $R^2$ are independently —Cl, —F, —Br, —I or —H. According to a desirable embodiment of the invention, at least one of $R^1$ and $R^2$ is —F, —Cl, —Br or —I. More desirably, only one of $R^1$ and $R^2$ is —F, —Cl, —Br or —I, and the other is —H.

The piperazine is substituted with $R^3$ at a carbon distal from the dibenzo[b,f][1,4]oxazapine, as shown in Formula (III), or the 3' position. $R^3$ may be —R (nonoptionally substituted in this instance at $R^3$), —$(C_0$-$C_6$ alk)$C(O)OR^e$, —$(C_0$-$C_6$ alk)$C(O)NR_{12}$, —$(C_0$-$C_6$ alk)$C(O)NR^aR^{19}$, —$(C_0$-$C_6$ alk)$C(O)NR^{19}{}_2$, —$(C_0$-$C_6$ alk)$C(O)NR^{20}$, —$(C_0$-$C_6$ alk)Ar, —$(C_0$-$C_6$ alk)-O—$(C_0$-$C_6$ alk)Ar, —$(C_0$-$C_6$ alk)-OR, —$(C_0$-$C_6$ alk)$C(O)R^k$, or —$(C_0$-$C_6$ alk)-$NR^aR^{19}$, in which in which R, $R^e$, Ra, R19, Ar, Het, Hca, Cak are as described below. Each alk group may be, for example, an alkyl group. In desirable embodiments of the invention, $R^3$ is —$(C_0$-$C_6$ alk)$C(O)OR^e$, —$(C_0$-$C_6$ alk)$C(O)NR_2$, —$(C_0$-$C_6$ alk)$C(O)NR^aR^{19}$, —$(C_0$-$C_6$ alk)$C(O)NR^{19}{}_2$, —$(C_0$-$C_6$ alk)$C(O)NR^{20}$, —$(C_0$-$C_6$ alk)Ar, or, —$(C_0$-$C_6$ alk)-O—$(C_0$-$C_6$ alk)Ar. In other desirable embodiments of the invention, $R^3$ is —$(C_0$-$C_6$ alk)$C(O)OR^e$, —$(C_0$-$C_6$ alk)$C(O)NR^a{}_2$, —$(C_0$-$C_6$ alk)$C(O)NR^aR^{19}$, —$(C_0$-$C_6$ alk)$C(O)NR^{19}{}_2$, or —$(C_0$-$C_6$ alk)-$C(O)NR^{20}$. In further desirable embodiments of the invention, $R^3$ is —$(C_0$-$C_6$ alk)$C(O)OR$. In yet further desirable embodiments of the invention, $R^3$ is —$(C_0$-$C_6$ alk)$C(O)OR^e$ in which the —$(C_0$-$C_6$ alk) is —$(C_1$-$C_6$ alk), —$(C_1$-$C_4$ alk) or —$(C_1$-$C_2$ alk).

Other desirable $R^3$ substituents have gem-dialkyl or a monoalkyl substitution alpha to a functional group, e.g., a carbonyl carbon. Accordingly, in certain desirable embodiments of the invention, each $(C_0$-$C_6$ alkyl) connected directly to the piperazine ring as part of $R^3$ is a —$(C_0$-$C_5$ alkyl)$C(C_1$-$C_3$ alkyl)$_2$-, in which $(C_0$-$C_5$ alkyl) is independently optionally substituted with 1 or 2 substitutents selected independently from —$(C_1$-$C_4$ alkyl), —$(C_1$-$C_4$ alkoxy), —OH, =O, -halogen, —$C(O)O(C_1$-$C_3$ alkyl) and —$C(O)(C_1$-$C_3$ alkyl); and is optionally halogenated.

In certain especially desirable embodiments of the invention, $R^3$ is —$(C_0$-$C_6$ alk)$C(O)OR^e$, —$(C_0$-$C_6$ alk)$C(O)NR^a{}_2$, —$(C_0$-$C_6$ alk)$C(O)NR^aR^{19}$, —$(C_0$-$C_6$ alk)$C(O)NR^{19}{}_2$, or —$(C_0$-$C_6$ alk)-$C(O)NR^{20}$. In these embodiments, each $C0$-$C_6$ alkyl connected directly to the piperazine ring as part of $R^3$ may be, for example, $C_2$-$C_6$ alkyl, or alternatively $C_1$-$C_2$ alkyl. In certain embodiments of the invention $R^3$ is —$(C_0$-$C_5$ alkyl)$C(C_1$-$C_3$ alkyl)$_2C(O)OR$, —$(C_0$-$C_5$ alkyl)$C(C_1$-$C_3$ alkyl)$_2C(O)NR^a{}_2$, —$(C_1$-$C_5$ alkyl)$C(C_1$-$C_3$ alkyl)$_2C(O)NR^aR^{19}$, —$(C_0$-$C_5$ alkyl)$C(C_1$-$C_3$ alkyl)$_2C(O)NR^{19}{}_2$, —$(C_0$-$C_5$ alkyl)$C(C_1$-$C_3$ alkyl)$_2C(O)NR^{20}$, —$(C_1$-$C_5$ alkyl)$C(C_1$-$C_3$ alkyl)$_2$Ar, —$(C_0$-$C_6$ alk)-O—$(C_0$-$C_5$ alkyl)$C(C_1$-$C_3$ alkyl)$_2$Ar, —$(C_0$-$C_5$ alkyl)$C(C_1$-$C_3$ alkyl)$_2$CR, —$(C_0$-$C_5$ alkyl)$C(C_1$-$C_3$ alkyl)$_2C(O)R^k$, or —$(C_0$-$C_5$ alkyl)$C(C_1$-$C_3$ alkyl)$_2NR^aR^{19}$.

The $R^3$ group will form a stereogenic center on the piperazine ring. The $R^3$ group may be attached to the piperazine ring in an S configuration, or an R configuration. The compound or salt may exist as a racemic mixture, a scalemic mixture, or an enantiomerically- or diastereomerically-enriched mixture having at least about 80% enantiomeric or diastereomeric excess at the carbon of attachment of the $R^3$ group to the piperazine.

The piperazine is substituted with $R^4$ at the nitrogen distal from the dibenzo[b,f][1,4]oxazapine, as shown in Formula (I). $R^4$ may be, for example, —H or —R. In certain especially desirable embodiments of the invention, $R^4$ is H.

In the compounds according to this aspect of the invention, each $R^e$, $R^a$, $R^k$, Cak, Ar, Het, Hca are defined as in the section under Formulae (I) and (II) above.

In the compounds according to this aspect of the invention, each $R^{10}$ and $R^{11}$ is independently —H or —R, in which —R is as described below.

In the compounds according to this aspect of the invention, each $R^{19}$ is independently selected from —H, —OH and —R, in which R is as described below. Each alk group may be, for example, an alkyl group.

In the compounds according to this aspect of the invention, each $R^{20}$ is a Hca or Het ring wherein that N from the —$(C_0$-$C_6$ alk)$C(O)NR^{20}$, is a heteroatom in the Hca or Het ring, the ring optionally substituted with 1 or 2 substituents independently selected from =O, —$(C_1$-$C_6$ alkoxy), —OH, or -halogen; —$(C_1$-$C_6$ haloalkyl), —$SO_2$—$(C_1$-$C_6$ alk), and —$C(O)$—$(C_1$-$C_6$ alk).

In the compounds according to this aspect of the invention, each R is independently —$(C_1$-$C_8$ alk), —$(C_3$-$C_8$ cycloalk), —$(C_3$-$C_{12}$ heterocycloalk), —$(C_1$-$C_8$ haloalkyl), or —$(C_3$-$C_8$ halocycloalk), optionally substituted with 1, 2 or 3 substituents independently selected from —$(C_1$-$C_6$ alkoxy), —$(C_1$-$C_6$ hydroxyalkyoxy), —$(C_1$-$C_6$ hydroxyalkyl), acetoxyalkyl, —$C(O)O(C_1$-$C_6$ alkyl), —OH, =O, —N$(C_1$-$C_6$ alkyl)$_2$, —NH$(C_1$-$C_6$ alk), —$NH_2$, —OC(O)$(C_0$-$C_6$ alk), —$SO_2$—$(C_1$-$C_6$ alk), and —CO—$(C_0$-$C_6$ alk). Each —$(C_1$-$C_8$ haloalkyl) or —$(C_3$-$C_8$ halocycloalk), may be further optionally substituted with from 1 to 6 additional halogens. Each alk group may be, for example, an alkyl group.

In the compounds according to this aspect of the invention, each $(C_0$-$C_6$ alk), $(C_1$-$C_6$ alk), and —$(C_1$-$C_8$ alk) is independently optionally substituted with 1, 2, 3 or 4 substitutents selected independently from —$(C_1$-$C_4$ alkyl), —$(C_1$-$C_4$ alkoxy), —OH, =O, -halogen, —$C(O)O(C_1$-$C_3$ alkyl) and —$C(O)(C_1$-$C_3$ alkyl); and is optionally halogenated. Each alk group may be, for example, an alkyl group.

In this aspect of the invention, one or more of the alk groups may be alkenyl groups or alkynyl groups. In certain embodiments of the invention, at least one of the alk groups is an alkenyl group or an alkynyl group. Alternatively, in certain desirable embodiments of the invention, all of the alk groups are alkyl groups.

In desirable compounds according to this aspect of the invention, $R^3$ is —$(C_0$-$C_6$ alk)$C(O)OR^e$, —$(C_0$-$C_6$ alk)$C(O)NR^a{}_2$, —$(C_0$-$C_6$ alk)$C(O)NR^aR^{19}$, —$(C_0$-$C_6$ alk)$C(O)NR^{19}{}_2$, or —$(C_0$-$C_6$ alk)-$C(O)NR^{20}$. More desirably, $R^3$ is —$(CH_2)_p$$CO_2R^e$, —$(CH_2)_p$$CONR^a{}_2$, —$(CH_2)_p$$C(O)NR^aR^{19}$, —$(CH_2)_p$$C(O)NR^{20}$, or —$(CH_2)_p$$CONR^{19}{}_2$ in which p is 0, 1, 2, 3, 4, 5 or 6. For example, p may be 1 or 2. In certain desirable embodiments of the invention, the $R^3$ group has gem-dialkyl substitution alpha to its functional group. As such, each $(C_0$-$C_6$ alkyl) connected directly to the piperazine ring as part of $R^3$ is desirably a —$(C_0$-$C_5$ alkyl)$C(C_1$-$C_3$ alkyl)$_2$-group. For example, $R^3$ may be —$(C_0$-$C_5$ alkyl)$C(C_1$-$C_3$ alkyl)$_2C(O)OR^e$, —$(C_0$-$C_5$ alkyl)$C(C_1$-$C_3$ alkyl)$_2C(O)NR^a{}_2$, —$(C_0$-$C_5$ alkyl)$C(C_1$-$C_3$ alkyl)$_2C(O)NR^aR^{19}$, —$(C_0$-$C_5$ alkyl)$C(C_1$-$C_3$ alkyl)$_2C(O)NR^{19}{}_2$, —$(C_0$-$C_5$ alkyl)$C(C_1$-$C_3$ alkyl)$_2C(O)NR$, —$(CH_2)_qCR^d{}_2CO_2R^e$, —$(CH_2)_qCR^d{}_2CONR^a{}_2$, —$(CH_2)_qCR^d{}_2CONR^{19}{}_2$—$(CH_2)_qCR^d{}_2CONR^aR^{19}$ or —$(CH_2)_qCR^d{}_2CONR^{20}$, wherein q is 0, 1, 2, 3, 4 or 5, and each $R^d$ is individually -Me, -Et or —Pr. q is desirably 0, 1 or 2. In especially desirable embodiments of the invention, $R^3$ is —$(C_0$-$C_6$ alkyl)$C(O)OR^e$. $R^e$ may be, for example, —H, -Me, -Et, —Pr or —Bu. In further especially desirable embodiments of the invention, $R^3$ is —$(C_0$-$C_3$ alkyl)$C(O)OR^e$, wherein $R^e$ may be, for example, —H, -Me, -Et, —Pr or —Bu. In yet further especially desirable embodiments of the invention, $R^3$ is —$(C_1$-$C_2$ alkyl)$C(O)OR$, wherein $R^e$ may be, for example, —H, -Me, -Et, —Pr or —Bu. In other desirable embodiments of the invention, $R^3$ is —$(C_0$-$C_6$ alkyl)$C(O)NHR^a$, —$(C_0$-$C_3$ alkyl)$C(O)NHR^3$, or —$(C_1$-$C_2$ alkyl)$C(O)NHR^a$, wherein $R^a$ may be, for example, —H, -Me, -Et, —Pr or —Bu.

In this aspect of the invention, The $R^3$ group may be attached to the piperazine ring in an S configuration, or an R configuration. The compound or salt may exist as a racemic mixture, a scalemic mixture, or an enantomerically- or diastereomerically-enriched mixture having at least about 80% enantiomeric or diastereomeric excess at the carbon of attachment of the $R^3$ group to the piperazine.

In certain embodiments according to this aspect of the invention, $R^4$ is —H.

Another aspect of the invention relates to a compound having the structure of Formula (IV)

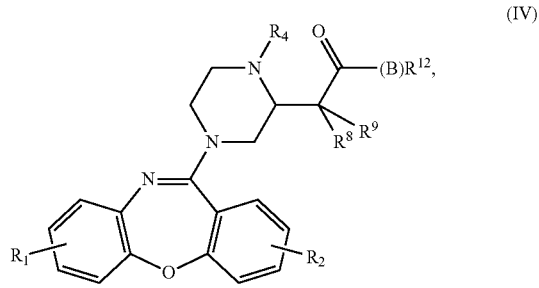

(IV)

or a pharmaceutically acceptable salt thereof, in which $R^1$ and $R^2$ are independently —Cl, —F, —Br, —I or —H, with the proviso that at least one of $R^1$ and $R^2$ is —Cl, —F, —Br or —I; $R^4$ is —H or —R; $R^8$ is —H, -Me, -Et or —Pr; $R^9$ is —H, -Me, -Et or —Pr; B is O or NH, and $R^{12}$ is —H, -Me, -Et or —Pr.

In certain desirable embodiments of the invention, B is O. In certain desirable embodiments of the invention, $R^8$ and $R^9$ are both -Me. In certain other desirable embodiments of the invention, $R^8$ and $R^9$ are both -Et. In certain other desirable embodiments of the invention, one of $R^8$ and $R^9$ is —H and the other is -Me, -Et or —Pr. The —Cl may be attached at the 7 position of the dibenzo[b,f][1,4]oxazepine or at the 8 position of the dibenzo[b,f][1,4]oxazepine. In other desirable embodiments of the invention, $R^4$ is —H.

Another aspect of the invention relates to compounds having one of the following structures, or pharmaceutically acceptable salts thereof:

| Compound | | Cmpnd |
|---|---|---|
| (E)-ethyl 2-(4-(8-chlorodibenzo[b,f][1,4]oxazepin-11-yl)piperazin-2-yl)acetate; | | A |
| (E)-2-(4-(8-chlorodibenzo[b,f][1,4]oxazepin-11-yl)piperazin-2-yl)-N-isobutylacetamide | 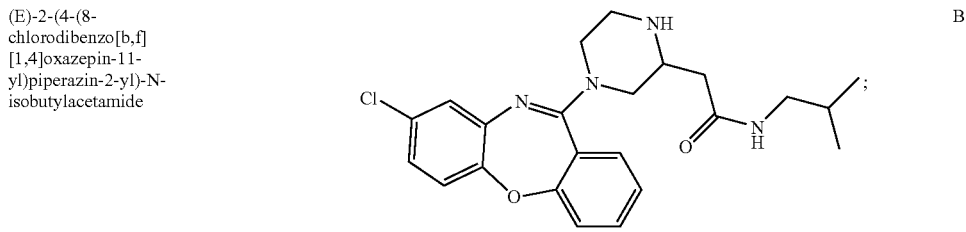 | B |
| (E)-ethyl 2-(4-(2-chlorodibenzo[b,f][1,4]oxazepin-11-yl)piperazine-2-yl)acetate<br>* (S) or (R) at stereocenter; | | C |
| (R,E)-methyl 4-((4-(2-chlorodibenzo[b,f][1,4]oxazepin-11-yl)piperazin-2-yl)methoxy)benzoate | 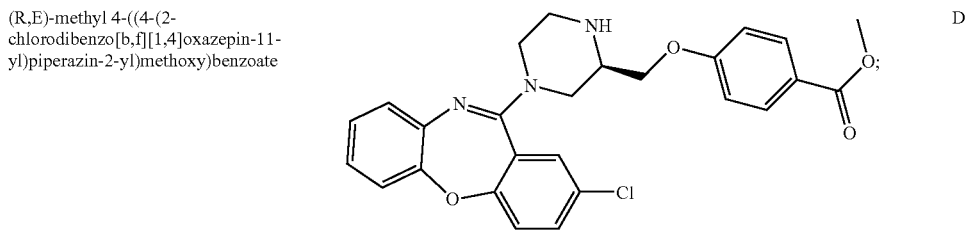 | D |
| (E)-2-(4-(8-chlorodibenzo[b,f][1,4]oxazepin-11-yl)piperazin-2-yl)acetic acid; | | E |

-continued

| Compound | | Cmpnd |
|---|---|---|
| (E)-ethyl 4-(2-(4-(8-chlorodibenzo[b,f][1,4]oxazepin-11-yl)piperazin-2-yl)ethyl)benzoate | 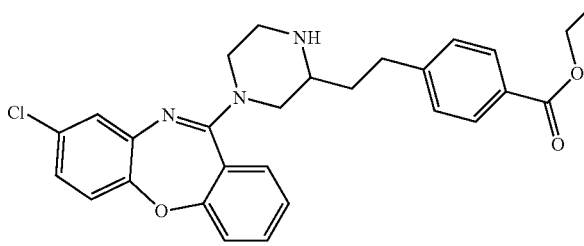 | F |
| (E)-methyl 4-((4-(8-chlorodibenzo[b,f][1,4]oxazepin-11-yl)piperazin-2-yl)methoxy)benzoate | 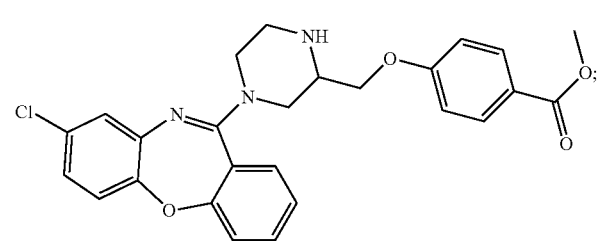 | G |
| (E)-ethyl 2-(4-(7-chlorodibenzo[b,f][1,4]oxazepin-11-yl)piperazin-2-yl)acetate | 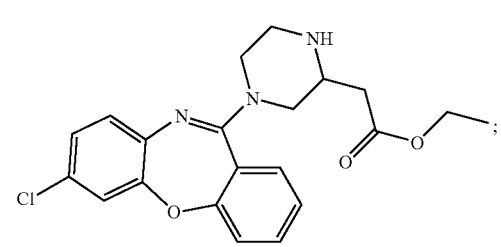 | H |
| (E)-methyl 2-(4-(8-chlorodibenzo[b,f][1,4]oxazepin-11-yl)piperazin-2-yl)acetate; | | I |
| (E)-ethyl 2-(4-(7-fluorodibenzo[b,f][1,4]oxazepin-11-yl)piperazin-2-yl)acetate | 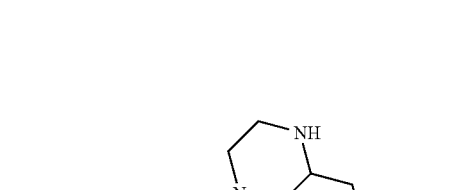 | J |
| (S,E)-ethyl 2-(4-(8-chlorodibenzo[b,f][1,4]oxazepin-11-yl)piperazin-2-yl)acetate | 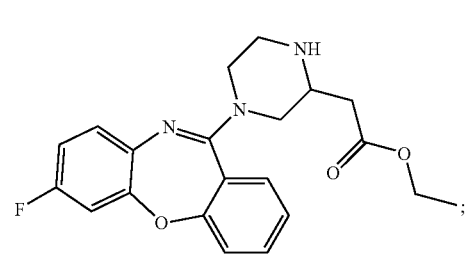 | K |
| (E)-isopropyl 2-(4-(8-chlorodibenzo[b,f][1,4]oxazepin-11-yl)piperazin-2-yl)acetate | 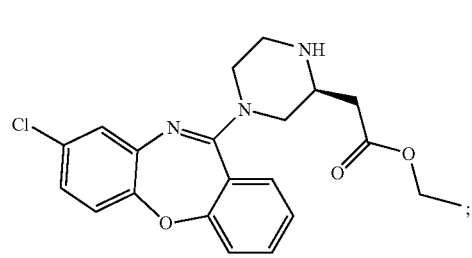 | L |

-continued

| Compound | | Cmpnd |
|---|---|---|
| (E)-isopropyl 2-(4-(7-fluorodibenzo[b,f][1,4]oxazepin-11-yl)piperazin-2-yl)acetate | | M |
| (S,E)-methyl 2-(4-(8-chlorodibenzo[b,f][1,4]oxazepin-11-yl)piperazin-2-yl)acetate | | N |
| (R,E)-ethyl 2-(4-(8-chlorodibenzo[b,f][1,4]oxazepin-11-yl)piperazin-2-yl)acetate; | | O |
| (R,E)-methyl 2-(4-(8-chlorodibenzo[b,f][1,4]oxazepin-11-yl)piperazin-2-yl)acetate; | | P |
| (S,E)-2-(4-(8-chlorodibenzo[b,f][1,4]oxazepin-11-yl)piperazin-2-yl)acetic acid | | Q |
| (R)-2-((S)-4-((E)-8-chlorodibenzo[b,f][1,4]oxazepin-11-yl)piperazin-2-yl)propanoic acid | | R |
| (S)-2-((S)-4-((E)-8-chlorodibenzo[b,f][1,4]oxazepin-11-yl)piperazin-2-yl)propanoic acid | | S |
| (R)-2-((S)-4-((E)-8-chlorodibenzo[b,f][1,4]oxazepin-11-yl)piperazin-2-yl)butanoic acid; | | T |
| (S)-2-((S)-4-((E)-8-chlorodibenzo[b,f][1,4]oxazepin-11-yl)piperazin-2-yl)butanoic acid; | | U |

-continued

| Compound | | Cmpnd |
|---|---|---|
| (S,E)-2-(4-(8-chlorodibenzo[b,f][1,4]oxazepin-11-yl)piperazin-2-yl)-2-methylpropanoic acid | | X |
| (S,E)-2-(4-(8-chlorodibenzo[b,f][1,4]oxazepin-11-yl)piperazin-2-yl)-2-ethylbutanoic acid; | | Y |
| (R,E)-2-(4-(8-chlorodibenzo[b,f][1,4]oxazepin-11-yl)piperazin-2-yl)acetic acid | | AB |
| (R)-2-((R)-4-((E)-8-chlorodibenzo[b,f][1,4]oxazepin-11-yl)piperazin-2-yl)propanoic acid | | AC |
| (S)-2-((R)-4-((E)-8-chlorodibenzo[b,f][1,4]oxazepin-11-yl)piperazin-2-yl)propanoic acid | | AD |
| (R)-2-((R)-4-((E)-8-chlorodibenzo[b,f][1,4]oxazepin-11-yl)piperazin-2-yl)butanoic acid | | AE |
| (S)-2-((R)-4-((E)-8-chlorodibenzo[b,f][1,4]oxazepin-11-yl)piperazin-2-yl)butanoic acid | | AF |

-continued

| Compound | | Cmpnd |
|---|---|---|
| (R,E)-2-(4-(8-chlorodibenzo[b,f][1,4]oxazepin-11-yl)piperazin-2-yl)-2-methylpropanoic acid | | AI |
| (R,E)-2-(4-(8-chlorodibenzo[b,f][1,4]oxazepin-11-yl)piperazin-2-yl)-2-ethylbutanoic acid | | AJ |
| (2R)-2-(4-((E)-2-chlorodibenzo[b,f][1,4]oxazepin-11-yl)piperazin-2-yl)propanoic acid<br>* (S) or (R) at stereocenter | | AM |
| (2S)-2-(4-((E)-2-chlorodibenzo[b,f][1,4]oxazepin-11-yl)piperazin-2-yl)propanoic acid<br>* (S) or (R) at stereocenter | | AN |
| (2R)-2-(4-((E)-2-chlorodibenzo[b,f][1,4]oxazepin-11-yl)piperazin-2-yl)butanoic acid<br>* (S) or (R) at stereocenter | | AO |
| (2S)-2-(4-((E)-2-chlorodibenzo[b,f][1,4]oxazepin-11-yl)piperazin-2-yl)butanoic acid<br>* (S) or (R) at stereocenter | | AP |

| Compound | | Cmpnd |
|---|---|---|
| (E)-2-(4-(2-chlorodibenzo[b,f][1,4]oxazepin-11-yl)piperazin-2-yl)-2-methylpropanoic acid * (S) or (R) at stereocenter | 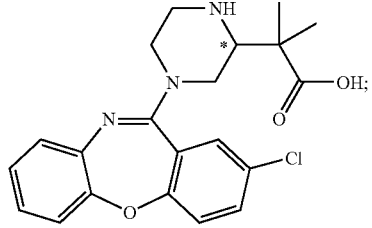 | AS |
| (E)-2-(4-(2-chlorodibenzo[b,f][1,4]oxazepin-11-yl)piperazin-2-yl)-2-ethylbutanoic acid * (S) or (R) at stereocenter | 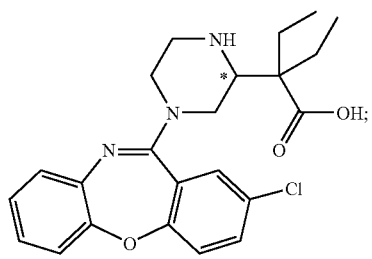 | AT |
| (E)-ethyl 2-(4-(8-chlorodibenzo[b,f][1,4]oxazepin-11-yl)piperazin-2-yl)propanoate | 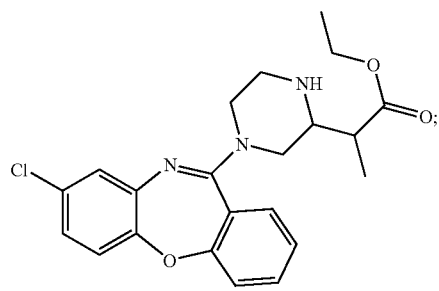 | AW |
| (E)-ethyl 2-(4-(8-chlorodibenzo[b,f][1,4]oxazepin-11-yl)piperazin-2-yl)butanoate | 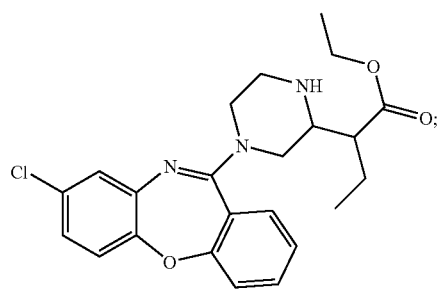 | AX |
| (E)-ethyl 2-(4-(8-chlorodibenzo[b,f][1,4]oxazepin-11-yl)piperazin-2-yl)pentanoate | 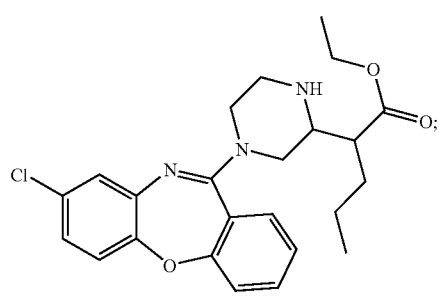 | AY |

-continued

| Compound | Cmpnd |
|---|---|
| (E)-ethyl 2-(4-(8-chlorodibenzo[b,f][1,4]oxazepin-11-yl)piperazin-2-yl)-2-methylpropanoate | AZ |
| (E)-ethyl 2-(4-(8-chlorodibenzo[b,f][1,4]oxazepin-11-yl)piperazin-2-yl)-2-ethylbutanoate | BA |
| (E)-ethyl 2-(4-(8-chlorodibenzo[b,f][1,4]oxazepin-11-yl)piperazin-2-yl)-2-methylbutanoate | BB |
| (2R)-ethyl 2-(4-((E)-2-chlorodibenzo[b,f][1,4]oxazepin-11-yl)piperazin-2-yl)propanoate<br>* (S) or (R) at stereocenter | BC |
| (2S)-ethyl 2-(4-((E)-2-chlorodibenzo[b,f][1,4]oxazepin-11-yl)piperazin-2-yl)propanoate<br>* (S) or (R) at stereocenter | BD |

-continued

| Compound | | Cmpnd |
|---|---|---|
| (2R)-ethyl 2-(4-((E)-2-chlorodibenzo[b,f][1,4]oxazepin-11-yl)piperazin-2-yl)butanoate<br>* (S) or (R) at stereocenter | | BE |
| (2S)-ethyl 2-(4-((E)-2-chlorodibenzo[b,f][1,4]oxazepin-11-yl)piperazin-2-yl)butanoate<br>* (S) or (R) at stereocenter | | BF |
| (E)-ethyl 2-(4-(2-chlorodibenzo[b,f][1,4]oxazepin-11-yl)piperazin-2-yl)-2-methylpropanoate<br>* (S) or (R) at stereocenter | | BI |
| (E)-ethyl 2-(4-(2-chlorodibenzo[b,f][1,4]oxazepin-11-yl)piperazin-2-yl)-2-ethylbutanoate<br>* (S) or (R) at stereocenter | | BJ |
| (R)-ethyl 2-((R)-4-((E)-8-chlorodibenzo[b,f][1,4]oxazepin-11-yl)piperazin-2-yl)propanoate; | | BM |
| (S)-ethyl 2-((R)-4-((E)-8-chlorodibenzo[b,f][1,4]oxazepin-11-yl)piperazin-2-yl)propanoate; | | BN |
| (R)-ethyl 2-((R)-4-((E)-8-chlorodibenzo[b,f][1,4]oxazepin-11-yl)piperazin-2-yl)butanoate; | | BO |
| (S)-ethyl 2-((R)-4-((E)-8-chlorodibenzo[b,f][1,4]oxazepin-11-yl)piperazin-2-yl)butanoate; | | BP |
| (R,E)-ethyl 2-(4-(8-chlorodibenzo[b,f][1,4]oxazepin-11-yl)piperazin-2-yl)-2-methylpropanoate; | | BS |
| (R,E)-ethyl 2-(4-(8-chlorodibenzo[b,f][1,4]oxazepin-11-yl)piperazin-2-yl)-2-ethylbutanoate; | | BT |

| Compound | | Cmpnd |
|---|---|---|
| (S)-ethyl 2-((S)-4-((E)-8-chlorodibenzo[b,f][1,4]oxazepin-11-yl)piperazin-2-yl)propanoate | | BW |
| (R)-ethyl 2-((S)-4-((E)-8-chlorodibenzo[b,f][1,4]oxazepin-11-yl)piperazin-2-yl)propanoate | | BX |
| (S)-ethyl 2-((S)-4-((E)-8-chlorodibenzo[b,f][1,4]oxazepin-11-yl)piperazin-2-yl)butanoate; | | BY |
| (R)-ethyl 2-((S)-4-((E)-8-chlorodibenzo[b,f][1,4]oxazepin-11-yl)piperazin-2-yl)butanoate; | | BZ |
| (S,E)-ethyl 2-(4-(8-chlorodibenzo[b,f][1,4]oxazepin-11-yl)piperazin-2-yl)-2-methylpropanoate | | CC |
| (S,E)-ethyl 2-(4-(8-chlorodibenzo[b,f][1,4]oxazepin-11-yl)piperazin-2-yl)-2-ethylbutanoate; | | CD |
| (E)-methyl 2-(4-(8-chlorodibenzo[b,f][1,4]oxazepin-11-yl)piperazin-2-yl)propanoate; | | CG |
| (E)-methyl 2-(4-(8-chlorodibenzo[b,f][1,4]oxazepin-11-yl)piperazin-2-yl)butanoate; | | CH |
| (E)-methyl 2-(4-(8-chlorodibenzo[b,f][1,4]oxazepin-11-yl)piperazin-2-yl)pentanoate; | | CI |
| (E)-methyl 2-(4-(8-chlorodibenzo[b,f][1,4]oxazepin-11-yl)piperazin-2-yl)-2-methylpropanoate; | | CJ |
| (E)-methyl 2-(4-(8-chlorodibenzo[b,f][1,4]oxazepin-11-yl)piperazin-2-yl)-2-ethylbutanoate; | | CK |
| (E)-methyl 2-(4-(8-chlorodibenzo[b,f][1,4]oxazepin-11-yl)piperazin-2-yl)-2-methylbutanoate; | | CL |
| (E)-2-(4-(8-chlorodibenzo[b,f][1,4]oxazepin-11-yl)piperazin-2-yl)propanoic acid; | | CM |
| (E)-2-(4-(8-chlorodibenzo[b,f][1,4]oxazepin-11-yl)piperazin-2-yl)butanoic acid; | | CN |

| Compound | Cmpnd |
|---|---|
| (E)-2-(4-(8-chlorodibenzo[b,f][1,4]oxazepin-11-yl)piperazin-2-yl)pentanoic acid; | CO |
| (E)-2-(4-(8-chlorodibenzo[b,f][1,4]oxazepin-11-yl)piperazin-2-yl)-2-methylpropanoic acid; | CP |
| (E)-2-(4-(8-chlorodibenzo[b,f][1,4]oxazepin-11-yl)piperazin-2-yl)-2-ethylbutanoic acid; | CQ |
| (E)-2-(4-(8-chlorodibenzo[b,f][1,4]oxazepin-11-yl)piperazin-2-yl)-2-methylbutanoic acid; | CR |
| (R)-methyl 2-((R)-4-((E)-8-chlorodibenzo[b,f][1,4]oxazepin-11-yl)piperazin-2-yl)propanoate; | CS |
| (S)-methyl 2-((R)-4-((E)-8-chlorodibenzo[b,f][1,4]oxazepin-11-yl)piperazin-2-yl)propanoate; | CT |
| (R)-methyl 2-((R)-4-((E)-8-chlorodibenzo[b,f][1,4]oxazepin-11-yl)piperazin-2-yl)butanoate; | CU |
| (S)-methyl 2-((R)-4-((E)-8-chlorodibenzo[b,f][1,4]oxazepin-11-yl)piperazin-2-yl)butanoate; | CV |
| (R,E)-methyl 2-(4-(8-chlorodibenzo[b,f][1,4]oxazepin-11-yl)piperazin-2-yl)-2-methylpropanoate; | CY |
| (R,E)-methyl 2-(4-(8-chlorodibenzo[b,f][1,4]oxazepin-11-yl)piperazin-2-yl)-2-ethylbutanoate; | CZ |
| (S)-methyl 2-((S)-4-((E)-8-chlorodibenzo[b,f][1,4]oxazepin-11-yl)piperazin-2-yl)propanoate | DC |
| (R)-methyl 2-((S)-4-((E)-8-chlorodibenzo[b,f][1,4]oxazepin-11-yl)piperazin-2-yl)propanoate | DD |
| (R)-methyl 2-((S)-4-((E)-8-chlorodibenzo[b,f][1,4]oxazepin-11-yl)piperazin-2-yl)butanoate; | DE |
| (S)-methyl 2-((S)-4-((E)-8-chlorodibenzo[b,f][1,4]oxazepin-11-yl)piperazin-2-yl)butanoate; | DF |
| (S,E)-methyl 2-(4-(8-chlorodibenzo[b,f][1,4]oxazepin-11-yl)piperazin-2-yl)-2-methylpropanoate | DI |

| Compound | Cmpnd |
|---|---|
| (S,E)-methyl 2-(4-(8-chlorodibenzo[b,f][1,4]oxazepin-11-yl)piperazin-2-yl)-2-ethylbutanoate; | DJ |
| (E)-methyl 2-((4-(2-chlorodibenzo[b,f][1,4]oxazepin-11-yl)-1-methylpiperazin-2-yl)methoxy)acetate | DM |
| (E)-ethyl 2-(4-(8-chlorodibenzo[b,f][1,4]oxazepin-11-yl)-1-methylpiperazin-2-yl)acetate | DN |
| (E)-2-(4-(8-chlorodibenzo[b,f][1,4]oxazepin-11-yl)-1-methylpiperazin-2-yl)acetic acid | DO |
| (E)-methyl 2-(4-(8-(trifluoromethyl)dibenzo[b,f][1,4]oxazepin-11-yl)piperazin-2-yl)acetate | DQ |
| (S,E)-cyclopentyl 2-(4-(8-chlorodibenzo[b,f][1,4]oxazepin-11-yl)piperazin-2-yl)acetate | DR |
| (S)-quinuclidin-3-yl 2-((S)-4-((E)-8-chlorodibenzo[b,f][1,4]oxazepin-11-yl)-1-methylpiperazin-2-yl)acetate; | DS |

-continued

| Compound | | Cmpnd |
|---|---|---|
| (R)-quinuclidin-3-yl 2-((S)-4-((E)-8-chlorodibenzo[b,f][1,4]oxazepin-11-yl)piperazin-2-yl)acetate | | DT |
| (S)-quinuclidin-3-yl 2-((S)-4-((E)-8-chlorodibenzo[b,f][1,4]oxazepin-11-yl)piperazin-2-yl)acetate | | DU |
| (S,E)-tetrahydro-2H-pyran-4-yl 2-(4-(8-chlorodibenzo[b,f][1,4]oxazepin-11-yl)piperazin-2-yl)acetate | | DV |
| (S,E)-methyl 2-(4-(8-chlorodibenzo[b,f][1,4]oxazepin-11-yl)-1-methylpiperazin-2-yl)acetate | | DW |
| (S,E)-cyclopentyl 2-(4-(8-chlorodibenzo[b,f][1,4]oxazepin-11-yl)-1-methylpiperazin-2-yl)acetate | | DX |
| sec-butyl 2-((S)-4-((E)-8-chlorodibenzo[b,f][1,4]oxazepin-11-yl)-1-methylpiperazin-2-yl)acetate | | DY |

-continued

| Compound | | Cmpnd |
|---|---|---|
| (S,E)-tetrahydro-2H-pyran-4-yl 2-(4-(8-chlorodibenzo[b,f][1,4]oxazepin-11-yl)-1-methylpiperazin-2-yl)acetate | 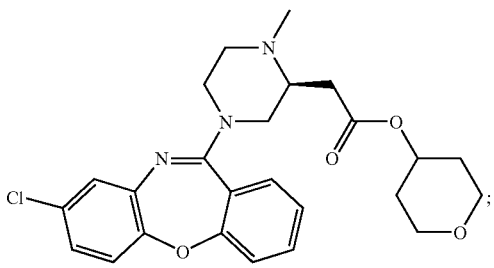 | DZ |
| (S,E)-neopentyl 2-(4-(8-chlorodibenzo[b,f][1,4]oxazepin-11-yl)piperazin-2-yl)acetate | 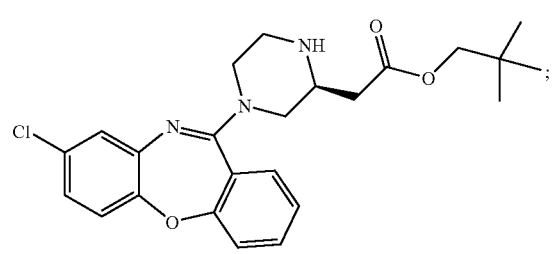 | EA |
| (S,E)-3-methoxy-3-methylbutyl 2-(4-(8-chlorodibenzo[b,f][1,4]oxazepin-11-yl)piperazin-2-yl)acetate | 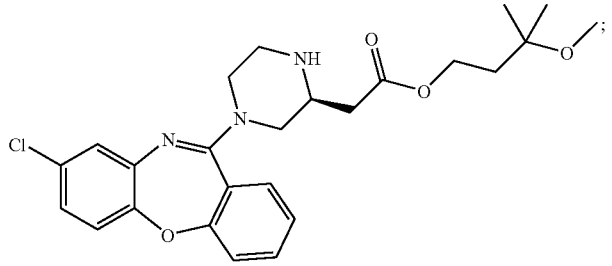 | EB |
| (S,E)-3-hydroxy-3-methylbutyl 2-(4-(8-chlorodibenzo[b,f][1,4]oxazepin-11-yl)piperazin-2-yl)acetate | 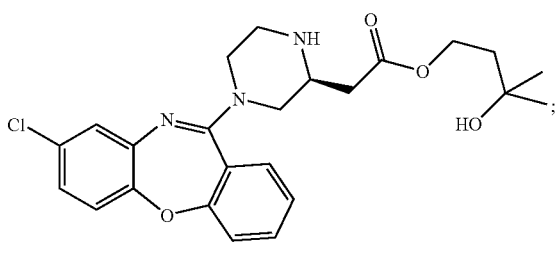 | EC |
| (R)-4-hydroxy-4-methylpentan-2-yl 2-((S)-4-((E)-8-chlorodibenzo[b,f][1,4]oxazepin-11-yl)piperazin-2-yl)acetate; | | ED |
| (S)-((R)-4-hydroxy-4-methylpentan-2-yl) 2-((S)-4-((E)-8-chlorodibenzo[b,f][1,4]oxazepin-11-yl)piperazin-2-yl)propanoate; | | EE |
| (R)-((R)-4-hydroxy-4-methylpentan-2-yl) 2-((S)-4-((E)-8-chlorodibenzo[b,f][1,4]oxazepin-11-yl)piperazin-2-yl)propanoate; | | EF |
| (S)-((R)-4-hydroxy-4-methylpentan-2-yl) 2-((S)-4-((E)-8-chlorodibenzo[b,f][1,4]oxazepin-11-yl)piperazin-2-yl)butanoate; | | EG |
| (R)-((R)-4-hydroxy-4-methylpentan-2-yl) 2-((S)-4-((E)-8-chlorodibenzo[b,f][1,4]oxazepin-11-yl)piperazin-2-yl)butanoate; | | EH |
| (R)-4-hydroxy-4-methylpentan-2-yl 2-((S)-4-((E)-8-chlorodibenzo[b,f][1,4]oxazepin-11-yl)piperazin-2-yl)-2-methylpropanoate; | | EK |
| (R)-4-hydroxy-4-methylpentan-2-yl 2-((S)-4-((E)-8- | | EL |

-continued

| Compound | Cmpnd |
|---|---|
| chlorodibenzo[b,f][1,4]oxazepin-11-yl)piperazin-2-yl)-2-ethylbutanoate; | |
| (2S,4S)-4-hydroxypentan-2-yl 2-((S)-4-((E)-8-chlorodibenzo[b,f][1,4]oxazepin-11-yl)piperazin-2-yl)acetate | EO |
| sec-butyl 2-((S)-4-((E)-8-chlorodibenzo[b,f][1,4]oxazepin-11-yl)piperazin-2-yl)acetate | EP |
| (S)-tetrahydrofuran-3-yl 2-((S)-4-((E)-8-chlorodibenzo[b,f][1,4]oxazepin-11-yl)piperazin-2-yl)acetate | EQ |
| (S,E)-ethyl 2-(4-(8-chlorodibenzo[b,f][1,4]oxazepin-11-yl)-1-isopentylpiperazin-2-yl)acetate | ER |
| (R)-1-methylpyrrolidin-3-yl 2-((S)-4-((E)-8-chlorodibenzo[b,f][1,4]oxazepin-11-yl)-1-methylpiperazin-2-yl)acetate | ES |

-continued

| Compound | | Cmpnd |
|---|---|---|
| (S,E)-methyl 2-(4-(8-chlorodibenzo[b,f][1,4]oxazepin-11-yl)-1-(cyclopropylmethyl)piperazin-2-yl)acetate | | ET |
| (S,E)-2-(4-(8-chlorodibenzo[b,f][1,4]oxazepin-11-yl)-1-methylpiperazin-2-yl)-N-(2,2,3,3,3-pentafluoropropyl)acetamide | | EU |
| (S,E)-2-(4-(8-chlorodibenzo[b,f][1,4]oxazepin-11-yl)-1-methylpiperazin-2-yl)-N-(1,3-difluoropropan-2-yl)acetamide | | EV |
| (S,E)-2-(4-(8-chlorodibenzo[b,f][1,4]oxazepin-11-yl)-1-methylpiperazin-2-yl)-N,N-bis(2,2,2-trifluoroethyl)acetamide | | EW |
| (S,E)-3-fluoropropyl 2-(4-(8-chlorodibenzo[b,f][1,4]oxazepin-11-yl)-1-methylpiperazin-2-yl)acetate | | EX |
| (S,E)-2-(4-(8-chlorodibenzo[b,f][1,4]oxazepin-11-yl)piperazin-2-yl)-N-(1-hydroxy-2-methylpropan-2-yl)acetamide; | | EY |

| Compound | | Cmpnd |
|---|---|---|
| (S,E)-2-(4-(8-chlorodibenzo[b,f][1,4]oxazepin-11-yl)piperazin-2-yl)-N-(2-hydroxyethyl)-N-propylacetamide | | EZ |
| (S,E)-2-(4-(8-chlorodibenzo[b,f][1,4]oxazepin-11-yl)piperazin-2-yl)-N-(2-hydroxyethyl)acetamide; | | FA |
| 2-((S)-4-((E)-8-chlorodibenzo[b,f][1,4]oxazepin-11-yl)piperazin-2-yl)-N-((R)-2-hydroxypropyl)acetamide; | | FB |
| (S,E)-2-(4-(8-chlorodibenzo[b,f][1,4]oxazepin-11-yl)piperazin-2-yl)-N-(2-methoxyethyl)acetamide; | | FC |
| (R)-2-((S)-4-((E)-8-chlorodibenzo[b,f][1,4]oxazepin-11-yl)piperazin-2-yl)-N-(2-methoxyethyl)propanamide; | | FD |
| (S)-2-((S)-4-((E)-8-chlorodibenzo[b,f][1,4]oxazepin-11-yl)piperazin-2-yl)-N-(2-methoxyethyl)propanamide; | | FE |
| (R)-2-((S)-4-((E)-8-chlorodibenzo[b,f][1,4]oxazepin-11-yl)piperazin-2-yl)-N-(2-methoxyethyl)butanamide; | | FF |
| (S)-2-((S)-4-((E)-8-chlorodibenzo[b,f][1,4]oxazepin-11-yl)piperazin-2-yl)-N-(2-methoxyethyl)butanamide; | | FG |
| (S,E)-2-(4-(8-chlorodibenzo[b,f][1,4]oxazepin-11-yl)piperazin-2-yl)-N-(2-methoxyethyl)-2-methylpropanamide; | | FJ |
| (S,E)-2-(4-(8-chlorodibenzo[b,f][1,4]oxazepin-11-yl)piperazin-2-yl)-2-ethyl-N-(2-methoxyethyl)butanamide; | | FK |
| (S,E)-2-(4-(8-chlorodibenzo[b,f][1,4]oxazepin-11-yl)piperazin-2-yl)-N-(2-(2-hydroxyethoxy)ethyl)acetamide; | | FN |
| (S,E)-2-(4-(8-chlorodibenzo[b,f][1,4]oxazepin-11-yl)piperazin-2-yl)-N-(2-hydroxyethyl)-N-methylacetamide | | FO |
| (S,E)-2-(4-(8-chlorodibenzo[b,f][1,4]oxazepin-11-yl)piperazin-2-yl)-N-(6-methoxypyridin-3-yl)acetamide | | FP |

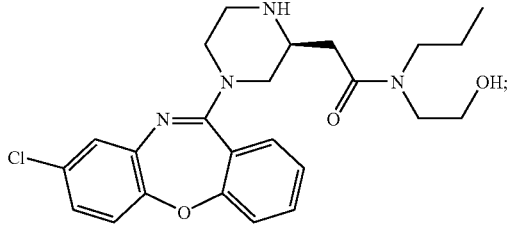

-continued

| Compound | Cmpnd |
|---|---|
| (S,E)-2-(4-(8-chlorodibenzo[b,f][1,4]oxazepin-11-yl)piperazin-2-yl)-N-(2,2-difluoroethyl)acetamide | FQ |
| 2-((S)-4-((E)-8-chlorodibenzo[b,f][1,4]oxazepin-11-yl)piperazin-2-yl)-N-(((S)-tetrahydrofuran-2-yl)methyl)acetamide; | FR |
| (S,E)-2-(4-(8-chlorodibenzo[b,f][1,4]oxazepin-11-yl)piperazin-2-yl)-N-(3-hydroxypropyl)acetamide; | FS |
| (R)-2-((S)-4-((E)-8-chlorodibenzo[b,f][1,4]oxazepin-11-yl)piperazin-2-yl)-N-(3-hydroxypropyl)propanamide; | FT |
| (S)-2-((S)-4-((E)-8-chlorodibenzo[b,f][1,4]oxazepin-11-yl)piperazin-2-yl)-N-(3-hydroxypropyl)propanamide; | FU |
| (R)-2-((S)-4-((E)-8-chlorodibenzo[b,f][1,4]oxazepin-11-yl)piperazin-2-yl)-N-(3-hydroxypropyl)butanamide; | FV |
| (S)-2-((S)-4-((E)-8-chlorodibenzo[b,f][1,4]oxazepin-11-yl)piperazin-2-yl)-N-(3-hydroxypropyl)butanamide; | FW |
| (S,E)-2-(4-(8-chlorodibenzo[b,f][1,4]oxazepin-11-yl)piperazin-2-yl)-N-(3-hydroxypropyl)-2-methylpropanamide; | FZ |
| (S,E)-2-(4-(8-chlorodibenzo[b,f][1,4]oxazepin-11-yl)piperazin-2-yl)-2-ethyl-N-(3-hydroxypropyl)butanamide; | GA |
| (S,E)-2-(4-(8-chlorodibenzo[b,f][1,4]oxazepin-11-yl)piperazin-2-yl)-N-(3-methoxypropyl)acetamide | GD |
| 2-((S)-4-((E)-8-chlorodibenzo[b,f][1,4]oxazepin-11-yl)piperazin-2-yl)-1-((R)-3-hydroxypyrrolidin-1-yl)ethanone | GE |

| Compound | | Cmpnd |
|---|---|---|
| 2-((S)-4-((E)-8-chlorodibenzo[b,f][1,4]oxazepin-11-yl)piperazin-2-yl)-N-(3,3,3-trifluoro-2-hydroxypropyl)acetamide | | GF |
| (S,E)-2-(4-(8-chlorodibenzo[b,f][1,4]oxazepin-11-yl)piperazin-2-yl)-1-morpholinoethanone; | | GG |
| 2-((S)-4-((E)-8-chlorodibenzo[b,f][1,4]oxazepin-11-yl)piperazin-2-yl)-1-((S)-2-(trifluoromethyl)pyrrolidin-1-yl)ethanone | | GH |
| (S,E)-2-(4-(8-chlorodibenzo[b,f][1,4]oxazepin-11-yl)-1-(2-hydroxyethyl)piperazin-2-yl)-N-(2-methoxyethyl)acetamide | | GI |

All names and structures were generated using ChemDraw Ultra v. 9.01, which is available from Cambridgesoft (www-.cambridgesoft.com).

Another aspect of the invention relates to the compounds recited herein that are hydroxylated one or more times at positions 1-4 or 6-9 according to the numbering illustrated in Formula (V)

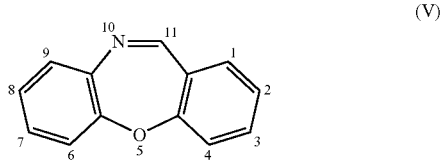

(V)

wherein the hydroxyl group replaces a H.

Another aspect of the invention relates to methods for preparing a compound of Formula F

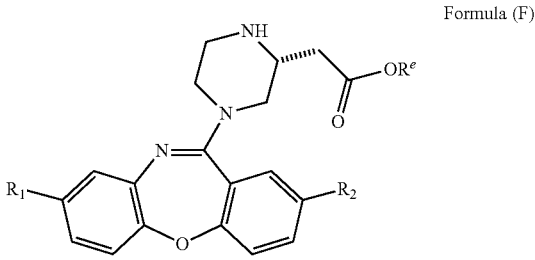

Formula (F)

comprising converting a compound of formula (A)

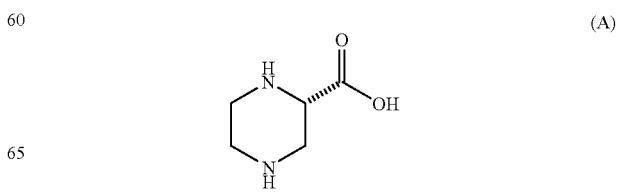

(A)

or its salt to a compound of formula (B)

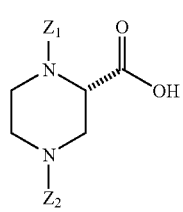
(B)

or it's salt, respectively, wherein $Z_1$ and $Z_2$ are nitrogen protecting groups (wherein commonly known and used N protecting groups can be used, e.g. N-benzyl; N-nitrobenzyl; N-BoC; N-oxide; N-paramethoxybenzyl; N-benzylsulfonyl; N-carbobenzyloxy (N-CBZ)); converting compound of formula (B)

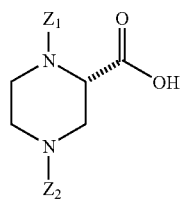
(B)

to an acid chloride followed by converting to the corresponding diazide, formula (C)

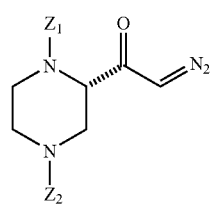
(C)

wherein $Z_1$ and $Z_2$ are again nitrogen protecting groups; treating a compound of formula (C)

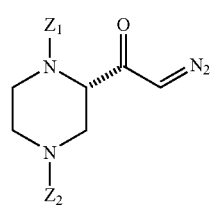
(C)

with a silver catalyst and an alcohol to make formula (D)

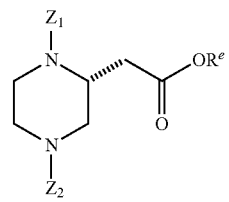
(D)

wherein $Z_1$ and $Z_2$ are nitrogen protecting groups, $R^e$ is as defined for Formula I herein, here in the form of an ester. In additional embodiments of the invention, $R^e$ can be —($C_1$-$C_6$ alk), —($C_1$-$C_6$ alk)-OR, —($C_1$-$C_6$ alk)-OH, —($C_0$-$C_6$ alk)C(O)OR, —($C_1$-$C_6$ alk)-$NR^{19}_2$, —($C_0$-$C_6$ alk)Hca, —($C_0$-$C_6$ alk)Ar, —($C_0$-$C_6$ alk)Het, or —($C_0$-$C_6$ alk)Cak. In further embodiments of the invention, $R^e$ can be —($C_1$-$C_6$ alk), —($C_1$-$C_4$ alk), —($C_1$-$C_2$ alk), or —($C_2$ alk); deprotecting a compound of formula (D)

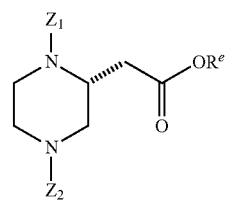
(D)

or its salt to a compound of formula (E)

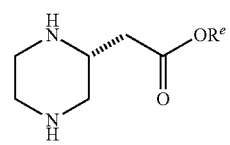
(E)

or it's salt, respectively; alkylating a compound of formula (E)

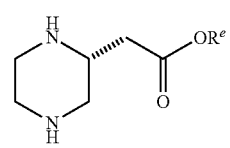
(E)

or its salt with a compound of formula (G)

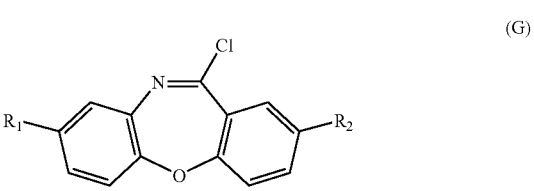
(G)

or it's salt to a compound of formula (F)

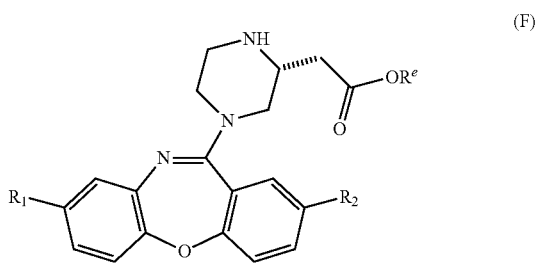

or it's salt, respectively, wherein $R_2$ and $R_1$ are independently H, I, Br, Cl, or I, and wherein in each instance the bond between the piperizine and carbonyl moiety is racemic, R or S. $R^e$ is as defined for Formula I herein. In additional embodiments of the invention, $R^e$ can be —$(C_1$-$C_6$ alk), —$(C_1$-$C_6$ alk)-OR, —$(C_1$-$C_6$ alk)-OH, —$(C_0$-$C_6$ alk)C(O)OR, —$(C_1$-$C_6$ alk)-NR$^{19}{}_2$, —$(C_0$-$C_6$ alk)Hca, —$(C_0$-$C_6$ alk)Ar, —$(C_0$-$C_6$ alk)Het, or —$(C_0$-$C_6$ alk)Cak. In further embodiments of the invention, $R^e$ can be —$(C_1$-$C_6$ alk), —$(C_1$-$C_4$ alk), —$(C_1$-$C_2$ alk), or —$(C_2$ alk). See Example 1 for an example synthesis.

Another aspect of the invention relates to methods of treating various disorders related to affector binding at the receptors recited elsewhere herein. Exemplary indications for each of the compounds, salts and compositions recited herein include one or more of the following: acute treatment and maintenance of treatment for: schizophrenia, treatment-resistant schizophrenia, pediatric schizophrenia, cognitive symptoms or impairment (e.g., problems in speed of processing, attention/vigilance, working memory, verbal learning, visual learning, reasoning and problem solving, and social cognition), negative symptoms (e.g., flattened or masked affect, alogia, avolition, anhedonia, and attentional impairment), bipolar disorder, pediatric bipolar disorder, depression, psychotic depression, treatment-resistant depression, treatment of obsessive-compulsive disorder (OCD), autism, senile psychosis, psychotic dementia, L-DOPA induced psychosis, psychogenic polydipsia, other delusional states (e.g., erotomania, secondary alcoholism, etc), psychotic symptoms associated with neurological disorders (e.g. Huntington's Chorea, Wilson's Disease), sleep disorders, depressed states associated with schizophrenia (e.g., in suicidal patients; suicidiality), agitation, attention deficit disorder (ADD) and attention deficit hyperactivity disorder (ADHD), atypical psychosis, mania, schizophreniform disorder, drug- or substance-induced psychotic disorder, schizoaffective disorder, cluster A personality disorders, delusional disorder, and brief psychotic disorder. Compounds, salts and compositions of the invention can be used alone, in combination therapy, i.e., with each other or in combination with other agents, e.g., antidepressants, antipsychotics, etc. The invention also relates to combination therapy utilizing compounds, salts and composition of the invention with nicotine.

"Combination therapy" (or "co-therapy") includes the administration of a compound, salt or composition of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Combinations of the compounds of the present invention and the other active agents may be administered together in a single combination or separately. Where separate administration is employed, the administration of one element may be prior to, concurrent with, or subsequent to the administration of other agents. Administration of these therapeutic agents in combination typically is carried out over a defined time period (usually minutes, hours, days or weeks depending upon the combination selected). In one embodiment, "combination therapy" encompasses the administration of two or more of these therapeutic agents as part of separate monotherapy regimens that incidentally and arbitrarily result in the combinations of the present invention. In another embodiment, "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also embraces the administration of the therapeutic agents as described above in further combination with other biologically active ingredients and non-drug therapies (e.g., surgery, radiation treatment, or a medical device). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

"Treating" includes any effect, e.g., lessening, reducing, modulating, or eliminating, that results in the improvement of the condition, disease, disorder, etc. "Treating" or "treatment" of a disease state includes: (1) preventing the disease state, i.e., causing the clinical symptoms of the disease state not to develop in a subject that may be exposed to or predisposed to the disease state, but does not yet experience or display symptoms of the disease state; (2) inhibiting the disease state i.e., arresting the development of the disease state or its clinical symptoms; or (3) relieving the disease state, i.e., causing temporary or permanent regression of the disease state or its clinical symptoms. "Disease state" means any disease, condition, symptom, or indication.

As used herein, the term "sleep disorder" includes conditions recognized by one skilled in the art as sleep disorders, for example, conditions known in the art or conditions that are proposed to be sleep disorders or discovered to be sleep disorders. A sleep disorder also arises in a subject that has other medical disorders, diseases, or injuries, or in a subject being treated with other medications or medical treatments, where the subject, as a result, has difficulty falling asleep and/or remaining asleep, or experiences unrefreshing sleep or non-restorative sleep, e.g., the subject experiences sleep deprivation. Treating a sleep disorder with one or more compounds, salts or compositions herein, alone or in combination, also includes treating a sleep disorder component of other disorders, such as CNS disorders (e.g., mental or neurological disorders such as anxiety).

Dosage rates and routes of administration of the disclosed compounds are similar to those already used in the art and known to the skilled artisan (see, for example, Physicians' Desk Reference, 54th Ed., Medical Economics Company, Montvale, N.J., 2000).

The compounds of general Formulae I, III, IV and -V of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formulae I, III, IV and -V and a pharmaceutically acceptable carrier. One or more compounds of general Formulae I, III, IV and -V may be present in association with one or more non-toxic pharmaceutically acceptable carriers and/or diluents and/or adjuvants, and if desired other active ingredients, e.g., other antidepressant or antipsychotic drugs. The pharmaceutical compositions containing compounds of general Formulae I, III, IV and -V may be in a form suitable for oral use, for example, as tablets, troches, lozenges, aqueous or oily suspensions, dispersible powders or granules, emulsion, hard or soft capsules, or syrups or elixirs and as such, may be combined with at least one pharmaceutically acceptable glidant, solvent, adjuvant, diluent, lubricant, excipient, or combination thereof.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed. Further, delayed release formulations without one or more coatings may be prepared.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulae I, III, IV and -V may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formulae I, III, IV and -V may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The formulations may also be applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Dosage levels of the order of from about 0.1 mg to about 140 mg per kilogram of body weight per day are useful in the treatment of the conditions indicated below (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a pre-mix for addition to the feed or drinking water.

EXAMPLE 1

Preparation of Compound K and Additional Esters

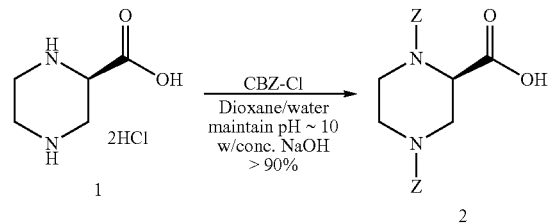

In a 2 liter 3-neck flask, dissolve 20 g (98.5 mmol) of R-piperazinecarboxylic acid dihydrochloride (1) in 500 mL water and 500 mL stabilized dioxane. Cool with an ice bath and add phenolphthalein indicator. Using an addition funnel, add conc. NaOH to pH 10 (solution just turns pink). Using a second addition funnel, add 30.6 mL (216.7 mmol) benzyl chloroformate in portions while maintaining the pink color (pH 10) with conc. NaOH. Add more phenolphthalein halfway through the addition which takes about 0.5 hr. Stir overnight at room temperature (RT). Extract with 1 liter of ether. Acidify the ice cooled aqueous layer with 6 N HCl and extract with ethyl acetate. Wash with brine and dry over magnesium sulfate. Concentrate to about 40 g oil. No loss of optical purity was confirmed by chiral HPLC.

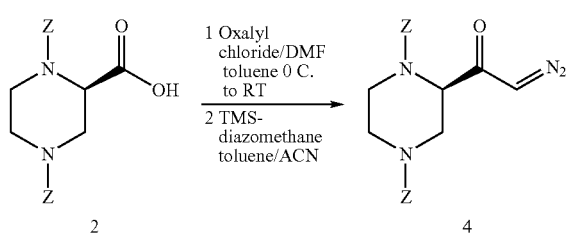

Dissolve 19.5 g (49.0 mmol) 2 in 200 mL anhydrous toluene (SM can be azeotropically dried with toluene if necessary). Chill over ice, under nitrogen. Add 1 mL DMF and 8.55 mL (98.0 mmol) oxalyl chloride over 1 min. Stir cold about 1 hour then at RT for about 1.5 hr. Gently sparge with nitrogen to remove HCl. Check for remaining SM by quenching a sample with pyrrolidine, shaking with a dilute HCl solution. and ethyl acetate (EA). TLC the EA layer using 50:10:1 DCM/MeOH/NH$_4$OH. Additional oxalyl chloride is added as necessary to consume all SM. Decant or filter if necessary (toluene wash) discarding insoluble material. Concentrate at about 30 C to an orange syrup. Dissolve in 200 mL anhydrous acetonitrile and chill over ice, under nitrogen. A 2M solution of TMS-diazomethane/ether is added rapidly. After a brief induction period, nitrogen is evolved. Stir cold for about 1 hour and concentrate at 40 C to an oil. Dissolve in EA and wash with sodium bicarbonate solution, brine, and dry over sodium sulfate. The sample was concentrated to about 21 g amber syrup. Use directly.

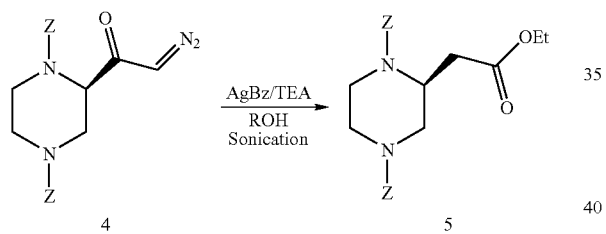

Dissolve 21 g (~49 mmol) 4 in 200 mL ethanol. Add a solution of 2.2 g (9.8 mmol) silver benzoate in 27 mL (196 mmol) TEA while reaction mixture is sonicated in a standard water bath sonicator. Addition is completed in about 5 minutes, pausing several times to swirl the mixture. Nitrogen is evolved and a brown ppt forms. Sonicate for about 15 minutes then concentrate to an oil. Dissolve in EA and filter through a plug of silica. The described sample was chromatographed on 250 g silica eluting with 1:1 EA/hexane to give 18.4 g lt. brown oil.

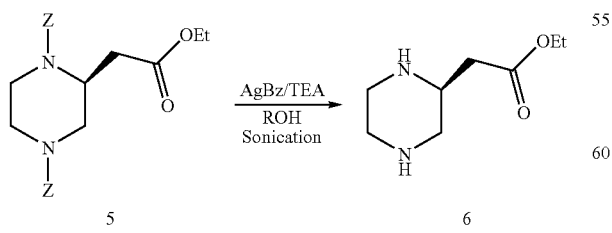

Dissolve 18 g (39 mmol) of 6 in 400 mL EtOH and add 1.8 g 10% Pd/C as a slurry in EtOH. Hydrogenating on a Parr apparatus for about 12 hours, then filtering through celite and concentrating yielded about 5.2 g oil, which forms a waxy crystalline solid on standing. Use as is.

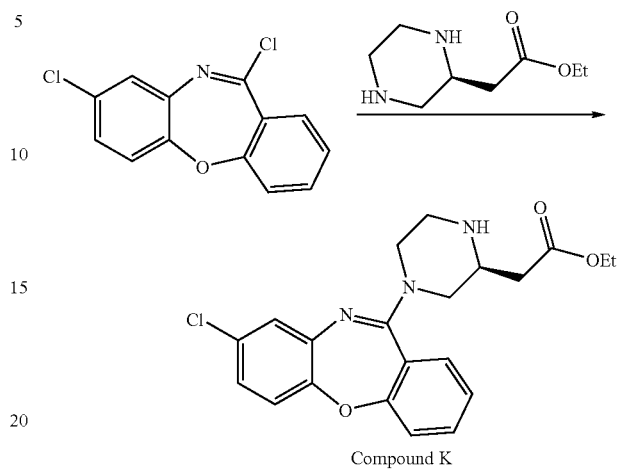

Combine 5 g (29 mmol) of ethyl piperazine-2-acetate, 4.7 g (29 mmol) chloroimidate and 12 ml, 3 eq. TEA in 100 mL EA/20 ml EtOH and heat at about 80 C for about 36 hours. The reaction mixture is then concentrated on rotovap, partitioned between EA and dil. sodium carbonate solution, and washed with brine. Dry over sodium sulfate. Chromatographing on silica gel, eluting with 1% (10% TEA/EtOH)/EA to remove remaining starting material and increasing to 3% (10% TEA/EtOH) then 5% (10% TEA/EtOH), yielded 4.2 g product as a yellow foam.

EXAMPLE 2

Preparation of Additional 3'-(S) Substituted Esters

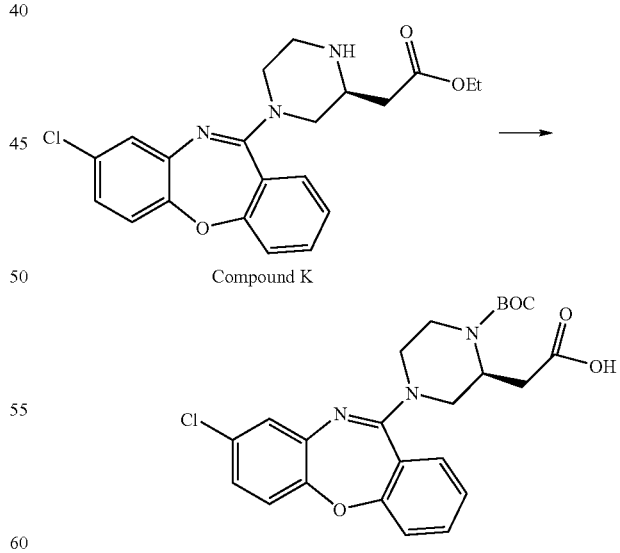

Dissolve 1.2 g (3 mmol) Compound K in 30 ml THF. Add 720 mg (3.3 mmol) BOC-anhydride and heat at RT for about 5 hrs, then at 80 C for about 12 hr. Cool over ice and add 30 ml MeOH and 10 ml of 4 N KOH solution and stir RT overnight. Adjust to pH 3 with 1 M citric acid solution and extract into MTBE. Wash with brine and dry over sodium sulfate. Con-

EXAMPLE 3

Preparation of Compound ED

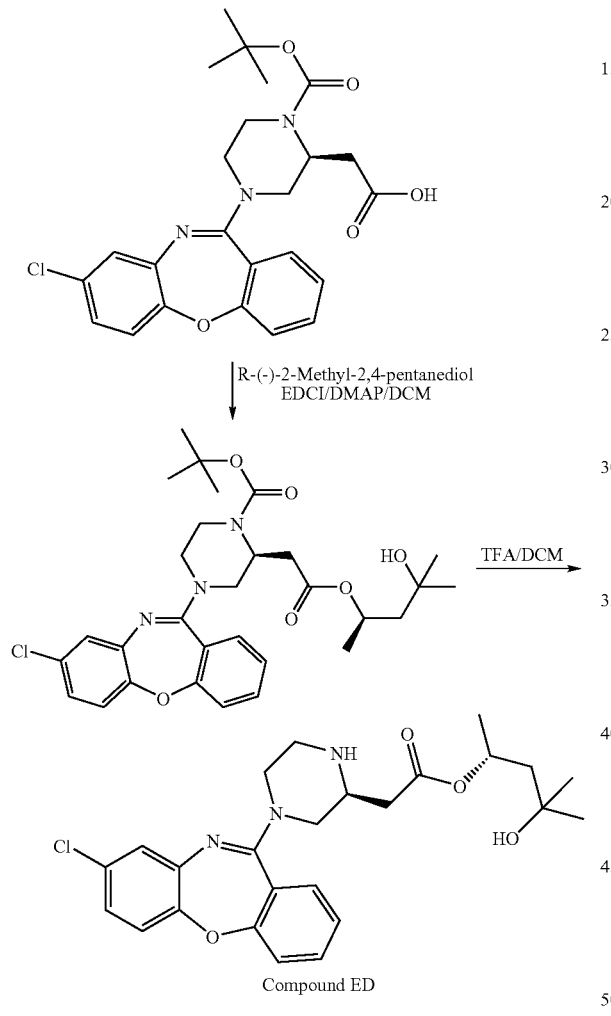

Compound ED (S)-2-(1-(tert-butoxycarbonyl)-4-(8-chlorodibenzo[b,f][1,4]oxazepin-11-yl)piperazin-2-yl)acetic acid (288 mg, 0.61 mmol) can be dissolved in DMF (5 ml). 1-(3-Dimethylaminopropyl)-3-ethylcarbodiimide hydrochloride (222 mg, 1.16 mmol), and 4-Dimethylaminopyridine (48 mg, 0.39 mmol) can be added respectively at room temperature under nitrogen. After about fifteen minutes R-(−)-2-Methyl-2,4-pentanediol (92 mg, 0.78 mmol) can be added and the mixture should be heated to about 50 C under nitrogen. The product can be purified by flash chromatography using 10% Acetone/Dichloromethane as the eluent to give (S)-tert-butyl 4-((E)-8-chlorodibenzo[b,f][1,4]oxazepin-11-yl)-2-(2-((R)-4-hydroxy-4-methylpentan-2-yloxy)-2-oxoethyl)piperazine-1-carboxylate. (S)-tert-butyl 4-((E)-8-chlorodibenzo[b,f][1,4]oxazepin-11-yl)-2-(2-((R)-4-hydroxy-4-methylpentan-2-yloxy)-2-oxoethyl)piperazine-1-carboxylate can be dissolved in dichloromethane (1.1 ml) and cooled in an ice bath. Trifluoroacetic acid (0.5 ml) should be added drop wise under nitrogen and slowly allowed to reach room temperature while running overnight. The mixture should be concentrated under vacuum and purified by flash chromatography using 10% Acetone/Dichloromethane as the eluent to give Compound ED.

EXAMPLE 4

Preparation of Compound EK

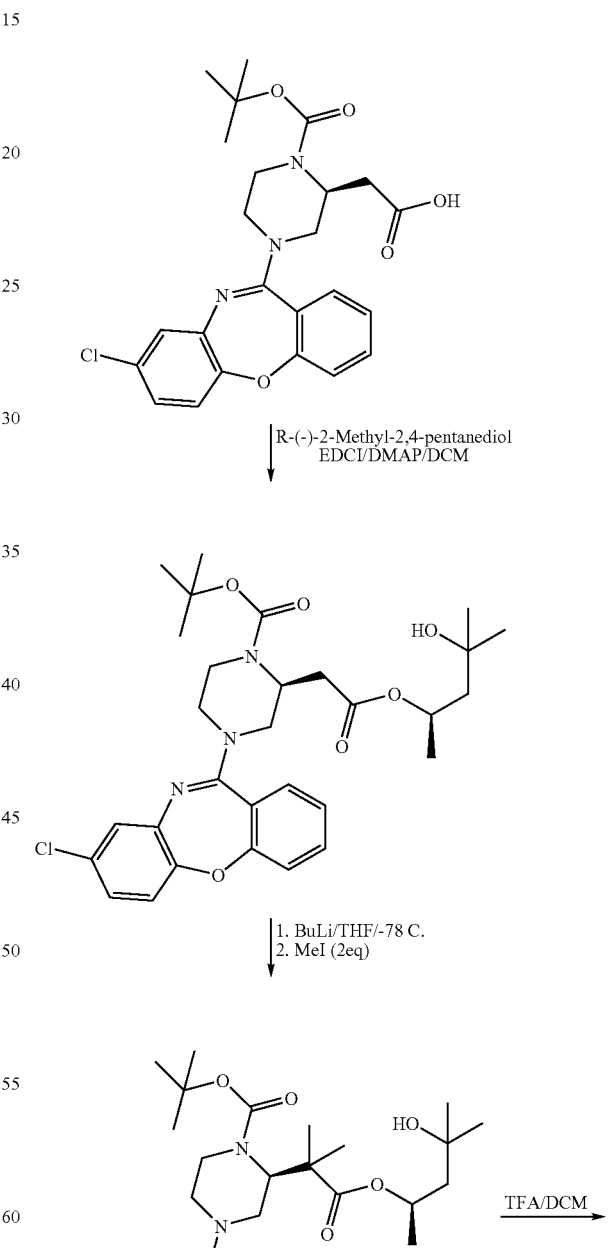

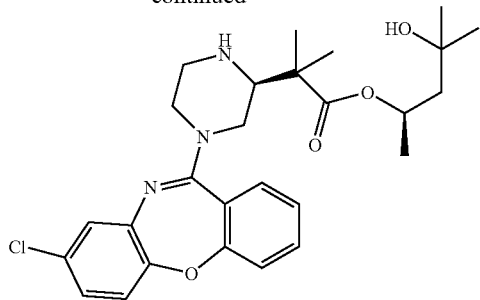

(S,E)-2-(1-(tert-butoxycarbonyl)-4-(8-chlorodibenzo[b,f][1,4]oxazepin-11-yl)piperazin-2-yl)acetic acid (300 mg, 0.60 mmol) can be dissolved in DMF (0.25M). 1-(3-Dimethylaminopropyl)-3-ethylcarbodiimide hydrochloride (0.9 mmol), and 4-Dimethylaminopyridine (0.3 mmol) may be added respectively at room temperature under nitrogen. After about fifteen minutes R-(−)-2-Methyl-2,4-pentanediol (0.60 mmol) may be added and the mixture heated to about 50° C. under nitrogen. The product can be worked up as usual and purified by flash chromatography using 10% Acetone/Dichloromethane as the eluent to give (S)-tert-butyl 4-((E)-8-chlorodibenzo[b,f][1,4]oxazepin-11-yl)-2-(2-((R)-4-hydroxy-4-methylpentan-2-yloxy)-2-oxoethyl)piperazine-1-carboxylate as a white foam. The (S)-tert-butyl 4-((E)-8-chlorodibenzo[b,f][1,4]oxazepin-11-yl)-2-(2-((R)-4-hydroxy-4-methylpentan-2-yloxy)-2-oxoethyl)piperazine-1-carboxylate may be dissolved in anhydrous THF and cooled in a dry ice acetone bath under nitrogen. A 2.0M solution of Butyl lithium in cyclohexane (about 1 mole equivalent) may be added dropwise under nitrogen. After about 15 minutes, iodomethane (about 1 mole equivalent) may be added dropwise under nitrogen. After about one hour, a 2.0M solution of Butyl lithium in cyclohexane (about 1 equivalent) may be added dropwise under nitrogen. After about 15 minutes, iodomethane (about 1 equivalent) may be added dropwise under nitrogen. After about one hour the solution may be concentrated under vacuum to give (S)-tert-butyl 4-((E)-8-chlorodibenzo[b,f][1,4]oxazepin-11-yl)-2-(1-((R)-4-hydroxy-4-methylpentan-2-yloxy)-2-methyl-1-oxopropan-2-yl)piperazine-1-carboxylate as a white foam. The (S)-tert-butyl 4-((E)-8-chlorodibenzo[b,f][1,4]oxazepin-11-yl)-2-(1-((R)-4-hydroxy-4-methylpentan-2-yloxy)-2-methyl-1-oxopropan-2-yl)piperazine-1-carboxylate may be dissolved in dichloromethane (about 1.1 ml) and cooled in an ice bath. Trifluoroacetic acid (about 0.5 ml) may be added dropwise under nitrogen and slowly allowed to reach room temperature while running overnight. The mixture may be concentrated under vacuum and purified by flash chromatography using 10% Acetone/Dichloromethane as the eluent to give Compound EK.

EXAMPLE 5

Preparation of gemdimethylated 3' esters: (S,E)-2-(1-(tert-butoxycarbonyl)-4-(8-chlorodibenzo[b,f][1,4]oxazepin-11-yl)piperazin-2-yl)acetic acid can be dissolved in DMF (0.25M). 1-(3-Dimethylaminopropyl)-3-ethylcarbodiimide hydrochloride (0.9 mmol), and 4-dimethylaminopyridine (about 0.5 mole equivalents) can be added respectively at room temperature under nitrogen. After about fifteen minutes, the alcohol (to make the relevant ester, e.g., propanol for a propyl ester (about 1 equivalent)) should be added and the mixture should be heated to about 50° C. under nitrogen. The product can be worked up as usual and purified by flash chromatography using standard acetone/dichloromethane as the eluent to give the BOC protected ester. The BOC protected ester may be dissolved in anhydrous THF and cooled in a dry ice acetone bath under nitrogen. A 2.0M solution of Butyl lithium in cyclohexane (about 1 mole equivalent) may be added dropwise under nitrogen. After about 15 minutes, iodomethane (about 1 mole equivalent) may be added dropwise under nitrogen. After about one hour, a 2.0M solution of Butyl lithium in cyclohexane (about 1 equivalent) may be added dropwise under nitrogen. After about 15 minutes, iodomethane (about 1 equivalent) may be added dropwise under nitrogen. After about one hour the solution may be concentrated under vacuum to give the gemdimethyl product. The BOC protected gemdimethyl product can be dissolved in dichloromethane (1.1 ml) and cooled in an ice bath. Trifluoroacetic acid (0.5 ml) should be added dropwise under nitrogen and slowly allowed to reach room temperature while running overnight. The mixture should be concentrated under vacuum and purified by flash chromatography using standard acetone/dichloromethane as the eluent to give free base gemdimethyl product.

EXAMPLE 6

Preparation of compound BW, BX racemate: Mono(S,E)-tert-butyl 4-(8-chlorodibenzo[b,f][1,4]oxazepin-11-yl)-2-(2-ethoxy-2-oxoethyl)piperazine-1-carboxylate should be dissolved in anhydrous THF and cooled to −78 C under nitrogen. Butyllithium should be added dropwise in hexane. After about 30 mins methyl iodide (0.95 eq) should be added and allowed to slowly reach room temperature. The mixture should be concentrated under vacuum and purified by flash chromatography using standard acetone/dichloromethane as the eluent to give free base monomethyl BOC protected product. The BOC protected monomethyl product should be dissolved in dichloromethane and cooled in an ice bath. Trifluoroacetic acid should be added dropwise under nitrogen and slowly allowed to reach room temperature while running overnight. The mixture should be concentrated under vacuum and purified by flash chromatography using standard acetone/dichloromethane as the eluent to give free base monomethyl product. See scheme for Example 7 below.

EXAMPLE 7

Preparation of Compound CC

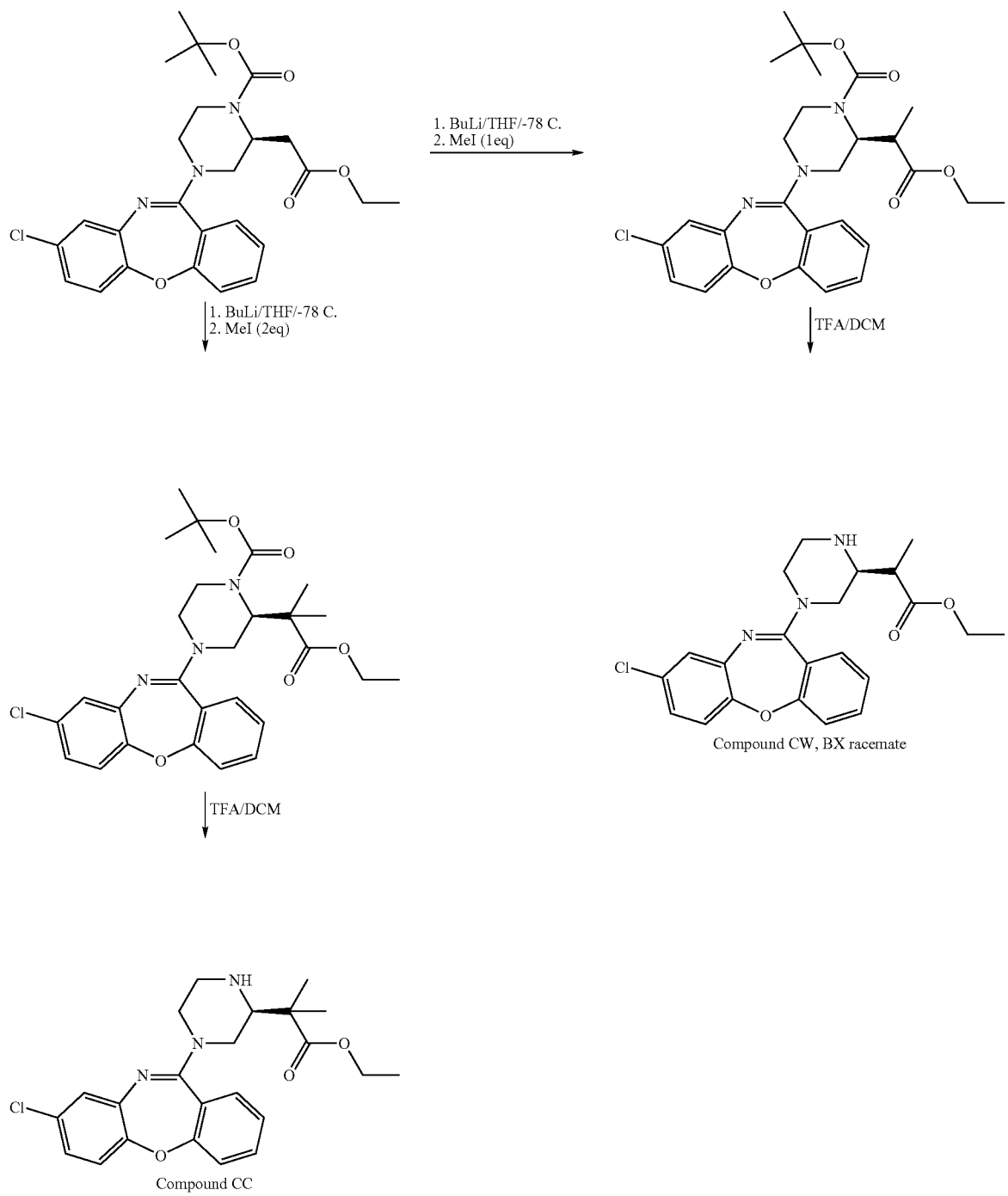

Mono(S,E)-tert-butyl 4-(8-chlorodibenzo[b,f][1,4]oxazepin-11-yl)-2-(2-ethoxy-2-oxoethyl)piperazine-1-carboxylate should be dissolved in anhydrous THF and cooled to −78 C under nitrogen. Butyllithium should be added dropwise in hexane. After about 30 mins methyl iodide (about 2.2 eq) should be added and allowed to slowly reach room temperature. The mixture should be concentrated under vacuum and purified by flash chromatography using standard acetone/dichloromethane as the eluent to give free base gemdimethyl BOC protected product. The BOC protected gemdimethyl product should be dissolved in dichloromethane and cooled in an ice bath. Trifluoroacetic acid should be added drop wise under nitrogen and slowly allowed to reach room temperature while running overnight. The mixture should be concentrated under vacuum and purified by flash chromatography using standard acetone/dichloromethane as the eluent to give free base gemdimethyl product.

EXAMPLE 8

Preparation of Compound N and Compound P Racemate

Preparation of (E)-8,11-dichlorodibenzo[b,f][1,4]oxazepine

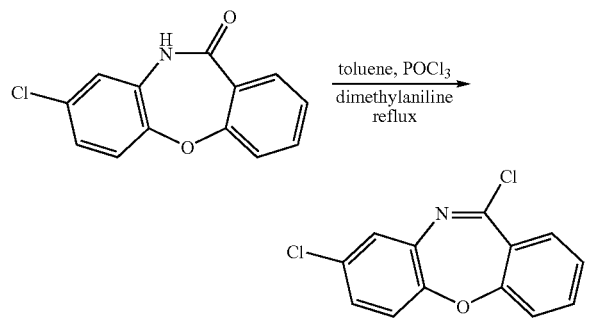

Phosphorus oxychloride (40 mL) and dimethylaniline (7.6 mL, 60 mmol) were added to a solution of amide (7.35 g, 30 mmol) in toluene (120 mL) under nitrogen. Fit with condenser and heat at reflux under nitrogen overnight. The reaction was heated at 100° C. for about 48 h. The reaction was then cooled and diluted with toluene (100 mL), then distilled rapidly at 150° C. to approximately half of the initial volume. The reaction was diluted again with toluene (120 mL) and distilled again to remove excess phosphorus oxychloride. The reaction was cooled and toluene (150 mL) was added, then the mix was poured into ethyl acetate (200 mL). The reaction was washed with 1M HCl solution, and dried over MgSO$_4$, then used immediately as a solution in toluene/ethyl acetate.

Preparation of Substituted Piperizine

1. Preparation of Ethyl 1,4-dibenzylpiperazine-2-carboxylate

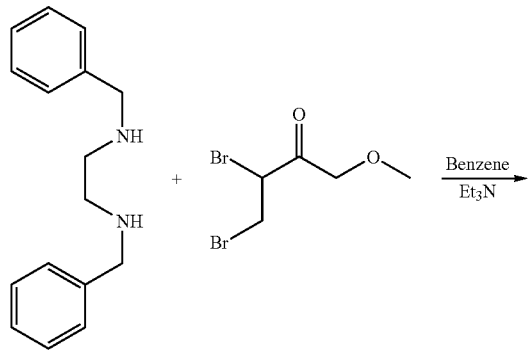

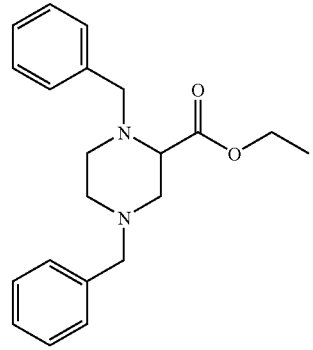

To a hot (about 80° C.) solution of N,N'-dibenzylethylenediamine (216 g, 0.9 mol) and triethylamine (300 uL, 2.16 mol) in toluene (650 mL) was added rapidly dropwise ethyl 2,3-dibromopropionate (240 g, 0.93 mol) in toluene (650 mL). After the addition, the reaction mixture was stirred at 80° C. for about three hours. A temperature below about 95° C. was maintained. The heavy precipitate was filtered off and then solvent and excess TEA removed. t-butyl methyl ether (about 300 mL) was added. The reaction was stirred well, and any precipitate that was formed was filtered. The reaction was concentrated to a pale yellow oil (about 287 g, about 94%)

2. Preparation of 1,4-Dibenzyl-2-(hydroxymethyl)piperazine

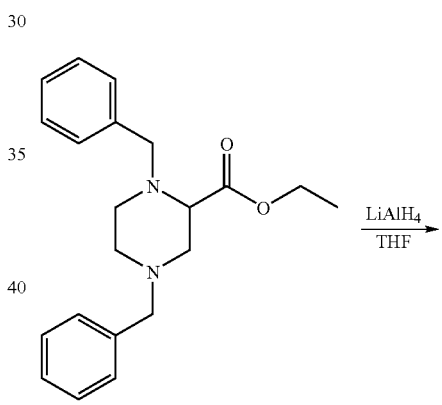

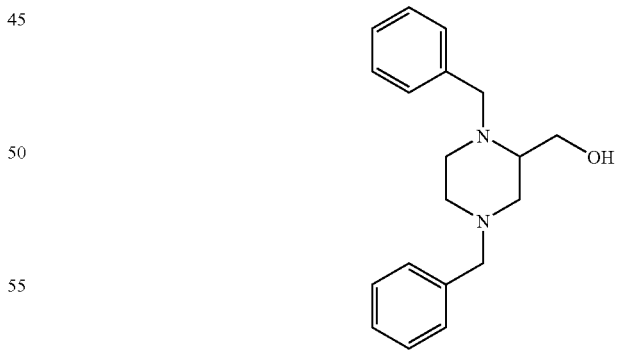

To a stirred ice cold (0° C.) solution of LAH (2.0 M in THF, 2 mL, 4.0 mmol) in THF (20 mL), was added a solution of ester (1.8 g, 5.3 mmol) dropwise over 15 minutes. The mixture was stirred for about 20 hours at room temperature, then cooled and treated carefully with wet ether and aqueous NaOH (0.5 M, 200 mL) until no more reaction occurred upon addition. The aqueous layer was extracted with ether, and the extracts were dried over NaSO$_4$. The reaction was concentrated to a clear oil (1.55 g, 99%).

3. Preparation of 1,4-Dibenzyl-2-(chloromethyl)piperazine

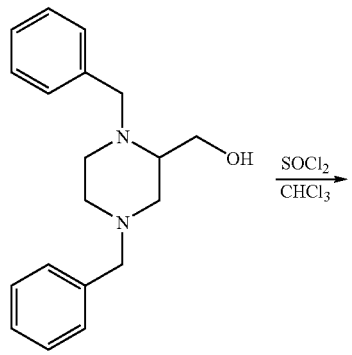

The alcohol (1.6 g, 5.3 mmol) was dissolved in chloroform (50 mL) and cooled to 0° C. (ice bath). A solution of thionyl chloride (3.0 mL, 40.3 mmol) in chloroform (about 20 mL) was added dropwise over about 5 minutes. The reaction was allowed to warm to room temperature and monitored by TLC. A reaction flask was fitted with a condenser, and the reaction was heated at reflux for about 15 hours. The reaction mixture was cooled and diluted with dichloromethane, then washed with saturated sodium bicarbonate solution and dried over NaSO$_4$. The product was filtered and concentrated to a yellow oil.

4. Preparation of 1,4-Dibenzyl-2-(cyanomethyl)piperazine

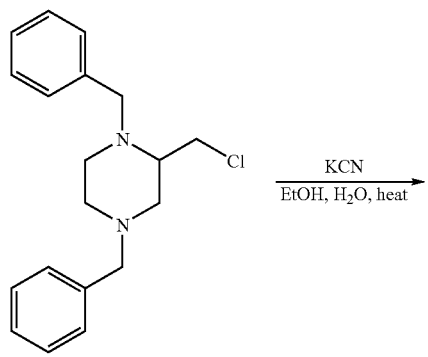

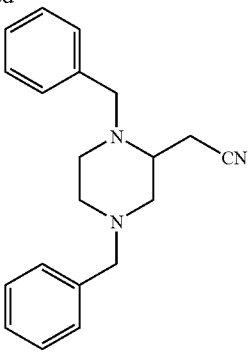

To a refluxing solution of KCN (4.0 g, 61.5 mmol) in water (75 mL) and ethanol (80 mL) was added dropwise a solution of the previous step's halide (12.7 g, 40.3 mmol) in ethanol (20 mL). The mixture was stirred and refluxed for about 7 hours, then concentrated to remove ethanol. The crude residue was taken up in dichloromethane, washed with water, and dried over MgSO$_4$. The product was filtered and concentrated to 12 g orange oil, which was then purified on silica using flash chromatography with 4:1 Hex/EtOAc.

5. Preparation of Methyl 1,4-Dibenzylpiperazin-2-ylacetate

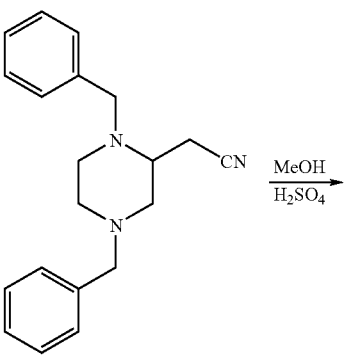

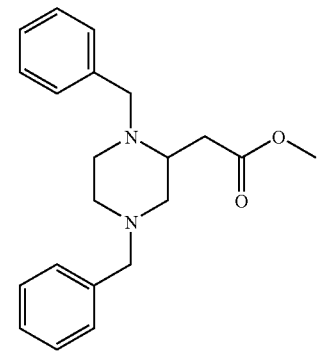

The nitrile from the previous step (0.3 g, 0.98 mmol) was dissolved in methanol (about 30 mL), to which concentrated sulfuric acid (5 mL) was added. The reaction was fitted with a condenser and heated at reflux overnight and monitor the reaction by TLC. Additional sulfuric acid (8 mL) was added and the mixture heated at reflux about 20 hours. The reaction was cooled and poured into dichloromethane and water. The pH was carefully neutralized by adding saturated sodium bicarbonate solution to pH 9. The resulting product was extracted into dichloromethane and dried over MgSO$_4$ then filtered and concentrated to obtain a clear oil (0.3 g, 91%).

6. Preparation of methyl piperazin-2-ylacetate

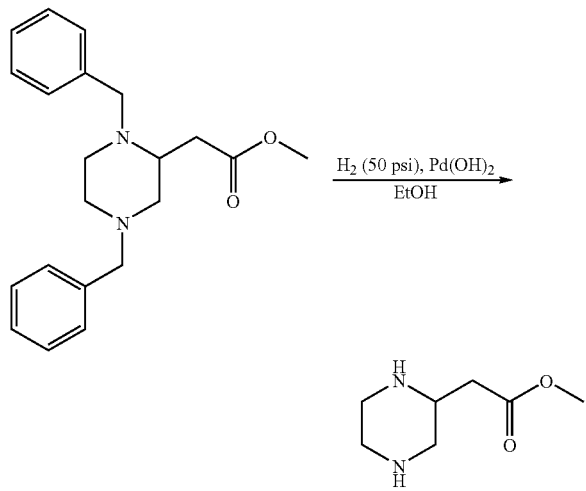

The dibenzyl piperizine ester (0.87 g, 2.5 mmol) was dissolved in ethanol (10 mL) and added to Parr shaker flask. Palladium hydroxide (20 wt % Pd on carbon, 0.54 g) was added. The flask was evacuated with H$_2$ (3×) and shaken under H$_2$ (50 psi) for about 15 hours. The product was filtered through a filter disc (Whatman 0.7 um) to remove palladium on carbon, and then concentrated to a yellow oil.

7. Coupling of Core to Substituted Piperizine

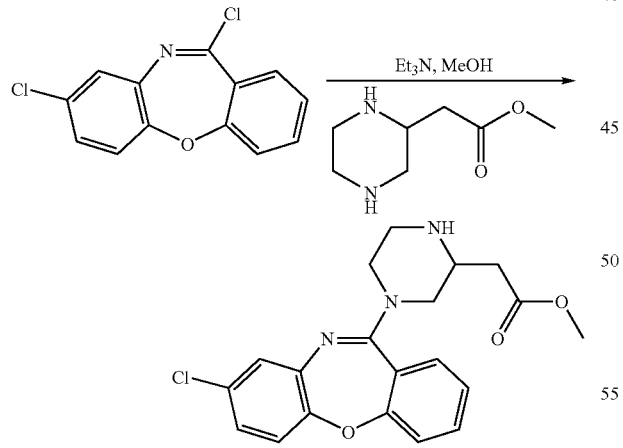

Triethylamine (14 mL, 100 mmol) was added to a solution of piperizine ester (6.3 g, 40.1 mmol) in methanol (25 mL) under nitrogen. The reaction mixture heated to 50° C., and a solution of chloroimidate in toluene/ethyl acetate (650 mL, 0.46M) was added over about 30 seconds with stirring. The reaction was fitted with a condenser and heated at about 90° C. (reflux) with stirring overnight. The reaction mixture was cooled then methanol (30 mL) and triethylamine (15 mL) were added. The reaction was sonicated for about 2 minutes and heated at reflux for additional 7 hours. The reaction mixture was cooled and diluted with ethyl acetate (250 mL), washed with saturated bicarbonate solution, and dried over Na$_2$SO$_4$. The reaction was filtered and concentrated to about 100 mL of crude product in toluene, which was filtered to remove white solid precipitate, and purified by silica gel chromatography (230-400 mesh) using 1:1 hexanes/ethyl acetate and 100:10:1 dichloromethane/MeOH/NH$_4$OH gradient elution. The main fraction was isolated and concentrated to obtain 3.84 g (10 mmol, 33% yield) light yellow foam of high purity (99% by HPLC).

EXAMPLE 9

Preparation of Compound FS: The ethyl ester (400 mg, 1.0 mmol) was dissolved in amine (1.5 mL, 20 mmol) in a 20 mL vial and heated at 90° C. with stirring for about 48 hours. The reaction mixture was cooled and purified directly by HPLC using acetonitrile/water. The collected fractions were frozen and lyophilized to yield Compound FS as a white solid (95 mg, 22%).

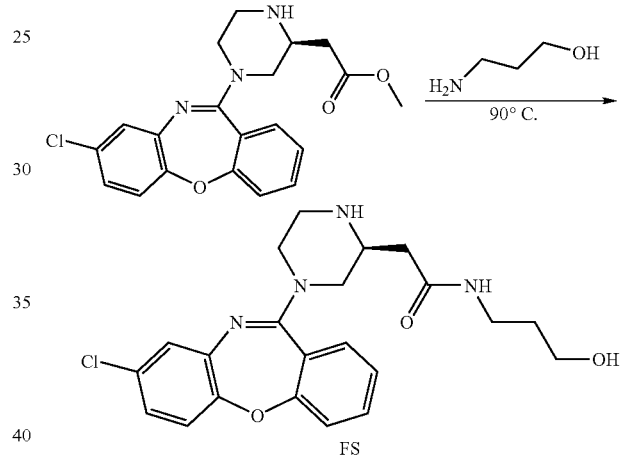

EXAMPLE 10

Methods

Neuronal Cultures. Cerebral cortices were dissected from newborn rats and treated with 0.25% trypsin to dissociate the cells. Dissociated cells were resuspended in Dulbecco's Modified Eagle's Medium (DMEM) containing 10% plasma derived horse serum (PDHS) and were plated in poly-L-lysine-coated, 35 mm Nunc plastic tissue culture dishes (3.0× 10$^6$ cells/dish/2 ml media). Cultures were maintained in an atmosphere of 5% CO2/95% air.

Acute Effects of Compounds of the invention on NMDA Receptor Function

Electrophysiological recordings: Voltage-clamp recordings of membrane ionic currents were conducted by using Axopatch 200B and Axoclamp ID amplifiers (Axon Instruments, Foster City, Calif.). Neurons were used for electrophysiological recordings between 12 and 20 days in vitro. If a neuron showed either a marked change in holding current or a noticeable alteration in amplitude or shape of capacitance transients during the experiment, the data from that neuron were discarded. Patch microelectrodes were pulled from 1.5 mm borosilicate glass tubing using a two-stage vertical pipette puller (Narishige, East Meadow, N.Y.). When filled with recording solution, patch microelectrodes will have a resistance of 3-5 MΩ. For rapid application of agonist-containing solutions to neurons, the SF-77B system (Warner Instrument Corp., Hamden, Conn.) were used. Otherwise a slower exchange of extracellular solution were done by a home-made bath-application system.

NMDA receptor activity was measured as the standard deviation (SD) of membrane current. To study acute effects of drugs the SD of membrane current were measured in vehicle control solution and in the presence of different concentrations of drugs (1-100 µM). For screening purposes, 1 and 10 µM were used for most compounds. For lead compounds and classic comparators (e.g., clozapine), complete concentration-response curves were created. Drugs were applied at least for 10 min. The vehicle control was monitored at the same period of time. To measure functional changes in the NMDA receptor function during chronic exposure of drugs the currents evoked by saturating concentration of NMDA (1 mM) were recorded in drug treated and control culture. After plating neurons for 5-7 days, half of culture dishes were treated with a fixed concentration of drug and other half with vehicle only. The recordings were preformed after 7-14 days of drug application. The Amplitude of NMDA-induced currents in vehicle control and treated cultures were compared. The SD of membrane current and NMDA-induced currents were recorded in TTX-containing (0.3-1 µM) extracellular solution. In case of NMDA receptor-mediated mEPSC recordings, $Mg^{2+}$ was omitted from the extracellular solution. In order to isolate the NMDA component of glutamate receptor-mediated currents, the non-NMDA (AMPA/kainate) receptor antagonist NBQX (10-20 µM) were added to extracellular solutions, Vh=−60 mV. The NMDA-induced currents were recorded at −30 mV in the presence of physiological concentration of Mg2+ (1 mM). Strychnine (1 µM) and picrotoxin (100 µM) were added in all cases to the extracellular solution to block glycine and GABA receptors, respectively. The basic extracellular solution contained (in mM): NaCl (140), KCl (4), $CaCl_2$ (2), $MgCl_2$ (1), 4-(2-hydroxyethyl)-1-piperazineethanesulfonic acid (HEPES) (10), and glucose (11). The pH of the extracellular solution were adjusted to 7.4 using NaOH. The main solution for filling the patch electrodes contain (in mM): Cs gluconate (135), NaCl (5), KCl (10), $MgCl_2$ (1), $CaCl_2$ (1), EGTA (11), HEPES (10), $Na_2$ATP (2), $Na_2$GTP (0.2) mM. The pH of the intracellular solution were adjusted to 7.4 using CsOH. Various concentrations of clozapine and ATI-compounds were added to the extracellular solution according to the protocols described.

The digitized data were analyzed off-line using the Mini-Analysis Program (Synaptosoft, Leonia, N.J.) or pCLAMP9 (Axon Instruments, Union City, Calif.).

EXAMPLE 11

Acute Effects of ATI-9000 Compounds on GABAA Receptor Function Electrophysiological Recordings To study the effect of ATI-9000 compounds on GABA receptor-mediated mIPSCs, bicuculline (20 µM) in the extracellular solution and Cs gluconate (135 mM) in the intrapipette solution, which were used for the NMDA receptor experiments, were replaced with 1,2,3,4-tetrahydro-6-nitro-2,3-dioxo-benzo[f]quinoxaline-7-sulfonamide (NBQX; 5-10 µM) and with KCl (135 mM), respectively. All IPSCs were recorded at a holding potential of −60 mV. The digitized data were analyzed off-line using the Mini-Analysis Program (Synaptosoft, Leonia, N.J.) with a detection threshold for a mEPSC amplitude set at ≧8 pA.

EXAMPLE 12

Compound K, But not Compound Q, Binds to $D_{2S}$ and $D_{2L}$ Dopamine Receptors The $D_2$ receptors are known to be a receptor subtype involved in the activity of clozapine. Compound K has low micromolar $IC_{50}$ binding affinity for $D_{2S}$ and $D_{2L}$ receptors. The affinity of Compound K for the $D_{2S}$ and $D_{2L}$ receptors was comparable to the affinity of clozapine for these receptors.

Compound K and its metabolite Compound Q also bind to Hi, $5\text{-}HT_{1A}$ and $5\text{-}HT_{2C}$, but with very low affinity to $M_3$ and Ml receptors. The affinity of Compound K for the $H_1$ and $5\text{-}HT_{2C}$ receptors was 69- and 1.2-fold lower than clozapine and 4-fold higher for the $5\text{-}HT_{1A}$ receptors.

Radioligand Binding Assay Methodology

Consistent with standard competition radioligand binding assays, the methodology was based on displacement of radioligand from tissues (or cell lines) bearing the receptor of interest (Cheng, Y. and Prusoff, W. H. (1973). Biochem. Pharmacol. 22, 3099-3108). The measurements were based on the binding of a single concentration of radiolabeled ligand in the presence of various concentrations of unlabeled ligand.

Tissues (or cellular plasma membrane fractions) were incubated in the presence of radioligand at equilibrium and in the presence of a range of concentrations of the test compounds (which were non-radiolabeled), and the displaced radioligand was separated from the membranes by filtration. Nonspecific binding was assessed by measuring displacement of the radioligand in the presence of a compound known to block binding of the radioligand to the receptor. Finally, the concentration-response relationship for radioligand displacement (corrected for non-specific binding) was used to assess binding of the test compound to the receptor.

Protocol conditions are summarized in Table 1 (FIG. 9).

EXAMPLE 13

Compound K is a Partial Agonist at Human $D_{2S}$ Receptor

In vitro assays were performed based on adenylyl cyclase stimulation in cells engineered to stably express human $D_{2S}$ receptor. Compound K appeared to be a partial $D_2$ receptor agonist and a $D_2$ receptor antagonist, like clozapine. The estimated $IC_{50}$ of Compound K is 13 µM.

Adenylyl Cyclase Methodology

HitHunter™ cAMP XS (DiscoveRx, Calif.) is a chemiluminescent assay ideally suited for monitoring Gi-coupled GPCRs with robust signal to background ratios for both agonist and antagonist responses. It is an in-vitro based competitive immunoassay. Free cAMP from cell lysates compete for antibody binding against labeled ED-cAMP conjugate, a small peptide fragment of β-galactosidase (β-gal). In the absence of free cAMP, ED-cAMP conjugates are captured by the antibody and are unavailable for complementation, resulting in low signal. In the presence of free cAMP, antibody sites are occupied, leaving ED-cAMP conjugate free to complement with EA, forming active β-gal EFC enzyme for substrate hydrolysis to produce a chemiluminescent signal. A positive signal is generated in direct proportion to the amount of free cAMP bound by the antibody.

HEK 293 cells expressing functional human $D_{2S}$ receptors (Scottish Biomedical) were harvested and resuspended with PBS buffer (serum-free medium). The cells were plated in a 96-well plate at 20,000 cells/well. Serial dilutions of forskolin and dopamine were tested (positive controls for the agonist assay). Serial dilutions of proprietary compounds were tested at a 10 µl volume in the presence of 27 µM forskolin (agonist assay) or in presence of both 27 µM forskolin and 30 nM dopamine (antagonist assay). The plates were incubated at 37° C. for 30 minutes. After cell induction, the assay reagents were added and incubated for 60 minutes at room temperature. The luminescence was read using a TopCount NXT detector (PerkinElmer).

EXAMPLE 14

Compound K is a Potent 5-$HT_{2A}$ Receptor Antagonist

The ability of antipsychotic drugs to affect 5-$HT_{2A}$ receptor function has been widely suggested to contribute to their therapeutic properties. Compound K is a potent antagonist for 5-HT2A receptors ($pA_2$=8.5), comparable to clozapine ($pA_2$=8.4). The affinity of Compound Q for the 5-$HT_{2A}$ receptors was 8-fold lower than Compound K. See FIG. 1.

Organ Bath Methodology

The rat aorta (approximately 7 cm) was isolated and removed from the animal (male Sprague Dawley rat, Charles River Laboratories, Hollister, Calif.). The endothelium was removed mechanically. Eight strips of tissue (0.5 cm long) were cut. and were mounted in 10 ml organ baths kept at 37° C. with Krebs solution (composition in mM: NaCl (118.2), KCl (4.6), $CaCl_2$ (2.5), $MgSO_4$ (1.2), $KH_2PO_4$ (1.2), $NaHCO_3$ (24.8) and dextrose (10.0)) that was constantly aerated with carbogen gas (95% $O_2$/5% $CO_2$) to obtain a pH of 7.4. The tissues were subjected to a resting tension of 2 g (3 times, 15 minutes apart, equilibrated in Krebs solution). The tissues were then washed 15 minutes later. Ten minutes later, the tissues were then exposed to 0.1 µM phenylephrine. At the maximal effect, 1 µM acetylcholine was added to confirm the absence of endothelium and then washed twice, 2 minutes apart. Fifteen minutes later, vehicle (DMSO), a reference compound (clozapine) or the test compound (Compound K or Compound Q, 10 nM-0.3 µM or 0.1-1 µM) was added to the baths and the tissues were washed every 10 minutes for 60 minutes with vehicle, clozapine, Compound K or Compound Q. A non-cumulative concentration effect curve to 5-HT (serotonin, 0.01 µM-0.1 mM or until maximal response is obtained) was then constructed.

Contractions were recorded as changes in tension from baseline and expressed as a percentage of the maximum response of the agonist (5-HT) concentration-effect curve. Agonist concentration-response curves were fitted using a nonlinear iterative fitting program (GraphPad Prism) using the relationship of Parker and Waud (Parker, R. B. and Waud, D. R. (1971). Pharmacological estimation of drug-receptor dissociation constants. Statistical evaluation. I. Agonists. J. Pharmacol. Exp. Ther., 177, 1-12). Agonist potency was expressed as $EC_{50}$ (molar concentration of agonist producing 50% of the maximum response). Concentration-ratios (CRs) were determined from $EC_{50}$ values in the presence and absence of antagonist and antagonist affinity estimates ($pK_B$ and $pA_2$ values) were determined. All data are expressed as mean ±s.e. mean.

EXAMPLE 15

Compound K is a Potent Antagonist of Apomorphine-Induced Disruption of Swimming

The antagonism of apomorphine-induced disruption of swimming in mice (Warawa, E. J. et al. (2001). Behavioral approach to nondyskinetic dopamine antagonists: identification of seroquel. J. Med. Chem., 44, 372-389) was used to assess test compounds. Apomorphine-treated mice fail to swim and remain in place, pawing the walls of the swimming chamber, or making abortive swims. Certain atypical antipsychotic compounds "normalize" the swimming behavior of such mice.

Figure 2:
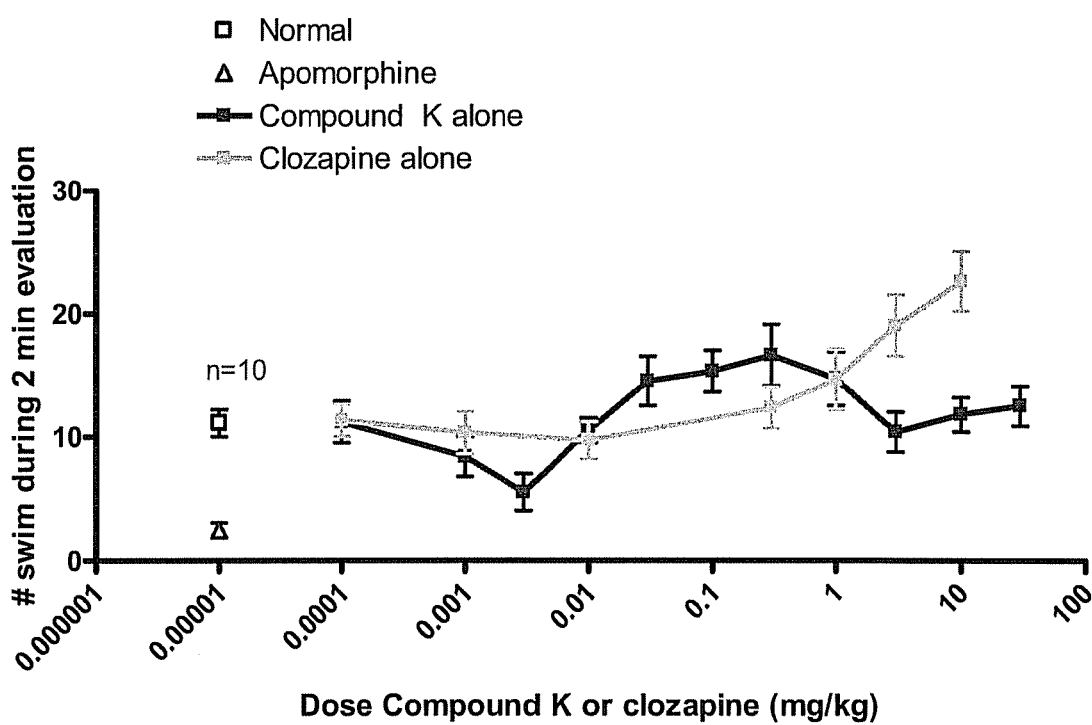
FIG. 2. Antagonism of apomorphine-induced disruption of swimming in mice for Compound K and clozapine (minus aomorphine).
Figure 3:
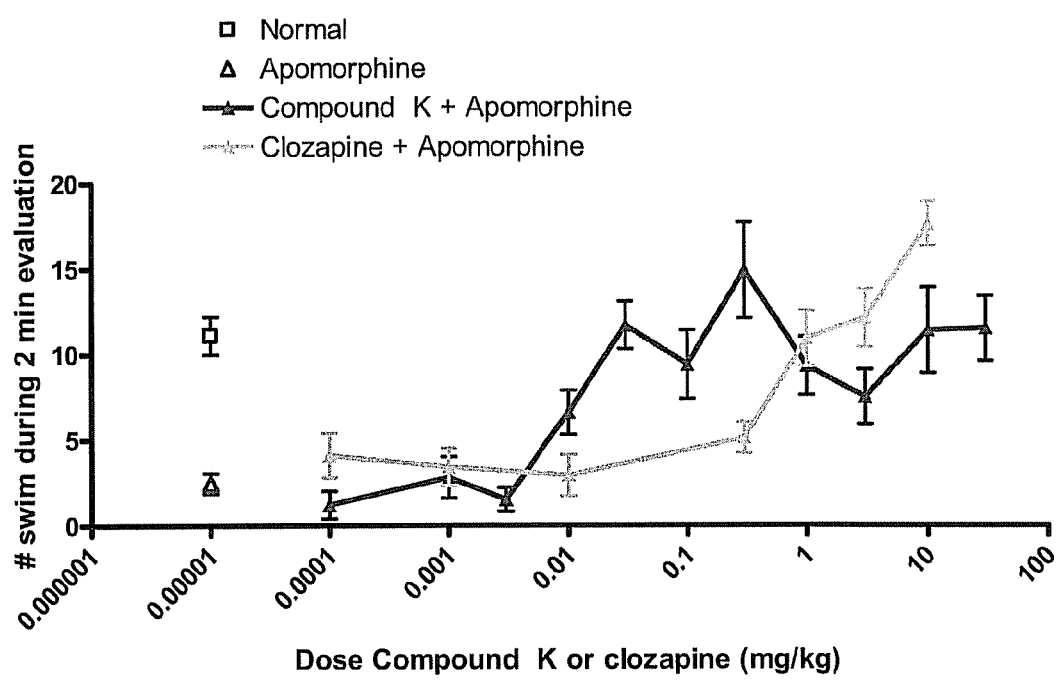
FIG. 3. Antagonism of apomorphine-induced disruption of swimming in mice for Compound K and clozapine (plus apomorphine).
Figure 4:
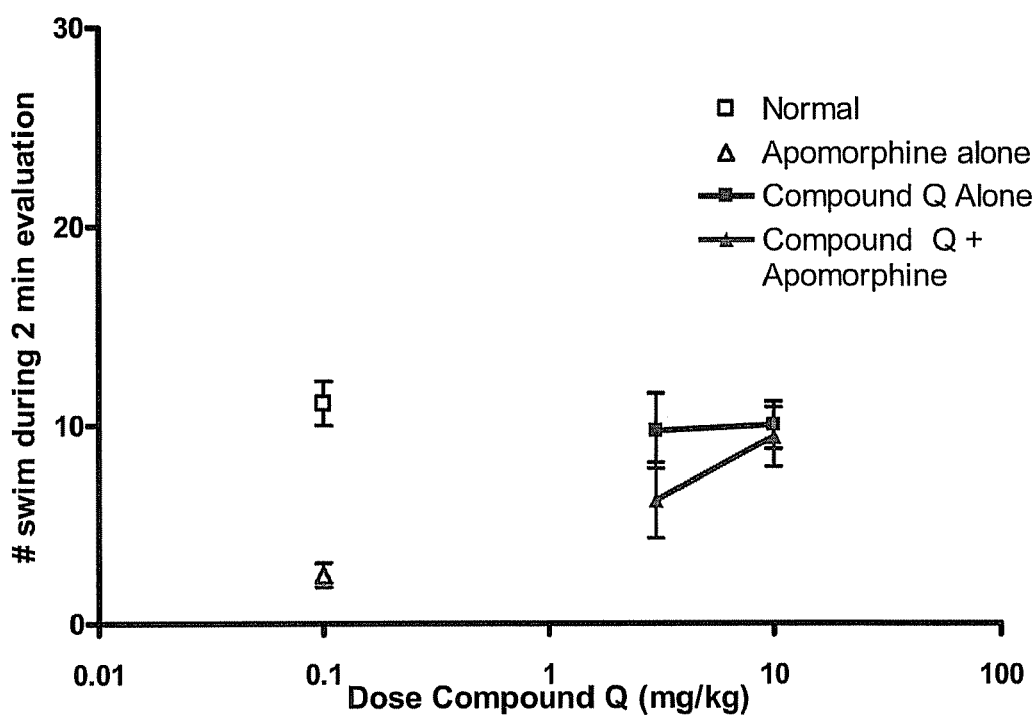
FIG. 4. Antagonism of apomorphine-induced disruption of swimming in mice for Compound Q (plus and minus apomorphine).

Compound K was more potent than clozapine in antagonizing the apomorphine-induced disruption of swimming in mice (see FIGS. 2, 3). Compound Q also reversed the apomorphine-induced disruption of swimming (3 and 10 mg/kg; FIG. 4).

Swim Test Methodology

The animals (Swiss Webster, female, about 20 g; Charles River) were administered compounds of the invention (0.1 µg/kg-30 mg/kg ip) thirty minutes before they were dosed with apomorphine HCl at 1.25 mg/kg sc. Twenty seven minutes after test compound injection, and fifteen minutes after apomorphine injection, each mouse was placed into a circular swimming tank for 2 minutes and the number of "swims" were counted. The height of the tank is 15 cm and the diameter is 28 cm. A circular obstacle, 10.5 cm in diameter and 17 cm high was placed in the center of the tank creating a circular swimming channel 8.75 cm wide. The water level is 5.5 cm and the water was kept at room temperature (about 20° C.). Marks are placed on the floor and side of the tank 180 degrees apart. A "swim" was scored each time a mouse swims from one mark to the other and the median number of swims for all the mice was used as the score for that treatment.

EXAMPLE 16

Compound K and Catalepsy

Figure 5:
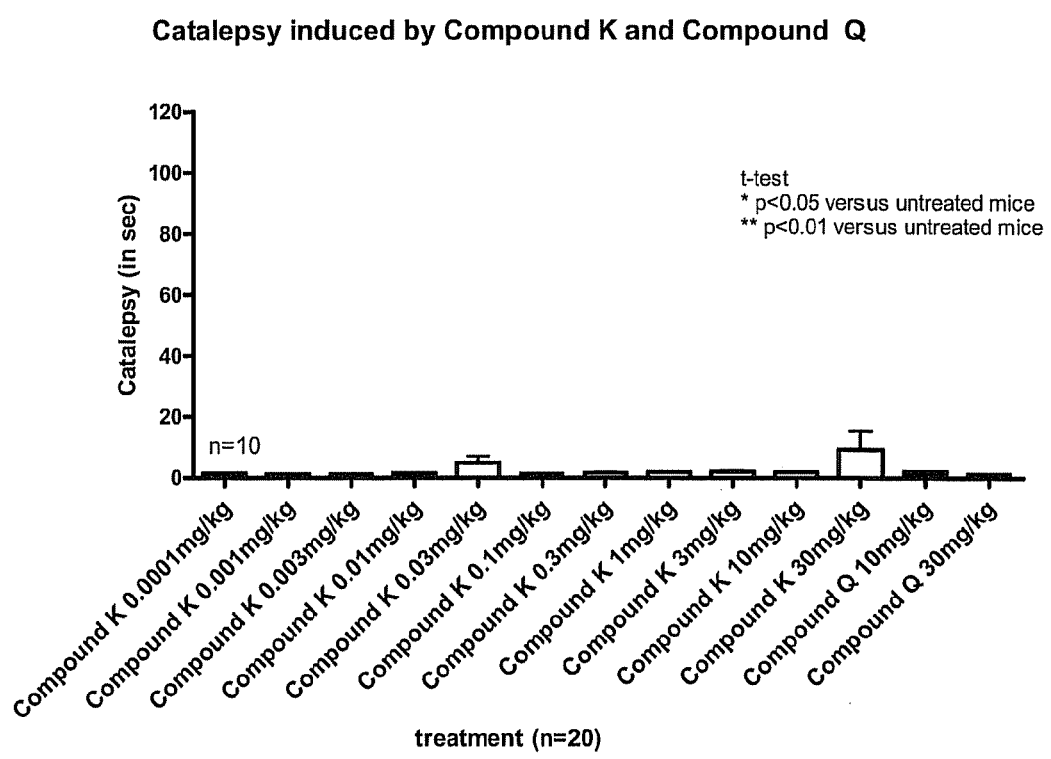
FIG. 5. Catalepsy assessment in mouse catalepsy model for Compound K and Compound Q.
Figure 6:
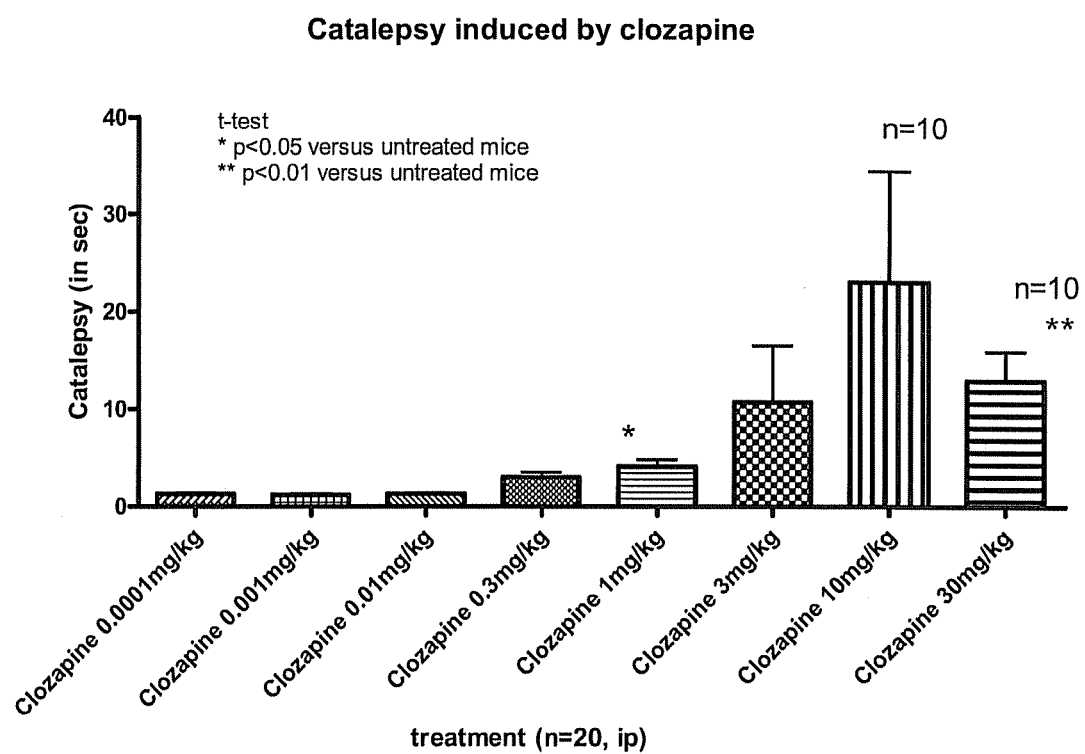
FIG. 6. Catalepsy assessment in mouse catalepsy model for clozapine.

A catalepsy mouse model was used to investigate a potential side effect of antipsychotic agents. Compound K did not cause catalepsy at concentrations up to 30 mg/kg, IP, whereas the highest dose of clozapine (30 mg/kg) induced catalepsy. See FIGS. 5 and 6, respectively.

Catalepsy Methodology

The catalepsy methodology used herein has been adapted from Tada, M. et al. ((2004). Psychopharmacol., 176, 94-100) as well as Wang et al. ((2000). J. Neurosci., 20, 8305-8314).

The animals (Swiss Webster, female, about 20 g; Charles River) were administered compounds of the invention (1 µg/kg-30 mg/kg ip). Twenty seven minutes after test compound injection, the mice's forepaws were placed on a horizontal steel bar (diameter 0.2 cm), elevated 3-5 cm above the tabletop and the time taken for the animals to remove both paws was recorded for up to 2 min.

EXAMPLE 17

Figure 7:
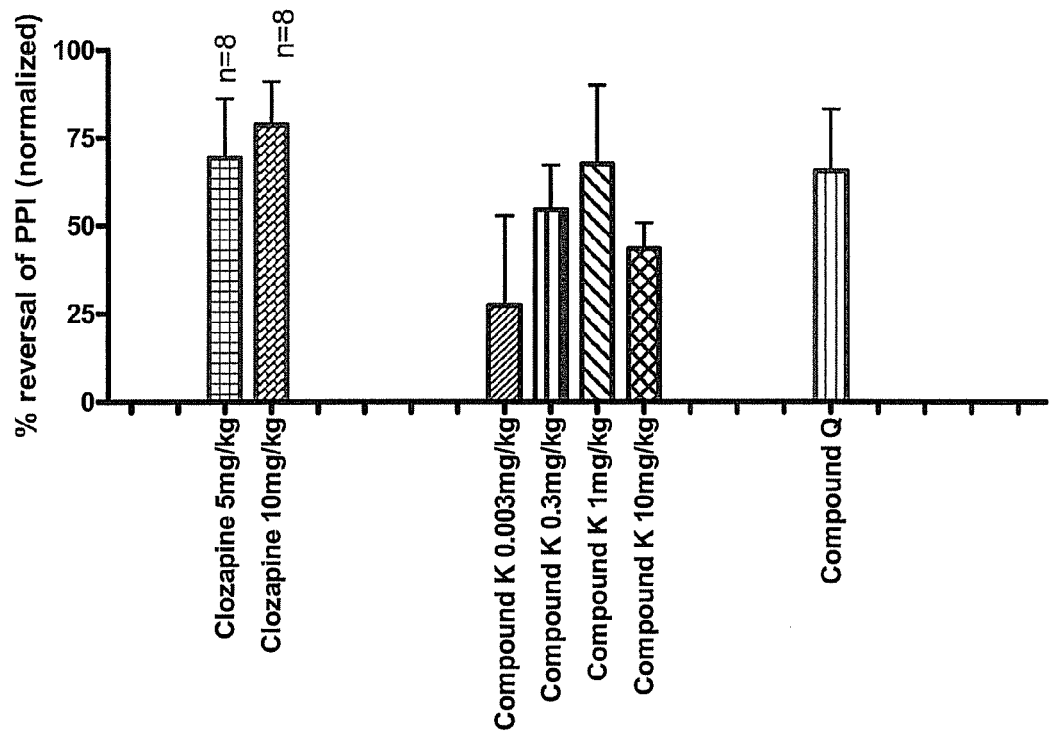
FIG. 7. Compound K and Compound Q restore NMDA antagonist-induced deficits in prepulse inhibition.

Compound K and Compound Q Restore NMDA Antagonist-induced Deficits in Prepulse Inhibition The purpose of the studies was to evaluate the effect of proprietary compounds on the disruption of auditory prepulse inhibition (PPI) in rats. With the PPI procedure, a whole-body startle reflex that is produced by an intense sound is reduced or inhibited by the prior presentation of a weaker sound (prepulse). PPI is a measure of sensorimotor gating, which is disrupted in schizophrenics (Braff, D. L. et al. (1995). Gating and habituation deficits in the schizophrenia disorders. Clin. Neurosci., 3, 131-139). Because reduced glutamate function is postulated to contribute to schizophrenic symptomatology (Carlsson, M. and Carlsson, A. (1990). Interactions between glutamatergic and monoaminergic systems within the basal ganglia: Implications for schizophrenia and Parkinson's disease. Trends Neurosci., 13, 272-276). MK-801-, PCP- and also apomorphine-disrupted PPI are proposed as animal models for specific neurochemical imbalances. Animals were administered antipsychotics such as clozapine or test compounds to antagonize the induced disruption to evaluate their potential beneficial effects in this model. See FIG. 7.

PPI Methodology

The PPI methodology used herein was adapted from Bast, T. et al. ((2000) Effects of MK-801 and neuroleptics on prepulse inhibition: re-examination in two strains of rats. Pharmacol. Biochem. Behav., 67, 647-658) as well as Bubenikova et al. ((2005) The effect of zotepine, risperidone, clozapine and olanzapine on MK-801-disrupted sensorimotor gating. Pharmacol. Biochem. Behav., 80, 591-596).

Rats (Sprague Dawley, 300-450 g; Charles River) were injected with vehicle (DMSO) or compounds Ip. (0.5 ml/kg) 45 min before the PPI experiment. PCP (1.5 mg/kg, 0.5 ml/kg) s.c. was given 15 min before the PPI assay. The animals were then placed in a startle chamber (SR-LAB, San Diego Instruments, USA) which consisted of a clear Plexiglas cylinder (8.2 cm diameter, 10×20 cm) that rested on a piezoelectric accelerometer inside a ventilated and illuminated chamber. The piezoelectric accelerometer detected and transduced motion within the cylinder. A high frequency loudspeaker inside the chamber (24 cm above the animal) produced both a background noise of 77 dB and the acoustic stimuli. The background noise (77 dB) was presented alone for 5 min (acclimatization period) and then continued throughout the session. After the acclimatization period, the test began with 5 initial startle stimuli followed by different trial types presented in a random order: single pulse 120 dB, 20 ms duration; prepulse (83, 86 or 89 dB), 20 ms duration, 100 ms before the onset of the pulse alone; prepulse alone (83, 86 or 89 dB), 20 ms duration; no stimulus. A total of 5 presentations of each trial type were given with an interstimulus interval of about 30 sec. The PPI was measured as a difference between the average values of the single pulse and prepulse-pulse trials and was expressed as a percent of the PPI [100−(mean response for prepulse-pulse trials/startle response for single pulse trials)×100].

EXAMPLE 18

Compound K Did not Reduce Spontaneous Locomotor Activity (Open Field) in Rats

One of the common side effects of many antipsychotic drugs is sedation. It has been shown that agents that have sedative actions in man have the same effect in animals. The purpose of these studies was to evaluate the effect of test compounds on the locomotor activity in rats, which is used to assess the sedative properties of antipsychotic compounds.

Figure 8:
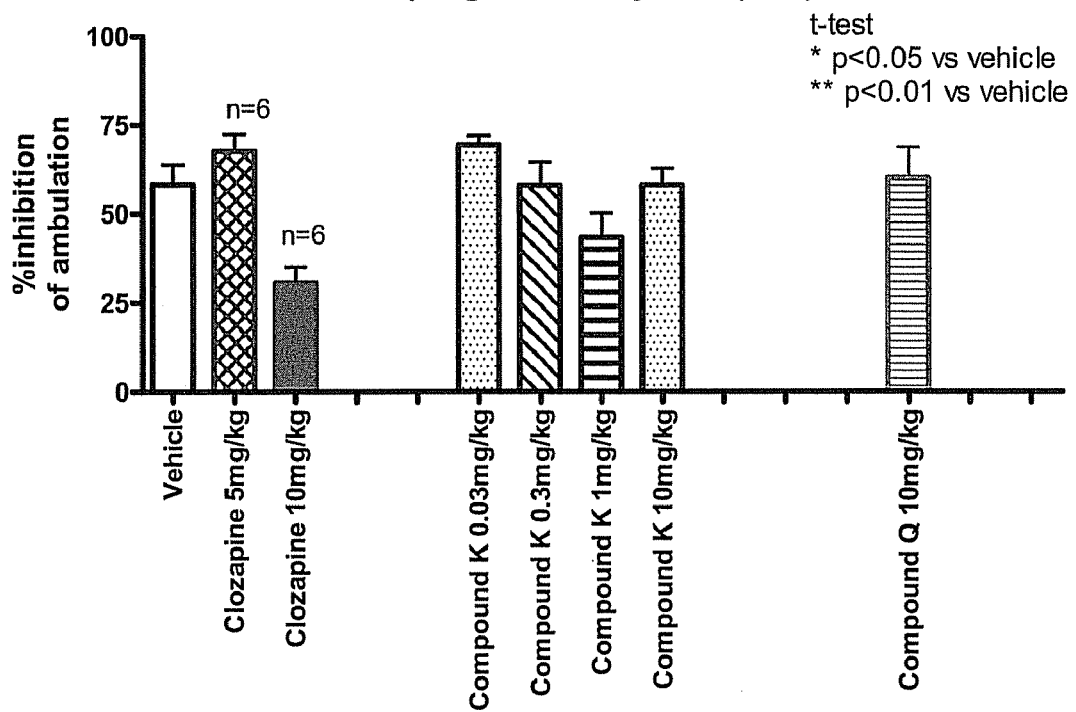
FIG. 8. Compound K does not reduce spontaneous locomotor activity in rats (open field).

Compound K (0.03-10 mg/kg) or Compound Q (10 mg/kg) did not reduce the locomotor activity in rat (see graph below), while clozapine demonstrated a trend toward sedation. See FIG. 8.

Open Field Methodology

The animals (male Sprague Dawley rats, about 300-450 g; Charles River) were assessed for ambulation for 30 minutes before and for 30 min after vehicle or test compounds. The animals were placed in an open field chamber (San Diego Instruments, USA) which consisted of a clear Plexiglas cylinder (16×16) equipped with crisscross photocellbeams. Locomotor activity is quantified by the number of photobeams crossed by the animal over several 3×10 min intervals.

EXAMPLE 19

Metabolism Studies Using Human Liver Microsomal Preparations

Compounds were incubated in pooled human liver microsomes (HLMs) in the presence or absence of an NADPH-generating system. NADPH is required for the activity of cytochrome P450 (CYP) and other oxidative enzymes present in HLMs, but not for esterase activity. An additional incubation was carried out in the absence of HLM to assess compound stability. The disappearance of parent and the appearance of the corresponding acid metabolite were monitored over the time course of the incubations using LC-MS/MS.

A stock solution (20 mM) of each proprietary compound in DMSO was prepared and stored at −20° C. until needed. A working stock solution (0.2 mM) was prepared for each proprietary compound by adding an aliquot of the stock solution (10 μL) to acetonitrile (990 μL).

An aliquot of the HLM solution was removed from the −80° C. freezer and placed on ice. Tris Buffer (50 mM, pH 7.4) containing $MgCl_2$ (hexahydrate, 5 mM) was pre-incubated in a 37° C. water bath. A set of Eppendorf microfuge tubes (1.5 mL) was appropriately labeled. To each tube was added Tris buffer with or without the NADPH generating system. An aliquot of pooled HLMs was added to all the incubations except those that were the buffer control.

Tubes were preincubated for 5 min in a shaking incubator bath (37° C., 900 rpm) and the reaction was initiated by adding an aliquot of the proprietary working solution (5 μL). The additions were timed carefully in order to coordinate the sample collections below. A small aliquot (50 μL) was removed at 0, 5, 15, 30, 60 and 90 min and delivered to the respective tubes containing dextrorphan (100 μL of 0.5 μg/mL solution) dissolved in methanol or acetonitrile. The samples were centrifuged at 14000 g for 15 minutes at 4° C. The supernatant was transferred to clean labeled HPLC injection vials and stored at −80° C. until analyzed. An aliquot of the supernatant (25 μL) was added to water (75 μL), mixed and injected onto the LC-MS/MS system for analysis. Results for some compounds of the invention can be found below in the table in Example 20.

EXAMPLE 20

Metabolism Studies Using Pig Liver Esterase

The esterase-mediated metabolism of these compounds was studied using commercially available pig liver esterase in the presence and absence of human plasma proteins. The disappearance of parent was monitored over the time course of the incubations using a LC-UV detection system.

A stock solution and working stock solution was prepared for each proprietary compound as described for the human liver microsomal incubations. Working solutions of pig liver esterase in potassium phosphate buffer (10 mM, pH 7.4) and pig liver esterase in human plasma protein were prepared by dissolving pig liver esterase (2.51 mg) in the phosphate buffer or plasma protein solutions, respectively.

A set of three Eppendorf microfuge tubes (1.5 mL) was appropriately labeled. To each tube was added 1.5 mL of phosphate buffer, pig liver esterase in buffer, or pig liver esterase in human plasma protein solution. These solutions were pre-incubated (37° C., 900 rpm) and the reactions were initiated by adding an aliquot (37.5 μL) of the working solution of proprietary compound to each tube. An aliquot (100

μL) from each tube was removed at time 0, 5, 30, 60, and 120 min and added to a tube containing acetonitrile (200 μL) to stop the reaction.

The samples were centrifuged at 14000 g for 15 minutes at 4° C. The supernatant was transferred to clean labeled HPLC injection vials and stored at −80° C. until analyzed. An aliquot of the supernatant (25 μL) was injected onto the LC-UV system for analysis. Results for some compounds of the invention are presented in the table below.

| | | HLMs | Pig Liver Esterase ($t_{1/2}$ min.) | | |
|---|---|---|---|---|---|
| Compound | | $t_{1/2}$ (min) | Enzyme | (+) plasma | (−) plasma |
| A | (E)-ethyl 2-(4-(8-chlorodibenzo[b,f][1,4]oxazepin-11-yl)piperazin-2-yl)acetate | 30 | Esterase | 15 | <5 |
| J | (E)-ethyl 2-(4-(7-fluorodibenzo[b,f][1,4]oxazepin-11-yl)piperazin-2-yl)acetate | 10 | Esterase | 15 | <5 |
| L | (E)-isopropyl 2-(4-(8-chlorodibenzo[b,f][1,4]oxazepin-11-yl)piperazin-2-yl)acetate | 30 | P450 | 30 | <5 |
| M | (E)-isopropyl 2-(4-(7-fluorodibenzo[b,f][1,4]oxazepin-11-yl)piperazin-2-yl)acetate | 30 | P450 | 15 | <5 |
| DR | (S,E)-cyclopentyl 2-(4-(8-chlorodibenzo[b,f][1,4]oxazepin-11-yl)piperazin-2-yl)acetate | 30 | Esterase | 15 | <5 |
| DV | (S,E)-tetrahydro-2H-pyran-4-yl 2-(4-(8-chlorodibenzo[b,f][1,4]oxazepin-11-yl)piperazin-2-yl)acetate | 60 | Esterase | 15 | <5 |
| DY | sec-butyl 2-((S)-4-((E)-8-chlorodibenzo[b,f][1,4]oxazepin-11-yl)-1-methylpiperazin-2-yl)acetate | <5 | Esterase | 30 | <5 |
| EQ | (S)-tetrahydrofuran-3-yl 2-((S)-4-((E)-8-chlorodibenzo[b,f][1,4]oxazepin-11-yl)piperazin-2-yl)acetate | 15 | Esterase | 30 | 5 |
| ER | (S,E)-ethyl 2-(4-(8-chlorodibenzo[b,f][1,4]oxazepin-11-yl)-1-isopentylpiperazin-2-yl)acetate | 5 | Esterase | 60 | <5 |
| EU | (S,E)-2-(4-(8-chlorodibenzo[b,f][1,4]oxazepin-11-yl)-1-methylpiperazin-2-yl)-N-(2,2,3,3,3-pentafluoropropyl)acetamide | 60 | P450 | Stable | Stable |

EXAMPLE 21

In the following tables, proprietary compound pKi and pKb values (negative log Ki and negative log Kb, respectively) for various receptors are reported on a scale of 1 through 5, wherein the pKi and pKb scale is defined for each receptor as follows:

| Receptor | 1 | 2 | 3 | 4 | 5 |
|---|---|---|---|---|---|
| $5HT_{2A}$ | ≦7.00 | 7.01-7.50 | 7.51-8.00 | 8.01-8.50 | ≧8.51 |
| $D2_S$ | ≦5.00 | 5.01-5.60 | 5.61-6.20 | 6.21-6.80 | ≧6.81 |
| $D2_L$ | ≦5.00 | 5.01-5.60 | 5.61-6.20 | 6.21-6.80 | ≧6.81 |
| $5HT_{1A}$ | ≦5.00 | 5.01-6.00 | 6.01-7.00 | 7.01-8.00 | ≧8.01 |
| $5HT_{2C}$ | ≦5.00 | 5.01-6.00 | 6.01-7.00 | 7.01-8.00 | ≧8.01 |
| $M_3$ | ≦5.00 | 5.01-5.10 | 5.11-5.20 | 5.21-5.30 | ≧5.31 |
| $H_1$ | ≦5.00 | 5.01-6.00 | 6.01-7.00 | 7.01-8.00 | ≧8.01 |
| $5HT_7$ | ≦5.00 | 5.01-5.40 | 5.41-5.80 | 5.81-6.20 | ≧6.21 |
| $M_1$ | ≦5.00 | 5.01-5.30 | 5.31-5.60 | 5.61-5.90 | ≧5.91 |

| Compound | $5HT_{2A}$ (pKb) | $D2_S$ (pKi) | $D2_L$ (pKi) | $5HT_{1A}$ (pKi) | $5HT_{2C}$ (pKi) | $M_3$ (pKi) | $H_1$ (pKi) | $5HT_7$ (pKi) | $M_1$ (pKi) |
|---|---|---|---|---|---|---|---|---|---|
| A | 3 | 2 | 3 | 3 | 4 | 1 | 3 | | 2 |
| B | 2 | 4 | | | | | | | 1 |
| C | 2 | 2 | | | | | | | 1 |
| D | 2 | 3 | | | | | 3 | | 1 |
| E | 2 | 1 | 1 | 2 | 3 | 1 | 3 | | 1 |
| F | 1 | 3 | | | | | 2 | | 4 |
| G | 3 | 2 | | | | | 2 | | 2 |
| H | 2 | 3 | 3 | | 4 | 1 | 3 | | 1 |
| I | 3 | 2 | 2 | 3 | 4 | 1 | 3 | | 2 |
| J | 2 | 2 | 2 | 3 | 3 | 1 | 3 | | 1 |
| K | 4 | 3 | 3 | 3 | 4 | 1 | 3 | 4 | 1 |
| L | 3 | 2 | 3 | 3 | 4 | 1 | 3 | | 1 |
| M | 3 | 1 | 2 | 3 | 3 | 1 | 2 | | 1 |
| N | 4 | 3 | 3 | 3 | 4 | 1 | 3 | 4 | 2 |
| O | 2 | 2 | 2 | 3 | 4 | 1 | 3 | | |
| P | 2 | 2 | 2 | 2 | 3 | 1 | 3 | | |
| Q | 3 | 1 | 1 | 3 | 3 | 1 | 3 | | 1 |
| AB | 2 | 1 | 1 | 1 | 3 | 1 | 3 | | |
| DM | 3 | 1 | | | | | | | |
| DN | 2 | 2 | 2 | | 3 | 1 | 3 | | 3 |
| DO | | 1 | | 2 | 3 | | 4 | | |
| DQ | 1 | 2 | 2 | 3 | 3 | 1 | 2 | 2 | 1 |

-continued

| Compound | 5HT$_{2A}$ (pKb) | D2$_S$ (pKi) | D2$_L$ (pKi) | 5HT$_{1A}$ (pKi) | 5HT$_{2C}$ (pKi) | M$_3$ (pKi) | H$_1$ (pKi) | 5HT$_7$ (pKi) | M$_1$ (pKi) |
|---|---|---|---|---|---|---|---|---|---|
| DR | 3 | 3 | 3 | 4 | 4 | 1 | 2 | 3 | 4 |
| DS | 1 | 1 |   | 2 | 2 | 1 |   | 1 |   |
| DT | 1 | 1 | 1 | 3 | 3 | 1 | 2 | 1 | 2 |
| DU | 1 | 2 | 2 | 4 | 3 | 1 | 3 | 2 | 2 |
| DV | 4 | 3 | 2 | 4 | 4 | 1 | 2 | 3 | 1 |
| DW | 2 | 1 | 2 | 2 | 3 | 1 | 3 | 2 | 5 |
| DX | 3 | 2 | 2 | 2 | 3 | 1 | 3 | 1 | 2 |
| DY | 3 | 2 |   | 2 | 3 | 1 | 4 | 1 | 1 |
| DZ | 2 | 2 |   | 3 | 3 | 1 |   | 1 |   |
| EA | 3 | 2 |   | 4 | 4 | 1 | 3 | 1 | 4 |
| EB | 3 | 3 |   | 5 | 4 | 1 | 4 | 3 | 2 |
| EC | 3 | 3 |   | 4 | 4 | 1 | 4 | 4 | 1 |
| ED | 4 | 3 | 3 | 4 | 5 | 1 | 4 | 4 | 2 |
| EO | 3 | 3 |   | 5 | 4 | 1 | 4 | 4 | 1 |
| EP | 3 | 4 |   | 4 |   |   | 3 |   | 2 |
| EQ | 4 | 3 |   | 4 |   |   | 4 |   | 2 |
| ER | 2 | 2 |   | 2 |   |   | 3 |   | 1 |
| ES |   | 1 |   | 2 |   |   | 4 |   | 1 |
| ET | 1 | 3 |   | 2 |   |   | 3 |   | 3 |
| EU | 1 | 2 |   | 2 |   |   | 3 |   | 1 |
| EV | 2 | 2 |   | 2 |   |   | 4 |   | 2 |
| EW | 1 | 1 |   | 2 | 2 |   | 3 |   | 2 |
| EX |   | 2 |   | 2 | 3 |   | 4 |   | 2 |
| EY | 4 | 3 | 3 | 4 | 4 | 1 | 4 | 4 | 1 |
| EZ | 2 | 2 | 2 | 5 | 4 | 1 | 4 | 4 | 1 |
| FA 9313 | 4 | 3 | 3 | 4 | 4 | 1 | 4 | 4 | 1 |
| FB | 5 | 3 | 3 | 4 | 4 | 1 | 4 | 4 | 1 |
| FC | 4 | 3 | 3 | 4 | 4 | 1 | 4 | 4 | 1 |
| FN | 4 | 3 | 3 | 4 | 4 | 1 | 4 | 4 | 1 |
| FO | 3 | 2 | 2 | 3 | 4 | 1 | 4 | 4 | 3 |
| FP | 3 | 3 | 3 | 5 | 4 | 1 | 4 | 3 | 2 |
| FQ | 3 | 3 | 3 | 4 | 4 | 1 | 4 | 4 | 2 |
| FR | 4 | 4 | 4 | 4 | 4 | 1 | 4 | 4 | 1 |
| FS | 4 | 3 | 3 | 4 | 4 | 1 | 5 | 5 | 1 |
| GD | 3 | 3 | 3 | 4 | 4 | 1 | 4 | 4 | 1 |
| GE | 3 | 2 |   | 3 |   |   |   |   | 3 |
| GF | 3 | 3 | 2 | 3 | 4 | 1 | 4 | 4 | 1 |
| GG | 4 | 2 | 2 | 4 | 4 | 2 | 5 | 4 | 4 |
| GH | 2 | 2 | 3 | 3 | 3 | 2 | 4 | 3 | 5 |
| GI | 2 | 1 |   | 2 |   |   |   |   | 1 |

EXAMPLE 22

Overview of hD$_{2S}$ Receptor and h5-HT$_7$ Receptor Assay Conditions

|  | hD$_{2S}$ Receptor | h5-HT$_7$ Receptor |
|---|---|---|
| Source | membranes from Chinese hamster ovary cells transfected with human D$_{2S}$ dopamine receptors | membranes from Chinese hamster ovary cells transfected with human 5HT$^7$ receptors |
| Ligand | 0.1 nM/0.2 nM [$^3$H]spiperone | 0.3 nM [$^3$H]5-CT |
| K$_D$ | 0.1 nM | 0.2 nM |
| B$_{MAX}$ | 2.5 pmole/mg protein | 1.6 pmole/mg protein |
| Nonspecific ligand | 5 μM (+)-butaclamol | 25 mM Clozapine |
| Specific Binding | 78% | 66% |
| Vehicle | 0.1% DMSO | 0.1% DMSO |
| Incubation time | 180 min | 120 min |
| Incubation temperature | 26° C. | 27° C. |
| Incubation buffer | 20 mM Hepes, pH 7.4, 1 mM EGTA, 6 mM MgCl$_2$*6H$_2$O, 1 mM EDTA | 50 mM Tris-HCl, pH 7.4, 10 mM MgSO4*7H20, 0.5 mM EDTA |

EXAMPLE 23

Overview of hD$_{2L}$ Receptor and hH$_1$ Receptor Assay Conditions

|  | hD$_{2L}$ Receptor | hH$_1$ Receptor |
|---|---|---|
| Source | membranes from insect sf9 cells expressing human D$_{2L}$ dopamine receptors | membranes from Chinese hamster ovary cells transfected with human H$_1$ receptors |
| Ligand | 0.4 nM [$^3$H]spiperone | 2.0 nM [$^3$H]Pyrilamine |
| K$_D$ | 0.4 nM | 1.1 nM |
| B$_{MAX}$ | 1.36 pmole/mg protein | 1.55 pmole/mg protein |
| Nonspecific ligand | 1 μM (+)-butaclamol | 1 μM pyrilamine |
| Specific Binding | 81% | 88% |
| Vehicle | 0.1% DMSO | 0.1% DMSO |
| Incubation time | 60 min | 60 min |
| Incubation temperature | 27° C. | 27° C. |
| Incubation buffer | 50 mM Tris-HCl, pH 7.4, 120 mM NaCl, 1 mM EDTA, 10 mM MgCl$_2$*6H$_2$O | 50 mM Tris-HCl, 10 μg/mL Saponin, pH 7.4 |

EXAMPLE 24

Overview of hM$_1$ Receptor and hM$_2$ Receptor Assay Conditions

|  | hM$_1$ Receptor | hM$_3$ Receptor |
|---|---|---|
| Source | membranes from Chinese hamster ovary cells transfected with human M$_1$ receptors | membranes from Chinese hamster ovary cells transfected with human M$_3$ receptors |
| Ligand | 1 nM [$^3$H]NMS | 0.1 nM [$^3$H]NMS |
| K$_D$ | 0.49 nM | 0.1 nM |
| B$_{MAX}$ | 1.42 pmole/mg protein | 3.57 pmole/mg protein |
| Nonspecific ligand | 2 μM NMS | 5 μM atropine |
| Specific Binding | 90% | 96% |
| Vehicle | 0.1% DMSO | 0.1% DMSO |
| Incubation time | 60 mon | 135/75 min |
| Incubation temperature | 25° C. | 26° C. |
| Incubation buffer | 50 mM Tris-HCl, 10 μg/mL Saponin, pH 7.4 | DPBS w/o calcium or magnesium, pH 7.4 |

EXAMPLE 25

Overview of h5-HT$_{1A}$ Receptor and h5-HT$_{2C}$ Receptor Assay Conditions

|  | h5-HT$_{1A}$ Receptor | h5-HT$_{2C}$ Receptor |
|---|---|---|
| Source | membranes from Chinese hamster ovary cells transfected with human 5HT$_{1A}$ receptors | membranes from human embryo kidney cells expressing human 5HT$_{2C}$ receptors |
| Ligand | 2.5 nM [$^3$H]8OH-DPAT | 1.2 nM [$^3$H]Mesulergine |
| K$_D$ | 9 nM | 1.2 nM |
| B$_{MAX}$ | 4.98 pmole/mg protein | 1.7 pmole/mg protein |
| Nonspecific ligand | 4 μM 5-HT creatinine sulfate | 1 μM mianserine |
| Specific Binding | 84% | 68% |
| Vehicle | 0.1% DMSO | 0.1% DMSO |
| Incubation time | 120 min | 60 min |
| Incubation temperature | 37° C. | 27° C. |
| Incubation buffer | 50 mM Tris-HCl, pH 7.4, 5 mM MgSO$_4$*7H$_2$O | 50 mM Tris-HCl, pH 7.4, 0.1% BSA, 1 mM EDTA, 10 mM MgCl$_2$*6H$_2$O |

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

We claim:
1. A compound having the structure

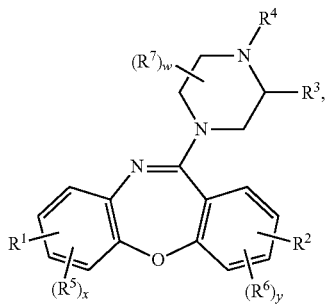

or a pharmaceutically acceptable salt thereof,
wherein
R$^1$ and R$^2$ are independently —Cl, —F, —Br, —I or —H;
R$^3$ is —(C$_0$-C$_6$ alk)C(O)OR$^e$, —(C$_0$-C$_6$ alk)C(O)NR$^a{}_2$, —(C$_0$-C$_6$ alk)C(O)NR$^a$R$^{19}$, —(C$_0$-C$_6$ alk)C(O)NR$^{19}{}_2$, —(C$_0$-C$_6$ alk)-C(O)NR$^{20}$, —(C$_0$-C$_6$ alk)Ar, —(C$_0$-C$_6$ alk)-O—(C$_0$-C$_6$ alk)Ar, —(C$_0$-C$_6$ alk)-OR, —(C$_0$-C$_6$ alk)C(O)R$^k$, or —(C$_0$-C$_6$ alk)-NR$^a$R$^{19}$;
R$^4$ is —H or —R;
each R$^5$, R$^6$ and R$^7$ is independently —R, —(C$_0$-C$_6$ alk)-OR, —(C$_0$-C$_6$ alk)-NR$^a$R$^{19}$, —NO$_2$, -halogen, —CN, —OH, —(C$_0$-C$_6$ alk)COOR$^e$, —(C$_0$-C$_6$ alk)C(O)NR$^a$R$^{19}$, —(C$_0$-C$_6$ alk)Ar, —(C$_0$-C$_6$ alk)-O—(C$_0$-C$_6$ alk)Ar, —(C$_0$-C$_6$ alk)Het, —(C$_0$-C$_6$ alk)-O—(C$_0$-C$_6$ alk)Het, —(C$_0$-C$_6$ alk)Hca, —(C$_0$-C$_6$ alk)-O—(C$_0$-C$_6$ alk)Hca, —(C$_0$-C$_6$ alk)Cak, —(C$_0$-C$_6$ alk)-O—(C$_0$-C$_6$ alk)Cak, —(C$_0$-C$_6$ alk)C(O)Hca, —(C$_0$-C$_6$ alk)C(O)Ar, —(C$_0$-C$_6$ alk)C(O)Het, or —(C$_0$-C$_6$ alk)C(O)Cak;
w is 0, 1, 2 or 3;
x is 0, 1, 2 or 3; and
y is 0, 1, 2 or 3;
in which
each R$^e$ is independently —H, —R, —(C$_1$-C$_6$ alk)C(O)Hca, —(C$_1$-C$_6$ alk)C(O)Cak, —(C$_1$-C$_6$ alk)C(O)Het, —(C$_1$-C$_6$ alk)C(O)Ar, —(C$_1$-C$_6$ alk)C(O)O—Hca, —(C$_1$-C$_6$ alk)C(O)O-Cak, —(C$_1$-C$_6$ alk)C(O)O—Het, —(C$_1$-C$_6$ alk)C(O)O—Ar, —(C$_0$-C$_6$ alk) Hca, —(C$_0$-C$_6$ alk) Het, —(C$_0$-C$_6$ alk)Ar, —(C$_0$-C$_6$ alk) Cak, —(C$_1$-C$_6$ alk)C(O)OR, —(C$_1$-C$_6$ alk)C(O)NR$^{19}{}_2$, —(C$_0$-C$_6$ alk)-OR, or —(C$_0$-C$_6$ alk)-OH;
each R$^a$ is independently —H, —R, —(C$_1$-C$_6$ alk)-OR, —(C$_1$-C$_6$ alk)-OH, —(C$_0$-C$_6$ alk)C(O)OR, —(C$_1$-C$_6$ alk)-NR$^{19}{}_2$, —(C$_0$-C$_6$ alk)Hca, —(C$_0$-C$_6$ alk)Ar, —(C$_0$-C$_6$ alk)Het, or —(C$_0$-C$_6$ alk)Cak;
each R$^k$ is independently —H, —R, —(C$_1$-C$_6$ alk)C(O)Hca, —(C$_1$-C$_6$ alk)C(O)Cak, —(C$_1$-C$_6$ alk)C(O)Het, —(C$_1$-C$_6$ alk)C(O)Ar, —(C$_1$-C$_6$alk)Hca, —(C$_0$-C$_6$ alk)Het, —(C$_0$-C$_6$ alk)Ar, —(C$_0$-C$_6$ alk)Cak, —(C$_1$-C$_6$ alk)C(O)OR, or —(C$_1$-C$_6$ alk)C(O)NR$^{19}{}_2$;
each Cak is a cycloalkyl or cycloalkenyl group, optionally substituted with 1, 2 or 3 substituents independently selected from —R, —(C$_0$-C$_6$ alk)C(O)OR, =O, —OH, —CN, —(C$_0$-C$_6$ alk)OR, —OCH$_2$CH$_2$—O—, —OCH$_2$—O—, —SO$_2$—R, —SO$_2$—(C$_1$-C$_6$ haloalkyl), —(C$_0$-C$_6$ alk)C(O)NR$^{19}{}_2$, —(C$_0$-C$_6$ alk)Het, —SO$_2$(C$_0$-C$_6$ alk)-Hca, —(C$_0$-C$_6$ alk)Ar, —(C$_0$-C$_6$ alk)Het, —(C$_0$-C$_6$ alk)Hca, —(C$_0$-C$_6$ alk)C(O)R, —SO$_2$(C$_0$-C$_6$ alk)Ar, —SO$_2$(C$_0$-C$_6$ alk)Het, and —SO$_2$(C$_0$-C$_6$ alk)cycloalk, each Ar is an aryl group, optionally substituted with 1, 2 or 3 substituents independently selected from —R, —OR, —($C_0$-$C_6$ alk)$NR^{19}_2$, —$NO_2$, —Cl, —F, —Br, —I, —CN, —($C_0$-$C_6$ alk)OH, —($C_0$-$C_6$ alk)C(O)OR, —($C_0$-$C_6$ alk)C(O)OH, —($C_1$-$C_6$ haloalkyl), —O($C_1$-$C_6$ haloalkyl), —($C_0$-$C_6$ alkyl)heterocycloalk, —$SO_2R$, —($C_0$-$C_6$ alk)-C)(O)-heterocycloalk, —($C_0$-$C_6$ alk)-C(O)-cycloalk, —($C_0$-$C_6$ alkyl)-C(O)-heteroaryl, —($C_0$-$C_6$ alk)-C(O)-aryl, —($C_0$-$C_6$ alkyl)-C(O)O-heterocycloalk, —($C_0$-$C_6$ alk)-C(O)O-cycloalk, —($C_0$-$C_6$ alkyl)-C(O)O-heteroaryl, —($C_0$-$C_6$ alk)-C(O)O-aryl, —($C_0$-$C_6$ alk)-heterocycloalkyl, —($C_0$-$C_6$ alk)-heteroaryl, —($C_0$-$C_6$ alk)-aryl, and -($C_0$-$C_6$ alk)-cycloalk;

each Het is a heteroaryl group, optionally substituted with 1, 2 or 3 groups independently selected from —R, —OR, —($C_0$-$C_6$ alk)$NR^{19}_2$, —$NO_2$, —Cl, —F, —Br, —I, —CN, —($C_0$-$C_6$ alk)OH, —($C_0$-$C_6$ alk)$CO_2R$, —($C_0$-$C_6$ alk)C(O)OH, —($C_1$-$C_6$ haloalkyl), -O($C_1$-$C_6$ haloalkyl), -($C_0$-$C_6$ alkyl)heterocycloalk, —$SO_2R$, —($C_0$-$C_6$ alk)-C(O)-heterocycloalk, —($C_0$-$C_6$ alk)-C(O)-cycloalk, —($C_0$-$C_6$ alk)-C(O)-heteroaryl, —($C_0$-$C_6$ alk)-C(O)-aryl, —($C_0$-$C_6$ alk)-C(O)O- heterocycloalk, —($C_0$-$C_6$ alk)-C(O)O-cycloalk, —($C_0$-$C_6$ alk)-C(O)O-heteroaryl, —($C_0$-$C_6$ alk)-C(O)O-aryl, —($C_0$-$C_6$ alk)-heterocycloalkyl, —($C_0$-$C_6$alk)-heteroaryl, —($C_0$-$C_6$ alk)-aryl, and -($C_0$-$C_6$ alk)-cycloalk;

each Hca is a heterocycloalk group, optionally substituted with 1, 2 or 3 substituents independently selected from —R, —($C_1$-$C_6$ haloalkyl), —O($C_1$-$C_6$ haloalkyl), —($C_0$-$C_6$ alk)-C(O)OR, —($C_0$-$C_6$ alk)-C(O)R, =O, —OH, —CN, —($C_0$-$C_6$ alk)OR, —$OCH_2CH_2$—O—, —$OCH_2$O—, —$SO_2R$, —$SO_2$—($C_1$-$C_6$ haloalkyl), —($C_0$-$C_6$ alk)C(O)$NR^{19}_2$, —($C_0$-$C_6$ alk)-heterocycloalk, —($C_0$-$C_6$ alk)-aryl, —($C_0$-$C_6$ alk)-heterocycloalk, —($C_0$-$C_6$ alk)-cycloalk, —$SO_2$($C_0$-$C_6$ alk)-heterocycloalk, —$SO_2$($C_0$-$C_6$ alk)-aryl, —$SO_2$($C_0$-$C_6$ alk)-heteroaryl —$SO_2$($C_0$-$C_6$ alkyl)heteroaryl, and —$SO_2$($C_0$-$C_6$ alk)-cycloalk;

each $R^{19}$ is independently selected from —H, —OH and —R, in which any ($C_1$-$C_8$ alk) or —($C_1$-$C_8$ haloalkyl) groups are optionally substituted with 1, 2 or 3 substituents independently selected from =O, —($C_1$-$C_6$ alkoxy), —OH, and -halogen;

each $R^{20}$ is a Hca or Het ring wherein that N from the —($C_0$-$C_6$ alk)-C(O)$NR^{20}$ is a heteroatom in the Hca or Het ring, the ring optionally substituted with 1 or 2 substituents independently selected from =O, —($C_1$-$C_6$ alkoxy), —OH, -halogen, —($C_1$-$C_6$ haloalkyl), —$SO_2$—($C_1$-$C_6$ alk), and -C(O)—($C_1$-$C_6$ alk), each R is independently -($C_1$-$C_8$ alk), —($C_3$-$C_8$ cycloalk), —($C_3$-$C_{12}$ heterocycloalk), —($C_1$-$C_8$ haloalkyl), or —($C_3$-$C_8$ halocycloalk), optionally substituted with 1, 2 or 3 substituents independently selected from —($C_1$-$C_6$ alkoxy), —($C_1$-$C_6$ hydroxyalkyoxy), —($C_1$-$C_6$ hydroxyalkyl), acetoxyalkyl, —C(O)O($C_1$-$C_6$ alkyl), —OH, =O, —N($C_1$-$C_6$ alkyl)$_2$, -NH($C_1$-$C_6$ alk), —$NH_2$, —OC(O)($C_0$-$C_6$ alk), —$SO_2$—($C_1$-$C_6$ alk), and —CO—($C_0$-$C_6$ alk); and each ($C_0$-$C_6$ alk), ($C_1$-$C_6$ alk), and —($C_1$-$C_8$ alk) is independently optionally substituted with 1, 2, 3 or 4 substituents selected independently from -($C_1$-$C_4$ alkyl), —($C_1$-$C_4$ alkoxy), —OH, =O, -halogen, —C(O)O($C_1$-$C_3$ alkyl) and —C(O)($C_1$-$C_3$ alkyl).

2. A compound according to claim 1, wherein $R^3$ is —($C_0$-$C_6$ alk)C(O)$OR^e$, —($C_0$-$C_6$ alk)C(O)$NR^a_2$, —($C_0$-$C_6$ -alk)C(O)$NR^aR^{19}$, —($C_0$-$C_6$ alk)C(O)$NR^{19}_2$, or —($C_0$-$C_6$ alk)-C(O)$NR^{20}$.

3. A compound according to claim 2, wherein $R^3$ is —($C_0$-$C_6$ alk)C(O)$OR^e$.

4. A compound or salt according to claim 3, wherein each alk group is an alkyl group.

5. A compound or salt according to claim 3, wherein at least one of $R^1$ and $R^2$ is —F, —Cl, —Br or —I.

6. A compound or salt according to claim 3, wherein both x and y are 0.

7. A compound or salt according to claim 3, wherein all of w, x and y are 0.

8. A compound or salt according to claim 3 having S configuration at the carbon of attachment of the $R^3$ group.

9. A compound or salt according to claim 3 having R configuration at the carbon of attachment of the $R^3$ group.

10. The compound or salt according to claim 3 having a mixture of configurations at the carbon of attachment of the $R^3$ group.

11. A compound or salt according to claim 3, wherein all of w, x and y are 0 and $R^4$ is —H.

12. A compound or salt according to claim 1, wherein
$R^1$ and $R^2$ are independently —Cl, —F, —Br, —I or —H, with the proviso that at least one of $R^1$ and $R^2$ is —Cl, —F, —Br or —I;
$R^3$ is —($C_0$-$C_6$ alk)C(O)$OR^e$, —($C_0$-$C_6$ alk)C(O)$NR^a_2$, or —($C_0$-$C_6$ -alk)C(O)$NR^aR^{19}$;
$R^4$ is —H or —R;
each $R^5$, $R^6$, and $R^7$ is independently —R, —OR, —$NR^aR^{19}$, —$NO_2$, —F, —Br, —I, —CN, —OH, —($C_0$-$C_6$ alkyl)C(O)$OR^e$, —($C_0$-$C_6$ alkyl)C(O)$NR^aR^{19}$, or —($C_0$-$C_6$ alkyl)C(O)$NR^aR^{19}$; and
w, x and y are independently 0, 1 or 2;
in which
each $R^e$ is independently —H or —R,
each $R^a$ is independently —H or —R,
each $R^{19}$ is independently —H or —R,
each Ar is independently phenyl optionally substituted with 1, 2 or 3 substituents selected from —R, —OR, —$NR_2$, —$NO_2$, —Cl, —F, —Br, —I, —CN, —OH, —C(O)OR, —($C_1$-$C_6$ haloalkyl) and —O($C_1$-$C_6$ haloalkyl),
each R is independently —($C_1$-$C_8$ alkyl), —($C_3$-$C_8$ cycloalkyl), —($C_3$-$C_{12}$ heterocycloalk), —($C_1$-$C_8$ fluoroalkyl), —($C_3$-$C_8$ fluorocycloalk), —($C_1$-$C_8$ chloroalkyl), or —($C_3$-$C_8$ chlorocycloalk), wherein the —($C_1$-$C_6$ fluoroalkyl), —($C_3$-$C_8$ fluorocycloalk), —($C_1$-$C_6$ chloroalkyl), or —($C_3$-$C_8$ chlorocycloalk) may be substituted with from 1 to 6 fluorines or chlorines, respectively, each R optionally substituted with 1, 2 or 3 substituents selected from —($C_1$-$C_6$ alkoxy), —($C_1$-$C_6$ hydroxyalkyl), acetoxyalkyl, and —C(O)O ($C_1$-$C_4$ alkyl).

13. A compound or salt according to claim 12, wherein each alk group is an alkyl group.

14. A compound or salt according to claim 12, wherein $R^3$ is —($C_0$-$C_6$ alkyl)C(O)$OR^e$.

15. A compound or salt according to claim 14, wherein $R^e$ is —H, -Me, -Et, -Pr or -Bu.

16. A compound or salt according to claim 12 having S configuration at the carbon of attachment of the $R^3$ group.

17. A compound or salt according to claim 12 having R configuration at the carbon of attachment of the $R^3$ group.

18. A compound or salt according to claim 12 having a mixture of configurations at the carbon of attachment of the $R^3$ group.

19. A compound or salt according to claim 12, wherein $R^4$ is —H.

20. A compound or salt according to claim 12, wherein w, x and y are each 0.

21. A compound or salt according to claim 1, having the structure:

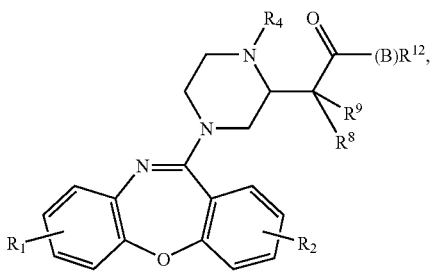

wherein,
$R^1$ and $R^2$ are independently —Cl, —F, —Br, —I or —H, with the proviso that at least one of $R^1$ and $R^2$ is —Cl, —F, —Br or —I;
$R^4$ is —H or —R;
$R^8$ is —H, -Me, -Et or -Pr;
$R^9$ is —H, -Me, -Et or -Pr;
B is O or NH, and
$R^{12}$ is —H, -Me, -Et or -Pr.

22. A compound or salt according to claim 21, wherein B is O.

23. A compound or salt according to claim 1, wherein the compound is
(E)-ethyl2-(4-(8-chlorodibenzo[b,f][1,4]oxazepin-11-yl)piperazin-2-yl)acetate;
(E)-2-(4-(8-chlorodibenzo[b,f][1,4]oxazepin-11-yl)piperazin-2-yl)-N-isobutylacetamide;
(E)-ethyl2-(4-(2-chlorodibenzo[b,f][1,4]oxazepin-11-yl)piperazin-2-yl)acetate *(S) or (R) at stereocenter;
(R,E)-methyl4-((4-(2-chlorodibenzo[b,f][1,4]oxazepin-11-yl)piperazin-2-yl)methoxy)benzoate;
(E)-2-(4-(8-chlorodibenzo[b,j][1,4]oxazepin-11-yl)piperazin-2-yl)acetic acid;
(E)-ethyl4-(2-(4-(8-chlorodibenzo[b,f][1,4]oxazepin-11-yl)piperazin-2-yl)ethyl)benzoate;
(E)-methyl4-((4-(8-chlorodibenzo[b,f][1,4]oxazepin-11-yl)piperazin-2-yl)methoxy)benzoate;
(E)-ethyl2-(4-(7-chlorodibenzo[b,f][1,4]oxazepin-11-yl)piperazin-2-yl)acetate;
(E)-methyl2-(4-(8-chlorodibenzo[b,f][1,4]oxazepin-11-yl)piperazin-2-yl)acetate;
(E)-ethyl2-(4-(7-fluorodibenzo[b,f][1,4]oxazepin-11-yl)piperazin-2-yl)acetate;
(S,E)-ethyl2-(4-(8-chlorodibenzo[b,f][1,4]oxazepin-11-yl)piperazin-2-yl)acetate;
(E)-isopropyl2-(4-(8-chlorodibenzo[b,f][1,4]oxazepin-11-yl)piperazin-2-yl)acetate;
(E)-isopropyl2-(4-(7-fluorodibenzo[b,f][1,4]oxazepin-11-yl)piperazin-2-yl)acetate;
(S,E)-methyl2-(4-(8-chlorodibenzo[b,f][1,4]oxazepin-11-yl)piperazin-2-yl)acetate;
(R,E)-ethyl2-(4-(8-chlorodibenzo[b,f][1,4]oxazepin-11-yl)piperazin-2-yl)acetate;
(R,E)-methyl2-(4-(8-chlorodibenzo[b,f][1,4]oxazepin-11-yl)piperazin-2-yl)acetate;
(S,E)-2-(4-(8-chlorodibenzo[b,f][1,4]oxazepin-2-yl)acetic acid;
(R)-2-((S)-4-((E)-8-chlorodibenzo[b,f][1,4]oxazepin-11-yl)piperazin-2-yl)propanoic acid;
(S)-2-((S)-4-((E)-8-chlorodibenzo[b,f][1,4]oxazepin-11-yl)piperazin-2-yl)propanoic acid;
(R)-2-((S)-4-((E)-8-chlorodibenzo[b,f][1,4]oxazepin-11-yl)piperazin-2-yl)butanoic acid;
(S)-2-((S)-4-((E)-8-chlorodibenzo[b,f][1,4]oxazepin-11-yl)piperazin-2-yl)butanoic acid;
(S,E)-2-(4-(8-chlorodibenzo[b,f][1,4]oxazepin-11-yl)piperazin-2-yl)-2-methylpropanoic acid;
(S,E)-2-(4-(8-chlorodibenzo[b,f][1,4]oxazepin-11-yl)piperazin-2-yl)-2-ethylbutanoic acid;
(R,E)-2-(4-(8-chlorodibenzo[b,f][1,4]oxazepin-11-yl)piperazin-2-yl)acetic acid;
(R)-2-((R)-4-((E)-8-chlorodibenzo[b,f][1,4]oxazepin-11-yl)piperazin-2-yl)propanoic acid;
(S)-2-((R)-4-((E)-8-chlorodibenzo[b,f][1,4]oxazepin-11-yl)piperazin-2-yl)propanoic acid;
(R)-2-((R)-4-((E)-8-chlorodibenzo[b,f][1,4]oxazepin-11-yl)piperazin-2-yl)butanoic acid;
(S)-2-((R)-4-((E)-8-chlorodibenzo[b,f][1,4]oxazepin-11-yl)piperazin-2-yl)butanoic acid;
(R,E)-2-(4-(8-chlorodibenzo[b,f][1,4]oxazepin-11-yl)piperazin-2-yl)-2-methylpropanoic acid;
(R,E)-2-(4-(8-chlorodibenzo[b,f][1,4]oxazepin-11-yl)piperazin-2-yl)-2-ethylbutanoic acid;
(2R)-2-(4-((E)-2-chlorodibenzo[b,f][1,4]oxazepin-11-yl)piperazin-2-yl)propanoic acid;
(2S)-2-(4-((E)-2-chlorodibenzo[b,f][1,4]oxazepin-11-yl)piperazin-2-yl)propanoic acid;
(2R)-2-(4-((E)-2-chlorodibenzo[b,f][1,4]oxazepin-11-yl)piperazin-2-yl)butanoic acid;
(2S)-2-(4-((E)-2-chlorodibenzo[b,f][1,4]oxazepin-11-yl)piperazin-2-yl)butanoic acid;
(E)-2-(4-(2-chlorodibenzo[b,f][1,4]oxazepin-11-yl)piperazin-2-yl)-2-methylpropanoic acid;
(E)-2-(4-(2-chlorodibenzo[b,f][1,4]oxazepin-11-yl)piperazin-2-yl)-2-ethylbutanoic acid;
(E)-ethyl2-(4-(8-chlorodibenzo[b,f][1,4]oxazepin-11-yl)piperazin-2-yl)propanoate;
(E)-ethyl2-(4-(8-chlorodibenzo[b,f][1,4]oxazepin-11-yl)piperazin-2-yl)butanoate;
(E)-ethyl2-(4-(8-chlorodibenzo[b,f][1,4]oxazepin-11-yl)piperazin-2-yl)pentanoate;
(E)-ethyl2-(4-(8-chlorodibenzo[b,f][1,4]oxazepin-11-yl)piperazin-2-yl)-2-methylpropanoate;
(E)-ethyl2-(4-(8-chlorodibenzo[b,f][1,4]oxazepin-11-yl)piperazin-2-yl)-2-ethylbutanoate;
(E)-ethyl2-(4-(8-chlorodibenzo[b,f][1,4]oxazepin-11-y)piperazin-2-yl)-2-methylbutanoate;
(2R)-ethyl2-(4-((E)-2-chlorodibenzo[b,f][1,4]oxazepin-11-yl)piperazin-2-yl)propanoate;
(2S)-ethyl2-(4-((E)-2-chlorodibenzo[b,f][1,4]oxazepin-11-yl)piperazin-2-yl)propanoate;
(2R)-ethyl2-(4-((E)-2-chlorodibenzo[b,f][1,4]oxazepin-11-yl)piperazin-2-yl)butanoate;
(2S)-ethyl2-(4-((E)-2-chlorodibenzo[b,f][1,4]oxazepin-11-yl)piperazin-2-yl)butanoate;
(E)-ethyl2-(4-(2-chlorodibenzo[b,f][1,4]oxazepin-11-yl)piperazin-2-yl)-2-methylpropanoate;
(E)-ethyl2-(4-(2-chlorodibenzo[b,f][1,4]oxazepin-11-yl)piperazin-2-yl)-2-ethylbutanoate;

(R)-ethyl2-((R)-4-((E)-8-chlorodibenzo[b,f][1,4]ox-azepin-11-yl)piperazin-2-yl)propanoate;
(S)-ethyl2-((R)-4-((E)-8-chlorodibenzo[b,f][1,4]ox-azepin-11-yl)piperazin-2-yl)propanoate;
(R)-ethyl2-((R)-4-((E)-8-chlorodibenzo[b,f][1,4]ox-azepin-11-yl)piperazin-2-yl)butanoate;
(S)-ethyl2-((R)-4-((E)-8-chlorodibenzo[b,f][1,4]ox-azepin-11-yl)piperazin-2-yl)butanoate;
(R,E)-ethyl2-(4-(8-chlorodibenzo[b,f][1,4]oxazepin-11-yl)piperazin-2-yl)-2-methylpropanoate;
(R,E)-ethyl2-(4-(8-chlorodibenzo[b,f][1,4]oxazepin-11-yl)piperazin-2-yl)-2-ethylbutanoate;
(S)-ethyl2-((S)-4-((E)-8-chlorodibenzo[b,f][1,4]ox-azepin-11-yl)piperazin-2-yl)propanoate;
(R)-ethyl2-((S)-4-((E)-8-chlorodibenzo[b,f][1,4]ox-azepin-11-yl)piperazin-2-yl)propanoate;
(S)-ethyl2-((S)-4-((E)-8-chlorodibenzo[b,f][1,4]ox-azepin-11-yl)piperazin-2-yl)butanoate;
(R)-ethyl2-((S)-4-((E)-8-chlorodibenzo[b,f][1,4]ox-azepin-11-yl)piperazin-2-yl)butanoate;
(S,E)-ethyl2-(4-(8-chlorodibenzo[b,f][1,4]oxazepin-11-yl)piperazin-2-yl)-2-methylpropanoate;
(S,E)-ethyl2-(4-(8-chlorodibenzo[b,f][1,4]oxazepin-11-yl)piperazin-2-yl)-2-ethylbutanoate;
(E)-methyl2-(4-(8-chlorodibenzo[b,f][1,4]oxazepin-11-yl)piperazin-2-yl)propanoate;
(E)-methyl2-(4-(8-chlorodibenzo[b,f][1,4]oxazepin-11-yl)piperazin-2-yl)butanoate;
(E)-methyl2-(4-(8-chlorodibenzo[b,f][1,4]oxazepin-11-yl)piperazin-2-yl)pentanoate;
(E)-methyl2-(4-(8-chlorodibenzo[b,f][1,4]oxazepin-11-yl)piperazin-2-yl)-2-methylpropanoate;
(E)-methyl2-(4-(8-chlorodibenzo[b,f][1,4]oxazepin-11-yl)piperazin-2-yl)-2-ethylbutanoate;
(E)-methyl2-(4-(8-chlorodibenzo[b,f][1,4]oxazepin-11-yl)piperazin-2-yl)-2-methylbutano ate;
(E)-2-(4-(8-chlorodibenzo[b,f][1,4]oxazepin-11-yl)piper-azin-2-yl)propanoic acid;
(E)-2-(4-(8-chlorodibenzo[b,f][1,4]oxazepin-11-yl)piper-azin-2-yl)butanoic acid;
(E)-2-(4-(8-chlorodibenzo[b,f][1,4]oxazepin-11-yl)piper-azin-2-yl)pentanoic acid;
(E)-2-(4-(8-chlorodibenzo[b,f][1,4]oxazepin-11-yl)piper-azin-2-yl)-2-methylpropanoic acid;
(E)-2-(4-(8-chlorodibenzo[b,f][1,4]oxazepin-11-yl)piper-azin-2-yl)-2-ethylbutanoic acid;
(E)-2-(4-(8-chlorodibenzo[b,f][1,4]oxazepin-11-yl)piper-azin-2-yl)-2-methylbutanoic acid;
(R)-methyl2-((R)-4-((E)-8-chlorodibenzo[b,f][1,4]ox-azepin-11-yl)piperazin-2-yl)propanoate;
(S)-methyl2-((R)-4-((E)-8-chlorodibenzo[b,f][1,4]ox-azepin-11-yl)piperazin-2-yl)propanoate;
(R)-methyl2-((R)-4-((E)-8-chlorodibenzo[b,f][1,4]ox-azepin-11-yl)piperazin-2-yl)butanoate;
(S)-methyl2-((R)-4-((E)-8-chlorodibenzo[b,f][1,4]ox-azepin-11-yl)piperazin-2-yl)butanoate;
(R,E)-methyl2-(4-(8-chlorodibenzo[b,f][1,4]oxazepin-11-yl)piperazin-2-yl)-2-methylpropanoate;
(R,E)-methyl2-(4-(8-chlorodibenzo[b,f][1,4]oxazepin-11-yl)piperazin-2-yl)-2-ethylbutanoate;
(S)-methyl2-((S)-4-((E)-8-chlorodibenzo[b,f][1,4]ox-azepin-11-yl)piperazin-2-yl)propanoate;
(R)-methyl2-((S)-4-((E)-8-chlorodibenzo[b,f][1,4]ox-azepin-11-yl)piperazin-2-yl)propanoate;
(R)-methyl2-((S)-4-((E)-8-chlorodibenzo[b,f][1,4]ox-azepin-11-yl)piperazin-2-yl)butanoate;
(S)-methyl2-((S)-4-((E)-8-chlorodibenzo[b,f][1,4]ox-azepin-11-yl)piperazin-2-yl)butanoate;
(S,E)-methyl2-(4-(8-chlorodibenzo[b,f][1,4]oxazepin-11-yl)piperazin-2-yl)-2-methylpropanoate;
(S,E)-methyl2-(4-(8-chlorodibenzo[b,f][1,4]oxazepin-11-yl)piperazin-2-yl)-2-ethylbutanoate;
(E)-methyl2-((4-(2-chlorodibenzo[b,f][1,4]oxazepin-11-yl)-1-methylpiperazin-2-yl)methoxy)acetate;
(E)-ethyl2-(4-(8-chlorodibenzo[b,f][1,4]oxazepin-11-yl)-1-methylpiperazin-2-yl)acetate;
(E)-2-(4-(8-chlorodibenzo[b,f][1,4]oxazepin-11-yl)-11-methylpiperazin-2-yl)acetic acid;
(E)-methyl2-(4-(8-(trifluoromethyl)dibenzo[b,f][1,4]ox-azepin-11-yl)piperazin-2-yl)acetate;
(S,E)-cyclopentyl2-(4-(8-chlorodibenzo[b,f][1,4]ox-azepin-11-yl)piperazin-2-yl)acetate;
(S)-quinuclidin-3-yl2-((S)-4-((E)-8-chlorodibenzo[b,f][1,4]oxazepin-11-yl)-1-methylpiperazin-2-yl)acetate;
(R)-quinuclidin-3-yl2-((S)-4-((E)-8-chlorodibenzo[b,f][1,4]oxazepin-11-yl)piperazin-2-yl)acetate;
(S)-quinuclidin-3-yl2-((S)-4-((E)-8-chlorodibenzo[b,f][1,4]oxazepin-11-yl)piperazin-2-yl)acetate;
(S,E)-tetrahydro-2H-pyran-4-yl2-(4-(8-chlorodibenzo[b,f][1,4]oxazepin-11-yl)piperazin-2-yl)acetate;
(S,E)-methyl2-(4-(8-chlorodibenzo[b,f][1,4]oxazepin-11-yl)-1-methylpiperazin-2-yl)acetate;
(S,E)-cyclopentyl2-(4-(8-chlorodibenzo[b,f][1,4]ox-azepin-11-yl)-1-methylpiperazin-2-yl)acetate;
sec-butyl2-((S)-4-((E)-8-chlorodibenzo[b,f][1,4]ox-azepin-11-yl)-1-methylpiperazin-2-yl)acetate;
(S,E)-tetrahydro-2H-pyran-4-yl2-(4-(8-chlorodibenzo[b,f][1,4]oxazepin-11-yl)-1-methylpiperazin-2-yl)acetate;
(S,E)-neopentyl2-(4-(8-chlorodibenzo[b,f][1,4]oxazepin-11-yl)piperazin-2-yl)acetate;
(S,E)-3-methoxy-3-methylbutyl2-(4-(8-chlorodibenzo[b,f][1,4]oxazepin-11-yl)piperazin-2-yl)acetate;
(S,E)-3-hydroxy-3-methylbutyl2-(4-(8-chlorodibenzo[b,f][1,4]oxazepin-11-yl)piperazin-2-yl)acetate;
(R)-4-hydroxy-4-methylpentan-2-yl2-((S)-4-((E)-8-chlorodibenzo[b,f][1,4]oxazepin-11-yl)piperazin-2-yl)ac-etate;
(S)-((R)-4-hydroxy-4-methylpentan-2-yl)2-((S)-4-((E)-8-chlorodibenzo[b,f][1,4]oxazepin-11-yl)piperazin-2-yl)propanoate;
(R)(R)-4-hydroxy-4-methylpentan-2-yl)2-((S)-4-((E)-8-chlorodibenzo[b,f][1,4]oxazepin-11-yl)piperazin-2-yl)propanoate;
(S)-((R)-4-hydroxy-4-methylpentan-2-yl)2-((S)-4-((E)-8-chlorodibenzo[b,f][1,4]oxazepin-11-yl)piperazin-2-yl)butanoate;
(R)-((R)-4-hydroxy-4-methylpentan-2-yl)2-((S)-4-((E)-8-chlorodibenzo[b,f][1,4]oxazepin-11-yl)piperazin-2-yl)butanoate;
(R)-4-hydroxy-4-methylpentan-2-yl2-((S)-4-((E)-8-chlorodibenzo[b,f][1,4]oxazepin-11-yl)piperazin-2-yl)-2-methylpropanoate;
(R)-4-hydroxy-4-methylpentan-2-yl2-((S)-4-((E)-8-chlorodibenzo[b,f][1,4]oxazepin-11-yl)piperazin-2-yl)-2-ethylbutanoate;
(2S,4S)-4-hydroxypentan-2-yl2-((S)-4-((E)-8-chlorod-ibenzo[b,f][1,4]oxazepin-11-yl)piperazin-2-yl)acetate;
sec-butyl2-((S)-4-((E)-8-chlorodibenzo[b,f][1,4]ox-azepin-11-yl)piperazin-2-yl)acetate;
(S)-tetrahydrofuran-3-yl2-((S)-4-((E)-8-chlorodibenzo[b,f][1,4]oxazepin-11-yl)piperazin-2-yl)acetate;
(S,E)-ethyl2-(4-(8-chlorodibenzo[b,f][1,4]oxazepin-11-yl)-1-isopentylpiperazin-2-yl)acetate;

(R)-1-methylpyrrolidin-3-yl2-((S)-4-((E)-8-chlorod-
ibenzo[b,f][1,4]oxazepin-11-yl)-1-methylpiperazin-2-
yl)acetate;
(S,E)-methyl2-(4-(8-chlorodibenzo[b,f][1,4]oxazepin-
11-yl)-1-(cyclopropylmethyl)piperazin-2-yl)acetate;
(S,E)-2-(4-(8-chlorodibenzo[b,f][1,4]oxazepin-11-yl)-1-
methylpiperazin-2-yl)-N-(2,2,3,3,3-pentafluoropropyl)
acetamide;
(S,E)-2-(4-(8-chlorodibenzo[b,f][1,4]oxazepin-11-yl)-1-
methylpiperazin-2-yl)-N-(1,3-difluoropropan-2-yl)ac-
etamide;
(S,E)-2-(4-(8-chlorodibenzo[b,f][1,4]oxazepin-11-yl)-1-
methylpiperazin-2-yl)-N,N-bis(2,2,2-trifluoroethypac-
etamide;
(S,E)-3-fluoropropyl2-(4-(8-chlorodibenzo[b,f][1,4]ox-
azepin-11-yl)-1-methylpiperazin-2-yl)acetate;
(S,E)-2-(4-(8-chlorodibenzo[b,f][1,4]oxazepin-11-yl)pip-
erazin-2-yl)-N-(1-hydroxy-2-methylpropan-2-yl)aceta-
mide;
(S,E)-2-(4-(8-chlorodibenzo[b,f][1,4]oxazepin-11-yl)pip-
erazin-2-yl)-N-(2-hydroxyethyl)-N-propylacetamide;
(S,E)-2-(4-(8-chlorodibenzo[b,f][1,4]oxazepin-11-yl)pip-
erazin-2-yl)-N-(2-hydroxyethyl)acetamide;
2-((S)-4-((E)-8-chlorodibenzo[b,f][1,4]oxazepin-11-yl)
piperazin-2-yl)-N-((R)-2-hydroxypropyl)acetamide;
(S,E)-2-(4-(8-chlorodibenzo[b,f][1,4]oxazepin-11-yl)pip-
erazin-2-yl)-N-(2-methoxyethypacetamide;
(R)-2-((S)-4-((E)-8-chlorodibenzo[b,f][1,4]oxazepin-11-
yl)piperazin-2-yl)-N-(2-methoxyethyl)propanamide;
(S)-2-((S)-4-((E)-8-chlorodibenzo[b,f][1,4]oxazepin-11-
yl)piperazin-2-yl)-N-(2-methoxyethyl)propanamide;
(R)-2-((S)-4-((E)-8-chlorodibenzo[b,f][1,4]oxazepin-11-
yl)piperazin-2-yl)-N-(2-methoxyethyl)butanamide;
(S)-2-((S)-4-((E)-8-chlorodibenzo[b,f][1,4]oxazepin-11-
yl)piperazin-2-yl)-N-2-methoxyethyl)butanamide;
(S,E)-2-(4-(8-chlorodibenzo[b,f][1,4]oxazepin-11-yl)pip-
erazin-2-yl)-N-(2-methoxyethyl)-2-methylpropana-
mide;
(S,E)-2-(4-(8-chlorodibenzo[b,f][1,4]oxazepin-11-yl)pip-
erazin-2-yl)-2-ethyl-N-(2-methoxyethyl)butanamide;
(S,E)-2-(4-(8-chlorodibenzo[b,f][1,4]oxazepin-11-yl)pip-
erazin-2-yl)-N-(2-(2-hydroxyethoxy)ethyl)acetamide;
(S,E)-2-(4-(8-chlorodibenzo[b,f][1,4]oxazepin-11-yl)pip-
erazin-2-yl)-N-(2-hydroxyethyl)-N-methylacetamide;
(S,E)-2-(4-(8-chlorodibenzo[b,f][1,4]oxazepin-11-yl)pip-
erazin-2-yl)-N-(6-methoxypyridin-3-yl)acetamide;
(S,E)-2-(4-(8-chlorodibenzo[b,f][1,4]oxazepin-11-yl)pip-
erazin-2-yl)-N-(2,2-difluoroethyl)acetamide;
2-((S)-4-((E)-8-chlorodibenzo[b,f][1,4]oxazepin-11-yl)
piperazin-2-yl)-N-(((S)-tetrahydrofuran-2-yl)methy-
pacetamide;
(S,E)-2-(4-(8-chlorodibenzo[b,f][1,4]oxazepin-11-yl)pip-
erazin-2-yl)-N-(3-hydroxypropyl)acetamide;
(R)-2-((S)-4-((E)-8-chlorodibenzo[b,f][1,4]oxazepin-11-
yl)piperazin-2-yl)-N-(3-hydroxypropyl)propanamide;
(S)-2-((S)-4-((E)-8-chlorodibenzo[b,f][1,4]oxazepin-11-
yl)piperazin-2-yl)-N-(3-hydroxypropyl)propanamide;
(R)-2((S)-4((E)-8-chlorodibenzo[b,f][1,4]oxazepin-11-
yl)piperazin-2-yl)-N-(3-hydroxypropyl)butanamide;
(S)-2-((S)-4-((E)-8-chlorodibenzo[b,f][1,4]oxazepin-11-
yl)piperazin-2-yl)-N-(3-hydroxypropyl)butanamide;
(S,E)-2-(4-(8-chlorodibenzo[b,f][1,4]oxazepin-11-yl)pip-
erazin-2-yl)-N-(3-hydroxypropyl)-2-methylpropa-
narnide;
(S,E)-2-(4-(8-chlorodibenzo[b,f][1,4]oxazepin-11-yl)pip-
erazin-2-yl)-2-ethyl-N-(3-hydroxypropyl)butanamide;

(S,E)-2-(4-(8-chlorodibenzo[b,f][1,4]oxazepin-11-yl)pip-
erazin-2-yl)-N-(3-methoxypropyl)acetamide;
2-((S)-4-((E)-8-chlorodibenzo[b,f][1,4]oxazepin-11-yl)
piperazin-2-yl)-1-((R)-3-hydroxypyrrolidin-1-yl)etha-
none;
2((S)-4-((E)-8-chlorodibenzo[b,f][1,4]oxazepin-11-yl)
piperazin-2-yl)-N-(3,3,3-trifluoro-2-hydroxypropyl)
acetamide;
(S,E)-2-(4-(8-chlorodibenzo[b,f][1,4]oxazepin-11-yl)pip-
erazin-2-yl)-1-morpholinoethanone;
2-((S)-4-((E)-8-chlorodibenzo[b,f][1,4]oxazepin-11-yl)
piperazin-2-yl)-1-((S)-2-(trifluoromethyl)pyrrolidin-1-
yl)ethanone; or (S,E)-2-(4-(8-chlorodibenzo[b,f][1,4]
oxazepin-11-yl)-1-(2-hydroxyethyl)piperazin-2-yl)-N-
(2-methoxyethypacetamide.
24. A compound or salt according to claim 1, wherein the compound is
(E)-ethyl2-(4-(8-chlorodibenzo[b,f][1,4]oxazepin-11-yl)
piperazin-2-yl)acetate;
(E)-2-(4-(8-chlorodibenzo[b,f][1,4]oxazepin-11-yl)piper-
azin-2-yl)acetic acid;
(E)-methyl2-(4-(8-chlorodibenzo[b,f][1,4]oxazepin-11-
yl)piperazin-2-yl)acetate;
(S,E)-ethyl2-(4-(8-chlorodibenzo[b,f][1,4]oxazepin-11-
yl)piperazin-2-yl)acetate;
(S,E)-methyl2-(4-(8-chlorodibenzo[b,f][1,4]oxazepin-
11-yl)piperazin-2-yl)acetate;
(R,E)-ethyl2-(4-(8-chlorodibenzo[b,f][1,4]oxazepin-11-
yl)piperazin-2-yl)acetate;
(R,E)-methyl2-(4-(8-chlorodibenzo[b,f][1,4]oxazepin-
11-yl)piperazin-2-yl)acetate;
(S,E)-2-(4-(8-chlorodibenzo[b,f][1,4]oxazepin-11-yl)pip-
erazin-2-yl)acetic acid;
(R)-2-((S)-4-((E)-8-chlorodibenzo[b,f][1,4]oxazepin-11-
yl)piperazin-2-yl)propanoic acid;
(S)-2-((S)-4-((E)-8-chlorodibenzo[b,f][1,4]oxazepin-11-
yl)piperazin-2-yl)propanoic acid;
(R)-2-((S)-4-((E)-8-chlorodibenzo[b,f][1,4]oxazepin-11-
yl)piperazin-2-yl)butanoic acid;
(S)-2-((S)-4-((E)-8-chlorodibenzo[b,f][1,4]oxazepin-11-
yl)piperazin-2-yl)butanoic acid;
(S,E)-2-(4-(8-chlorodibenzo[b,f][1,4]oxazepin-11-yl)pip-
erazin-2-yl)-2-methylpropanoic acid;
(S,E)-2-(4-(8-chlorodibenzo[b,f][1,4]oxazepin-11-yl)pip-
erazin-2-yl)-2-ethylbutanoic acid;
(R,E)-2-(4-(8-chlorodibenzo[b,f][1,4]oxazepin-11-yl)
piperazin-2-yl)acetic acid;
(R)-2-((R)-4-((E)-8-chlorodibenzo[b,f][1,4]oxazepin-11-
yl)piperazin-2-yl)propanoic acid;
(S)-2-((R)-4-((E)-8-chlorodibenzo[b,f][1,4]oxazepin-11-
yl)piperazin-2-yl)propanoic acid;
(R)-2-((R)-4-((E)-8-chlorodibenzo[b,f][1,4]oxazepin-11-
yl)piperazin-2-yl)butanoic acid;
(S)-2-((R)-4-((E)-8-chlorodibenzo[b,f][1,4]oxazepin-11-
yl)piperazin-2-yl)butanoic acid;
(R,E)-2-(4-(8-chlorodibenzo[b,f][1,4]oxazepin-11-yl)
piperazin-2-yl)-2-methylpropanoic acid;
(R,E)-2-(4-(8-chlorodibenzo[b,f][1,4]oxazepin-11-yl)
piperazin-2-yl)-2-ethylbutanoic acid;
(2R)-2-(4-((E)-2-chlorodibenzo[b,f][1,4]oxazepin-11-yl)
piperazin-2-yl)propanoic acid;
(2S)-2-(4-((E)-2-chlorodibenzo[b,f][1,4]oxazepin-11-yl)
piperazin-2-yl)propanoic acid;
(2R)-2-(4-((E)-2-chlorodibenzo[b,f][1,4]oxazepin-11-yl)
piperazin-2-yl)butanoic acid;
(2S)-2-(4-((E)-2-chlorodibenzo[b,f][1,4]oxazepin-11-yl)
piperazin-2-yl)butanoic acid;

(E)-2-(4-(2-chlorodibenzo[b,f][1,4]oxazepin-11-yl)piperazin-2-yl)-2-methylpropanoic acid;
(E)-2-(4-(2-chlorodibenzo[b,f][1,4]oxazepin-11-yl)piperazin-2-yl)-2-ethylbutanoic acid;
(E)-ethyl2-(4-(8-chlorodibenzo[b,f][1,4]oxazepin-11-yl)piperazin-2-yl)propanoate;
(E)-ethyl2-(4-(8-chlorodibenzo[b,f][1,4]oxazepin-11-yl)piperazin-2-yl)butanoate;
(E)-ethyl2-(4-(8-chlorodibenzo[b,f][1,4]oxazepin-11-yl)piperazin-2-yl)pentanoate;
(E)-ethyl2-(4-(8-chlorodibenzo[b,f][1,4]oxazepin-11-yl)piperazin-2-yl)-2-methylpropanoate;
(E)-ethyl2-(4-(8-chlorodibenzo[b,f][1,4]oxazepin-11-yl)piperazin-2-yl)-2-ethylbutanoate;
(E)-ethyl2-(4-(8-chlorodibenzo[b,f][1,4]oxazepin-11-yl)piperazin-2-yl)-2-methylbutanoate;
(2R)-ethyl2-(4-((E)-2-chlorodibenzo[b,f][1,4]oxazepin-11-yl)piperazin-2-yl)propanoate;
(2S)-ethyl2-(4-((E)-2-chlorodibenzo[b,f][1,4]oxazepin-11-yl)piperazin-2-yl)propanoate;
(2R)-ethyl2-(4-((E)-2-chlorodibenzo[b,f][1,4]oxazepin-11-yl)piperazin-2-yl)butanoate;
(2S)-ethyl2-(4-((E)-2-chlorodibenzo[b,f][1,4]oxazepin-11-yl)piperazin-2-yl)butanoate;
(E)-ethyl2-(4-(2-chlorodibenzo[b,f][1,4]oxazepin-11-yl)piperazin-2-yl)-2-methylpropanoate;
(E)-ethyl2-(4-(2-chlorodibenzo[b,f][1,4]oxazepin-11-yl)piperazin-2-yl)-2-ethylbutanoate;
(R)-ethyl2-((R)-4-((E)-8-chlorodibenzo[b,f][1,4]oxazepin-11-yl)piperazin-2-yl)propanoate;
(S)-ethyl2-((R)-4-((E)-8-chlorodibenzo[b,f][1,4]oxazepin-11-yl)piperazin-2-yl)propanoate;
(R)-ethyl2-((R)-4-((E)-8-chlorodibenzo[b,f][1,4]oxazepin-11-yl)piperazin-2-yl)butanoate;
(S)-ethyl2-((R)-4-((E)-8-chlorodibenzo[b,f][1,4]oxazepin-11-yl)piperazin-2-yl)butanoate;
(R,E)-ethyl2-(4-(8-chlorodibenzo[b,f][1,4]oxazepin-11-yl)piperazin-2-yl)-2-methylpropanoate;
(R,E)-ethyl2-(4-(8-chlorodibenzo[b,f][1,4]oxazepin-11-yl)piperazin-2-yl)-2-ethylbutanoate;
(S)-ethyl2-((S)-4-((E)-8-chlorodibenzo[b,f][1,4]oxazepin-11-yl)piperazin-2-yl)propanoate;
(R)-ethyl2-((S)-4-((E)-8-chlorodibenzo[b,f][1,4]oxazepin-11-yl)piperazin-2-yl)propanoate;
(S)-ethyl2-((S)-4-((E)-8-chlorodibenzo[b,f][1,4]oxazepin-11-yl)piperazin-2-yl)butanoate;
(R)-ethyl2-((S)-4-((E)-8-chlorodibenzo[b,f][1,4]oxazepin-11-yl)piperazin-2-yl)butanoate;
(S,E)-ethyl2-(4-(8-chlorodibenzo[b,f][1,4]oxazepin-11-yl)piperazin-2-yl)-2-methylpropanoate;
(S,E)-ethyl2-(4-(8-chlorodibenzo[b,f][1,4]oxazepin-11-yl)piperazin-2-yl)-2-ethylbutanoate;
(E)-methyl2-(4-(8-chlorodibenzo[b,f][1,4]oxazepin-11-yl)piperazin-2-yl)propanoate;
(E)-methyl2-(4-(8-chlorodibenzo[b,f][1,4]oxazepin-11-yl)piperazin-2-yl)butanoate;
(E)-methyl2-(4-(8-chlorodibenzo[b,f][1,4]oxazepin-11-yl)piperazin-2-yl)pentanoate;
(E)-methyl2-(4-(8-chlorodibenzo[b,f][1,4]oxazepin-11-yl)piperazin-2-yl)-2-methylpropanoate;
(E)-methyl2-(4-(8-chlorodibenzo[b,f][1,4]oxazepin-11-yl)piperazin-2-yl)-2-ethylbutanoate;
(E)-methyl2-(4-(8-chlorodibenzo[b,f][1,4]oxazepin-11-yl)piperazin-2-yl)-2-methylbutanoate;
(E)-2-(4-(8-chlorodibenzo[b,f][1,4]oxazepin-11-yl)piperazin-2-yl)propanoic acid;
(E)-2-(4-(8-chlorodibenzo[b,f][1,4]oxazepin-11-yl)piperazin-2-yl)butanoic acid;
(E)-2-(4-(8-chlorodibenzo[b,f][1,4]oxazepin-11-yl)piperazin-2-yl)pentanoic acid;
(E)-2-(4-(8-chlorodibenzo[b,f][1,4]oxazepin-11-yl)piperazin-2-yl)-2-methylpropanoic acid;
(E)-2-(4-(8-chlorodibenzo[b,f][1,4]oxazepin-11-yl)piperazin-2-yl)-2-ethylbutanoic acid;
(E)-2-(4-(8-chlorodibenzo[b,f][1,4]oxazepin-11-yl)piperazin-2-yl)-2-methylbutanoic acid;
(R)-methyl2-((R)-4-((E)-8-chlorodibenzo[b,f][1,4]oxazepin-11-yl)piperazin-2-yl)propanoate;
(S)-methyl2-((R)-4-((E)-8-chlorodibenzo[b,f][1,4]oxazepin-11-yl)piperazin-2-yl)propanoate;
(R)-methyl2-((R)-4-((E)-8-chlorodibenzo[b,f][1,4]oxazepin-11-yl)piperazin-2-yl)butanoate;
(S)-methyl2-((R)-4-((E)-8-chlorodibenzo[b,f][1,4]oxazepin-11-yl)piperazin-2-yl)butanoate;
(R,E)-methyl2-(4-(8-chlorodibenzo[b,f][1,4]oxazepin-11-yl)piperazin-2-yl)-2-methylpropanoate;
(R,E)-methyl2-(4-(8-chlorodibenzo[b,f][1,4]oxazepin-11-yl)piperazin-2-yl)-2-ethylbutanoate;
(S)-methyl2-((S)-4-((E)-8-chlorodibenzo[b,f][1,4]oxazepin-11-yl)piperazin-2-yl)propanoate;
(R)-methyl2-((S)-4-((E)-8-chlorodibenzo[b,f][1,4]oxazepin-11-yl)piperazin-2-yl)propanoate;
(R)-methyl2-((S)-4-((E)-8-chlorodibenzo[b,f][1,4]oxazepin-11-yl)piperazin-2-yl)butanoate;
(S)-methyl2-((S)-4-((E)-8-chlorodibenzo[b,f][1,4]oxazepin-11-yl)piperazin-2-yl)butanoate;
(S,E)-methyl2-(4-(8-chlorodibenzo[b,f][1,4]oxazepin-11-yl)piperazin-2-yl)-2-methylpropanoate;
(S,E)-methyl2-(4-(8-chlorodibenzo[b,f][1,4]oxazepin-11-yl)piperazin-2-yl)-2-ethylbutanoate;
(R)-4-hydroxy-4-methylpentan-2-yl2-((S)-4-((E)-8-chlorodibenzo[b,f][1,4]oxazepin-11-yl)piperazin-2-yl)acetate;
(S)-((R)-4-hydroxy-4-methylpentan-2-yl)2-((S)-4-((E)-8-chlorodibenzo[b,f][1,4]oxazepin-11-yl)piperazin-2-yl)propanoate;
(R)-((R)-4-hydroxy-4-methylpentan-2-yl)2-((S)-4-((E)-8-chlorodibenzo[b,f][1,4]oxazepin-11-yl)piperazin-2-yl)propanoate;
(S)-((R)-4-hydroxy-4-methylpentan-2-yl)2-((S)-4-((E)-8-chlorodibenzo[b,f][1,4]oxazepin-11-yl)piperazin-2-yl)butanoate;
(R)-((R)-4-hydroxy-4-methylpentan-2-yl)2-((S)-4-((E)-8-chlorodibenzo[b,f][1,4]oxazepin-11-yl)piperazin-2-yl)butanoate;
(R)-4-hydroxy-4-methylpentan-2-yl2-((S)-4-((E)-8-chlorodibenzo[b,f][1,4]oxazepin-11-yl)piperazin-2-yl)-2-methylpropanoate;
(R)-4-hydroxy-4-methylpentan-2-yl2-((S)-4-((E)-8-chlorodibenzo[b,f][1,4]oxazepin-11-yl)piperazin-2-yl)-2-ethylbutanoate;
(S,E)-2-(4-(8-chlorodibenzo[b,f][1,4]oxazepin-11-yl)piperazin-2-yl)-N-(2-methoxyethyl)acetamide;
(R)-2-((S)-4-((E)-8-chlorodibenzo[b,f][1,4]oxazepin-11-yl)piperazin-2-yl)-N-(2-methoxyethyl)propanamide;
(S)-2-((S)-4-((E)-8-chlorodibenzo[b,f][1,4]oxazepin-11-yl)piperazin-2-yl)-N-(2-methoxyethyl)propanarnide;
(R)-2-((S)-4-((E)-8-chlorodibenzo[b,f][1,4]oxazepin-11-yl)piperazin-2-yl)-N-(2-methoxyethyl)butanamide;
(S)-2-((S)-4-((E)-8-chlorodibenzo[b,f][1,4]oxazepin-11-yl)piperazin-2-yl)-N-(2-methoxyethyl)butanamide;

(S,E)-2-(4-(8-chlorodibenzo[b,f][1,4]oxazepin-11-yl)piperazin-2-yl)-N-(2-methoxyethyl)-2-methylpropanamide;

(S,E)-2-(4-(8-chlorodibenzo[b,f][1,4]oxazepin-11-yl)piperazin-2-yl)-2-ethyl-N-(2-methoxyethyl)butanamide;

(S,E)-2-(4-(8-chlorodibenzo[b,f][1,4]oxazepin-11-yl)piperazin-2-yl)-N-(3-hydroxypropyl)acetamide;

(R)-2-((S)-4-((E)-8-chlorodibenzo[b,f][1,4]oxazepin-11-yl)piperazin-2-yl)-N-(3-hydroxypropyl)propanamide;

(S)-2-((S)-4-((E)-8-chlorodibenzo[b,f][1,4]oxazepin-11-yl)piperazin-2-yl)-N-(3-hydroxypropyl)propanamide;

(R)-2-((S)-4-((E)-8-chlorodibenzo[b,f][1,4]oxazepin-11-yl)piperazin-2-yl)-N-(3-hydroxypropyl)butanamide;

(S)-2-((S)-4-((E)-8-chlorodibenzo[b,f][1,4]oxazepin-11-yl)piperazin-2-yl)-N-(3hydroxypropyl)butanamide;

(S,E)-2-(4-(8-chlorodibenzo[b,f][1,4]oxazepin-11-yl)piperazin-2-yl)-N-(3-hydroxypropyl)-2-methylpropanamide; or (S,E)-2-(4-(8-chlorodibenzo[b,f][1,4]oxazepin-11-yl)piperazin-2-yl)-2-ethyl1-N-(3-hydroxypropyl)butanamide.

25. A compound or salt according to claim 21, wherein the compound is (S,E)-ethyl2-(4-(8-chlorodibenzo[b,f][1,4]oxazepin-11-yl)piperazin-2-yl)acetate;

(S,E)-methyl2-(4-(8-chlorodibenzo[b,f][1,4]oxazepin-11-yl)piperazin-2-yl)acetate;

(S)-ethyl2-((S)-4-((E)-8-chlorodibenzo[b,f][1,4]oxazepin-11-yl)piperazin-2-yl)propanoate;

(R)-ethyl2-((S)-4-((E)-8-chlorodibenzo[b,f][1,4]oxazepin-11-yl)piperazin-2-yl)propanoate;

(S,E)-ethyl2-(4-(8-chlorodibenzo[b,f][1,4]oxazepin-11-yl)piperazin-2-yl)-2-methylpropanoate;

(S)-methyl2-((S)-4-((E)-8-chlorodibenzo[b,f][1,4]oxazepin-11-yl)piperazin-2-yl)propanoate;

(R)-methyl2-((S)-4-((E)-8-chlorodibenzo[b,f][1,4]oxazepin-11-yl)piperazin-2-yl)propanoate; or (S,E)-methyl2-(4-(8-chlorodibenzo[b,f][1,4]oxazepin-11-yl)piperazin-2-yl)-2-methylpropanoate.

26. A compound or salt according to claim 21, wherein the compound is (S,E)-2-(4-(8-chlorodibenzo[b,f][1,4]oxazepin-11-yl)piperazin-2-yl)acetic acid;

(R)-2-((S)-4-((E)-8-chlorodibenzo[b,f][1,4]oxazepin-11-yl)piperazin-2-yl)propanoic acid;

(S)-2-((S)-4-((E)-8-chlorodibenzo[b,f][1,4]oxazepin-11-yl)piperazin-2-yl)propanoic acid; or (S,E)-2-(4-(8-chlorodibenzo[b,f][1,4]oxazepin-11-yl)piperazin-2-yl)-2-methylpropanoic acid.

27. A composition comprising a compound or salt of claim 1 and at least one pharmaceutically acceptable glidant, solvent, adjuvant, diluent, lubricant, excipient, or combination thereof.

28. A composition comprising a compound or salt of claim 3 and at least one pharmaceutically acceptable glidant, solvent, adjuvant, diluent, lubricant, excipient, or combination thereof.

29. A composition comprising a compound or salt of claim 12 and at least one pharmaceutically acceptable glidant, solvent, adjuvant, diluent, lubricant, excipient, or combination thereof.

30. A composition comprising a compound or salt of claim 21 and at least one pharmaceutically acceptable glidant, solvent, adjuvant, diluent, lubricant, excipient, or combination thereof.

31. A composition comprising a compound or salt of claim 23 and at least one pharmaceutically acceptable glidant, solvent, adjuvant, diluent, lubricant, excipient, or combination thereof.

32. A composition comprising a compound or salt of claim 24 and at least one pharmaceutically acceptable glidant, solvent, adjuvant, diluent, lubricant, excipient, or combination thereof.

33. A method of treating schizophrenia, treatment-resistant schizophrenia, bipolar disorder, psychotic depression, treatment-resistant depression, obsessive-compulsive disorder (OCD), autism, senile psychosis, psychotic dementia, L-DOPA induced psychosis, psychogenic polydipsia, psychotic symptoms associated with neurological disorders, sleep disorders, depressed states associated with schizophrenia, the method comprising administering a compound or salt according to claim 1 to a patient in need of such treatment.

34. A method of treating schizophrenia, treatment-resistant schizophrenia, bipolar disorder, psychotic depression, treatment-resistant depression, obsessive-compulsive disorder (OCD), autism, senile psychosis, psychotic dementia, L-DOPA induced psychosis, psychogenic polydipsia, psychotic symptoms associated with neurological disorders, sleep disorders, depressed states associated with schizophrenia, the method comprising administering a compound or salt according to claim 23 to a patient in need of such treatment.

35. A method of treating schizophrenia, treatment-resistant schizophrenia, bipolar disorder, psychotic depression, treatment-resistant depression, obsessive-compulsive disorder (OCD), autism, senile psychosis, psychotic dementia, L-DOPA induced psychosis, psychogenic polydipsia, psychotic symptoms associated with neurological disorders, sleep disorders, depressed states associated with schizophrenia, the method comprising administering a compound or salt according to claim 24 to a patient in need of such treatment.

36. A method for preparing a compound of Formula F

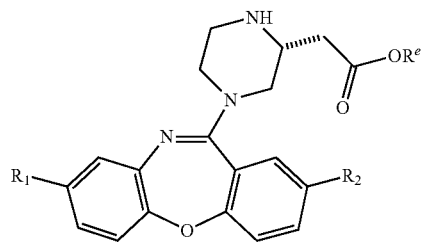

Formula (F)

comprising:

1) converting a compound of formula (A)

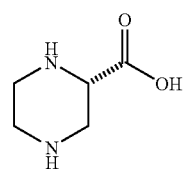

(A)

or its salt to a compound of formula (B)

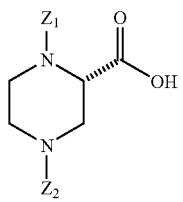
(B)

or its salt, respectively, wherein $Z_1$ and $Z_2$ are nitrogen protecting groups that are selected from the group consisting of benzyl, nitrobenzyl, Boc, oxide, paramethoxybenzyl, benzylsulfonyl, and carbobenzyloxy;

2) converting compound of formula (B)

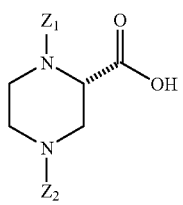
(B)

to an acid chloride followed by converting to the diazide of formula (C)

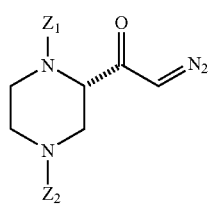
(C)

wherein $Z_1$ and $Z_2$ are nitrogen protecting groups;

3) treating a compound of formula (C)

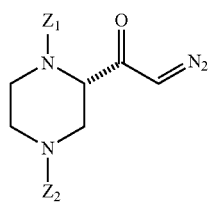
(C)

with a silver catalyst and an alcohol to make formula (D)

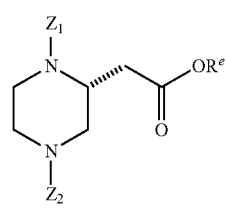
(D)

wherein $Z_1$ and $Z_2$ are nitrogen protecting groups, $R^e$ is $C_1$-$C_6$ alk;

4) deprotecting a compound of formula (D)

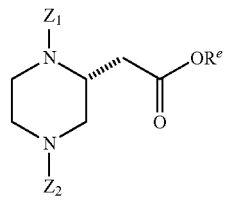
(D)

or its salt to a compound of formula (E)

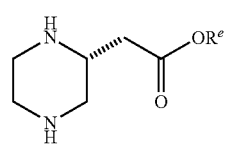
(E)

or its salt, respectively, wherein $R^e$ is $C_1$-$C_6$ alk;

5) alkylating a compound of formula (E)

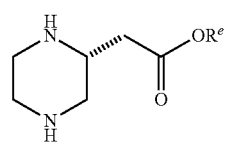
(E)

or its salt with a compound of formula (G)

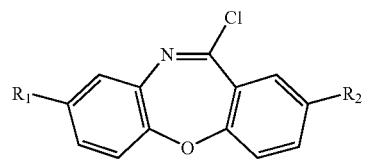
(G)

or its salt, wherein $R_1$ and $R_2$ are independently H, I, Br, Cl, or I, to a compound of formula (F)

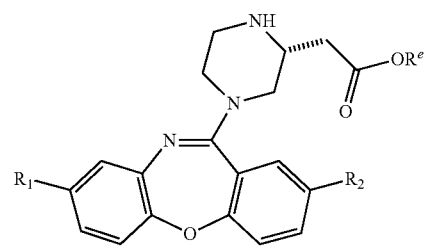
(F)

or its salt, respectively, wherein $R^e$ is $C_1$-$C_6$ alk, $R_1$ and $R_2$ are independently H, I, Br, Cl, or I, and wherein in each instance the bond between the piperazine and carbonyl moiety is racemic, R or S.

* * * * *